(12) United States Patent
Weill et al.

(10) Patent No.: US 8,673,568 B2
(45) Date of Patent: Mar. 18, 2014

(54) **MOLECULAR TYPING AND SUBTYPING OF *SALMONELLA* BY IDENTIFICATION OF THE VARIABLE NUCLEOTIDE SEQUENCES OF THE CRISPR LOCI**

(75) Inventors: François-Xavier Weill, Paris (FR);
Laetitia Fabre, Pontchartrain (FR);
Véronique Guibert, Vernouillet (FR);
Laure Diancourt, Herslay (FR); Sylvain Brisse, Clamart (FR)

(73) Assignee: Institut Pasteur, Paris (FR)

( * ) Notice: Subject to any disclaimer, the term of this patent is extended or adjusted under 35 U.S.C. 154(b) by 537 days.

(21) Appl. No.: 12/811,055

(22) PCT Filed: Dec. 29, 2008

(86) PCT No.: PCT/IB2008/004004
§ 371 (c)(1),
(2), (4) Date: Oct. 25, 2010

(87) PCT Pub. No.: WO2009/115861
PCT Pub. Date: Sep. 24, 2009

(65) Prior Publication Data
US 2012/0088676 A1 Apr. 12, 2012

(30) Foreign Application Priority Data
Dec. 28, 2007 (FR) ...................................... 07 09188

(51) Int. Cl.
*C12Q 1/68* (2006.01)
*C12P 19/34* (2006.01)

(52) U.S. Cl.
USPC ......................................... 435/6.12; 435/91.2

(58) Field of Classification Search
None
See application file for complete search history.

(56) References Cited

U.S. PATENT DOCUMENTS

2006/0177824 A1* 8/2006 Procop ............................... 435/6
2008/0124725 A1* 5/2008 Barrangou et al. ............... 435/6

FOREIGN PATENT DOCUMENTS

WO WO-99/51771 10/1999
WO WO-2007/136815 A2 11/2007

OTHER PUBLICATIONS

Witonski et al., "Variable-Number Tandem Repeats that are Useful in Genotyping Isolates of *Salmonella enterica* subsp. *enterica* Serovars Typhimurium and Newport," Journal of Clinical Microbiology, vol. 44, No. 11, pp. 3849-3854, (2006).
Lindstedt et al., "Multiple-Locus Variable-Number Tandem-Repeats Analysis of *Salmonella enterica* subsp. *enterica* Serovar Typhimurium using PCR Multiplexing and Multicolor Capillary Electrophoresis," Journal of Microbiological Methods, vol. 59, pp. 163-172, (2004).
Liu et al., "Molecular Typing of *Salmonella enterica* Serovar Typhi Isolates from Varios Countries in Asia by Multiplex PCR Assays on Variable-Number Tandem Repeats," Journal of Clinical Microbiology, vol. 41, No. 9, pp. 4388-4394, (2003).
Ramisse et al., "Variable Number of Tandem Repeats in *Salmonella enterica* Subsp. *enterica* for Typing Purposes," Journal of Clinical Microbiology, vol. 42, No. 12, pp. 5722-5730, (2004).
Pourcel et al., "CRISPR Elements in *Yersinia pestis* Acquire New Repeats by Preferential Update of Bacteriophage DNA, and Provide Additional Tools for Evolutionary Studies," Microbiology, vol. 151, pp. 653-663, (2005).
Nakata et al., "Unusual Nucleotide Arrangement with Repeated Sequences in the *Escherichia coli* K-12 Chromosome," Journal of Bacteriology, vol. 171, No. 6, pp. 3553-3556, (1989).
Jansen et al., "Identification of Novel Family of Sequence Repeats Among Prokaryotes," OMICS A Journal of Integrative Biology, vol. 6, No. 1, pp. 22-33, (2002).
Godde et al., "The Repetitive DNA Elements called CRISPRs and Their Associated Genes: Evidence of Horizontal Transfer Among Prokaryotes," Journal of Molecular Evolution, vol. 62, pp. 718-729, (2006).
Grissa et al., "CRISPRFinder: A Web Tool to Identify Clustered Regulary Interspaced Short Palindromic Repeats," Nucleic Acids Research, vol. 35, pp. W52-W57, (2007).
Groenen et al., "Nature of DNA Polymorphism in the Direct Repeat Cluster of *Mycobacterium Tuberculosis*; Application for Strain Differentation by a Novel Typing Method," Molecular Microbiology, vol. 10, No. 5, pp. 1507-1065, (1993).
Grimont et al., "Centre National De Références Des *Salmonella*," Rapport d'activité annuel, pp. 28 and 43, (2005).
International Search Report from the European Patent Office for International Application No. PCT/IB2008/004004 (Mail date: Feb. 12, 2010).

* cited by examiner

*Primary Examiner* — Kenneth R. Horlick
*Assistant Examiner* — David Thomas
(74) *Attorney, Agent, or Firm* — Finnegan, Henderson, Farabow, Garrett & Dunner LLP

(57) ABSTRACT

The present invention relates to a method for detecting and identifying bacteria of the *Salmonella* genus by identification of the variable nucleotide sequences contained in the CRISPR loci of these bacteria, and also to diagnostic reagents, such as oligonucleotide primers and probes, for molecular typing and subtyping of these bacteria.

17 Claims, 89 Drawing Sheets

A
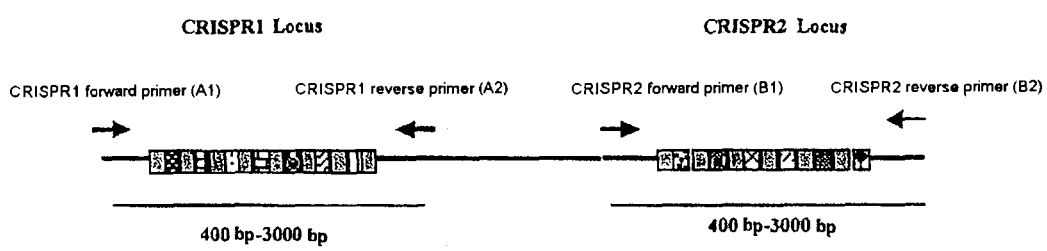
B
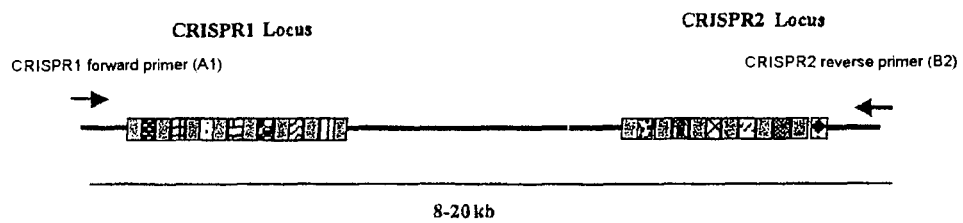
FIGURE 1

6A
TGCCAGGGCGAATTGAGCGCCGTAGCCGCGATGTAGTACGGATAATGCTGCCGTTGGTAAAAGAG
CTGGCGAAGGCGGAAAAAACGTCCTGATATGCTGGTGAAACGTGTTTATCCCCGCTGACGCGGGGA
ACACTATTTATAAGCGTGTCATCTATGCAACCCAACCGGTTTATCCCCGCTGGCGCGGGGAACACA
CCTGCCCGACCCAATAAGGGGGCCCTCGTGACGGTTTATCCCCGCTGGCGCGGGGAACACGGCCG
CTGGTCAAATTCCCAATCTGAGCAATCCGGTTTATCCCCGCTGGCGCGGGGAACACATAGCCCCGG
CAGCGATAGCTAAACCAGTTCCCGGTTTATCCCCGCTGGCGCGGGGAACACGCCTCAAAATCTCTC
GGTGAGATGTAAGCGTCCGGTTTATCCCCGCTGGCGCGGGGAACACACCAGTGGTCAGCGGCGGA
TGAATTTGCCCTGCGGTTTATCCCCGCTGGCGCGGGGAACACGAGAATGCTCATGCGCGTGAGCGC
CATATATTCGGTTTATCCCCGCTGGCGCGGGGAACACAGGCGGACCGAAAAACCGTTTTCAGCCA
ACGTCGGTTTATCCCCGCTGGCGCGGGGAACACACTAAAACTATATATTTGTTCTAAAAGCCCTTTT
TTACTACATAACAAACTACCAACGGTAAGATAACAATTCCTTATCATTAAAGAACATTCAACTTAT
TGATTTTCAACAGGAAGAAAAGAAACCAAACGCAGTCCATCCAAATCTACCGGAATACG

6B
CCCCGGGAAAACGCGGCCTTTTTACTTTACAGGTTTGTACCAGCCATTACTGGTACACAGATTATGA
TTATGCAACGGCTATCCTTGTTGGCGCGGGGAACACGGCTACACGCAAAAATTCCAGTCGTTGGCG
CACGGTTTATCCCCGCTGGCGCGGGGAACACCCGATTAAGATCCGCAGTCTGCATCAGTAACTCGG
TTTATCCCCGCTGGCGCGGGGAACACCGATTCTACGGCAACAGGCCAGGCTGCGACCGCGGTTTAT
CCCCGCTGGCGCGGGGAACACATCAAACATGGAAACCCCTTTAATGAGAGCAACGGTTTATCCCCG
GCTGGCGCGGGGAACACTCAGGAACGCGCGGCGGAAGAGCTTGGTGTTTGCGGTTTATCCCCGCT
GGCGCGGGGAACACGCTGCCTTTCCCGGAGTTCCGGCCCCTAAATTGGGTTTATCCCCGCTGGCGC
GGGGAACACTCATGCGCTATAAAAATCAGACTGTCACATGCCGGTTTATCCCCGCTGGCGCGGGGA
ACACTGATTATTGACGACAACAGCACAGACCGGCAGCAGTTTATCCCCGCTGGCGCGGGGAACAC
AATAATCGGCAATTTGTCCTGGACAGGCACGGCAGTTTATCCCCGCTGGCGCGGGGAACACGAAT
CTGGAGGCCAACAGCGCGGCGAAATCCTCAGTTTATCCCCGCTGGCGCGGGGAACACACTAAACG
TATGTCATTGTTTATAAACTACTTTTTATCAGCACCACATTCCACCAACATAATCGCAACAATTTAA
ATTATTAAAGAACAGCTAATTTGCTGATTTTGATGCAAAAAAGTTCATAGAATGATTTTTTCTTTAA
ATTTACCAAAATAGCGCGATCCGTGCATCGCTATGGAAAAATTTATCAGCGCTTTTATACACTCATC
GAAATTCACATAGAGAAAATAAACAATGCAAGGTAATGGATGAGTCACAGACGGCATC

FIGURE 6

7A
GAGCGCCGTAGCCGCGATGTAGTACGGATAATGCTGCCGTTGGTAAAAGAGCTGGCGAAGGCGGA
AAAAACGTCCTGATATGCTGGTGAAACGTGTTTATCCCCGCTGACGCGGGGAACACTATTTATAAG
CGTGTCATCTATGCAACCCAACCGGTTTATCCCCGCTGGCGCGGGGAACACACCTGCCCGACCCAA
TAAGGAGGCCCTCGTGACGGTTTATCCCCGCTGGCGCGGGGAACACGGCCGCTGGTCAAATTCCC
AATCTGAGCAATCGGGTTTATCCCCGCTGGCGCGGGGAACACATAGCCCCGGCAGCGATAGCTAA
ACCAGTTCCCGGTTTATCCCCGCTGGCGCGGGGAAGACGCCTCAAAATCTCTCGGTGAGATGTAAG
CGTCCGGTTTATCCCCGCTGGCGCGGGGAACACACCAGTGGTCAGCGGCGGATGAATTTGCCCTGC
GGTTTATCCCCGCTGGCGCGGGGAACACGAGAATGCTCATGCGCGTGAGCGCCATATATTCGGTTT
ATCCCCGGCTGGCGCGGGGAACACCATGGCAATTTTACGGCGGACGTGCTCGCTCTCGGTTTATCCC
CGCTGGCGCGGGGAACACAGGCGGACCGAAAAACCGTTTTCAGCCAACGTCGGTTTATCCCCGGCT
GGCGCGGGGAACACACTAAAACTATATATTTGTTCTAAAAGCCCTTTTTTACTACATAACAAACTA
CCAACGGTAAGATAACAATTCCTTATCATTAAAGAACATTCAACTTATTGATTTTCAACAGGAAGA
AAAGAAACCAAACGCAGTCCATCCAAATCTACCGGAATACG

7B
TGTAGAAAAGCCTCCCCCGGGAAAACGCGGCCTTTTTACTTTACAGGTTTGTACCAGCCATTACTG
GTACACAGATTATGATTATGCAACGGCTATCCTTGTTGGCGCGGGGAACACGGCTACACGCAAAA
ATTCCAGTCGTTGGCGCACGGTTTATCCCCGCTGGCGCGGGGAACACCCGATTAAGATCCGCAGTC
TGCATCAGTAACTCGGTTTATCCCCGCTGGCGAGGGGAACACCGATTCTACGGCAACAGGCCAGG
CTGCGACCGCGGTTTATCCCCGCTGGCGCGGGGAACACATCAAACATGGAAACCCCTTTAATGAG
AGCAACGGTTTATCCCCGCTGGCGCGGGGAACACTCAGGAACGCGCGGCGGAAGAGCTTGGTGTT
TGCGGTTTATCCCCGCTGGCGCGGGGAACACGCTGCCTTTCCCGGAGTTCCGGCCCCTAAATTGGG
TTTATCCCCGCTGGCGCGGGGAACACTCATGCGCTATAAAAATCAGACTGTCACATGCCGGTTTAT
CCCCGCTGGCGCGGGGAACACTGATTATTGACGACAACAGCACAGACCGGCAGCAGTTTATCCCC
GCTGGCGCGGGGAACACAATAATCGGCAATTTGTCCTGGACAGGCACGGCAGTTTATCCCCGCTGG
CGCGGGGAACACAATAATCGGCAATTTGTCCTGGACAGGCACGGCAGTTTATCCCCGCTGGCGCGG
GGAACACGAATCTGGAGGCCAACAGCGCGGCGAAATCCTCAGTTTATCCCCGCTGGCGCGGGGAA
CACACTAAACGTATGTCATTGTTTATAAACTACTTTTTATCAGCACCACATTCCACCAACATAATCG
CAACAATTTAAATTATTAAAGAACAGCTAATTTGCTGATTTTGATGCAAAAAAGTTCATAGAATGA
TTTTTTCTTTAAATTTACCAAAATAGCGCGATCCGTGCATCGCTATGGAAAAATTTATCAGCGCTTT
TATACACTCATCGAAATTCACATAGAGAAAATAAACAATGCAAGGTAATGGATGAGTCACAGACG
GCAT

FIGURE 7

CGGGAGTGAGCGCCGTGCCGCGAGTAGTGCGGATAATGCTGCCGTTGGTAAAAGAGCTGGCGAAG
GCGGAAAAAACGTCCTGATATGCTGGTGAAACGTGTTTATCCCCGCTGGCGCGGGGAACATTTTTC
AGCCCTTGTCGACTGCGGAACGCCCCTCGGTTTATCCCCGCTGGCGCGGGGAACACGCGAAATAGT
GGGGAAAAACCCCTGGTTAACCCGGTTTATCCCCGCTGGCGCGGGAAACACTAGGCCTTGATACC
ATCGCTCGCACCTCGTCACGGTTTATCCCCGCTGGCGCGGGGAACACGTTTATTACTGCTTAGTTA
ATTAATGGGTTGCCGGTTTATCCCCGCTGGCGCGGGGAACACAGGCGAATAATCTCTAATAGTCTC
AATTCGTTCGGTTTATCCCCGCTGGCGCGGGGAACACTAAATCTGGCGTCGAGACATTCGAAATAG
TGCCGGTTTATCCCCGCTGGCGCGGGGAACACTCTTTTGATTTTGCTGCGATGTTATAACCAGACG
GTTTATCCCCGCTGGCGCGGGGAACACTATCCACATATACCCGCAATCATATTCAAGAACGGTTTA
TCCCCGCTGGCGCGGGGAACACAATCACTGCGGGGTATTTAGCGGAAACGGCTCGGTTTATCCCC
GCTGGCGCGGGGAACACCAGCACGAAAAATTATTTACTGTCGTTGCTCACGGTTTATCCCCGCTGG
CGCGGGAACACACTAAAACTATATATTTGTTCTAAAAGCCCTTTTTTACTACATAACAACTACCA
ACGGTAGATAACAATTCCTTATTATTAAAGACATTCAACTTATTGATTTTCAACAGGAAGAAAAGA
AACCCAAACGCAGTCCATCCAAA

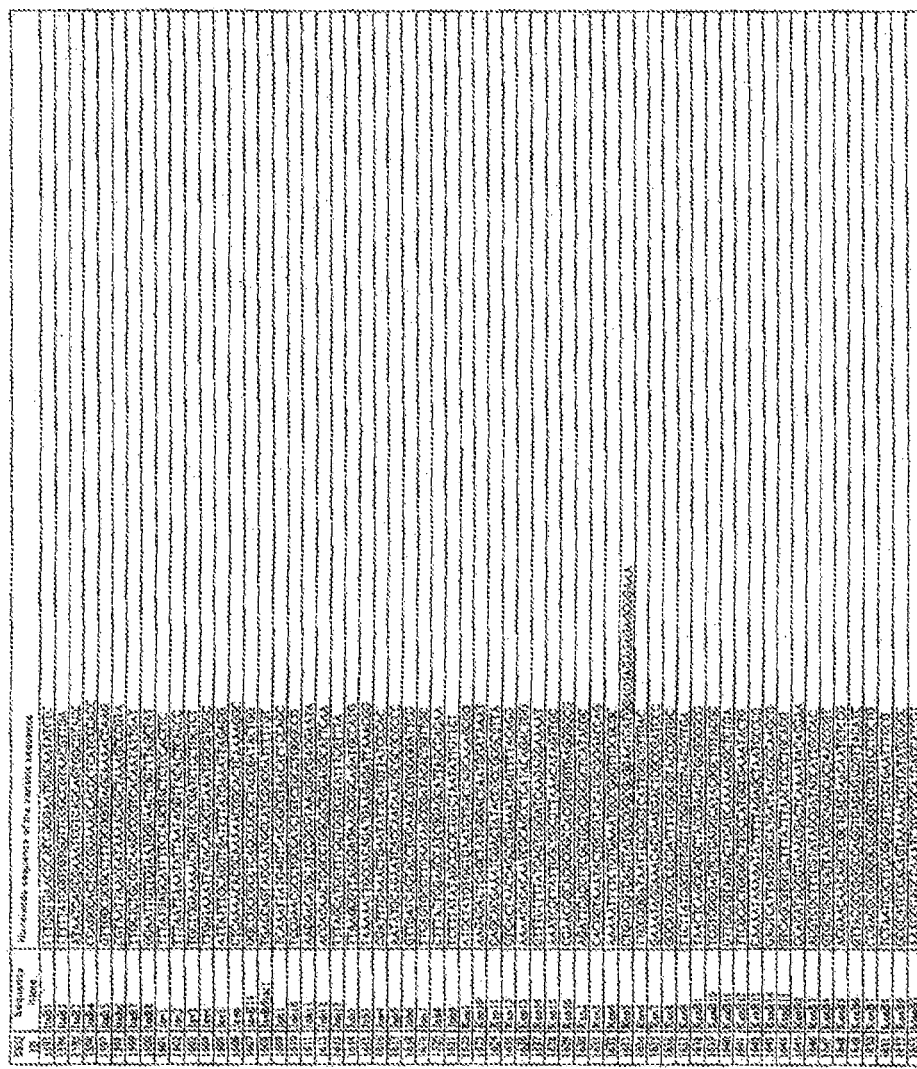

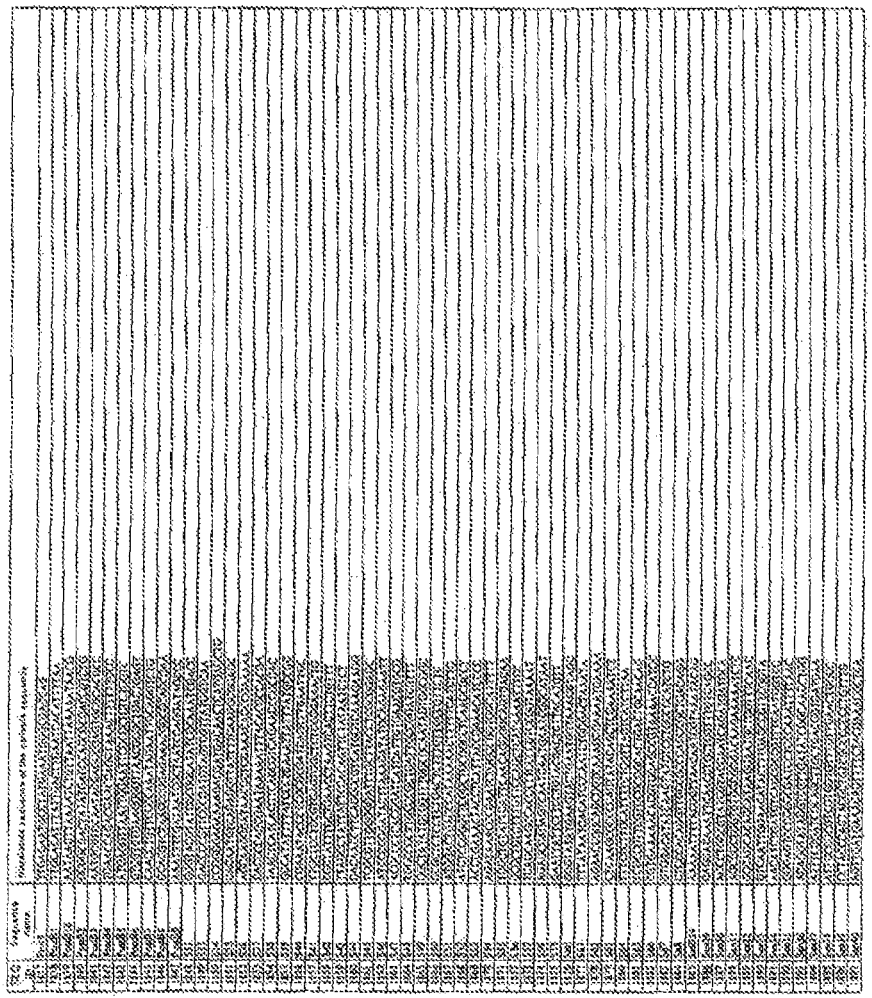

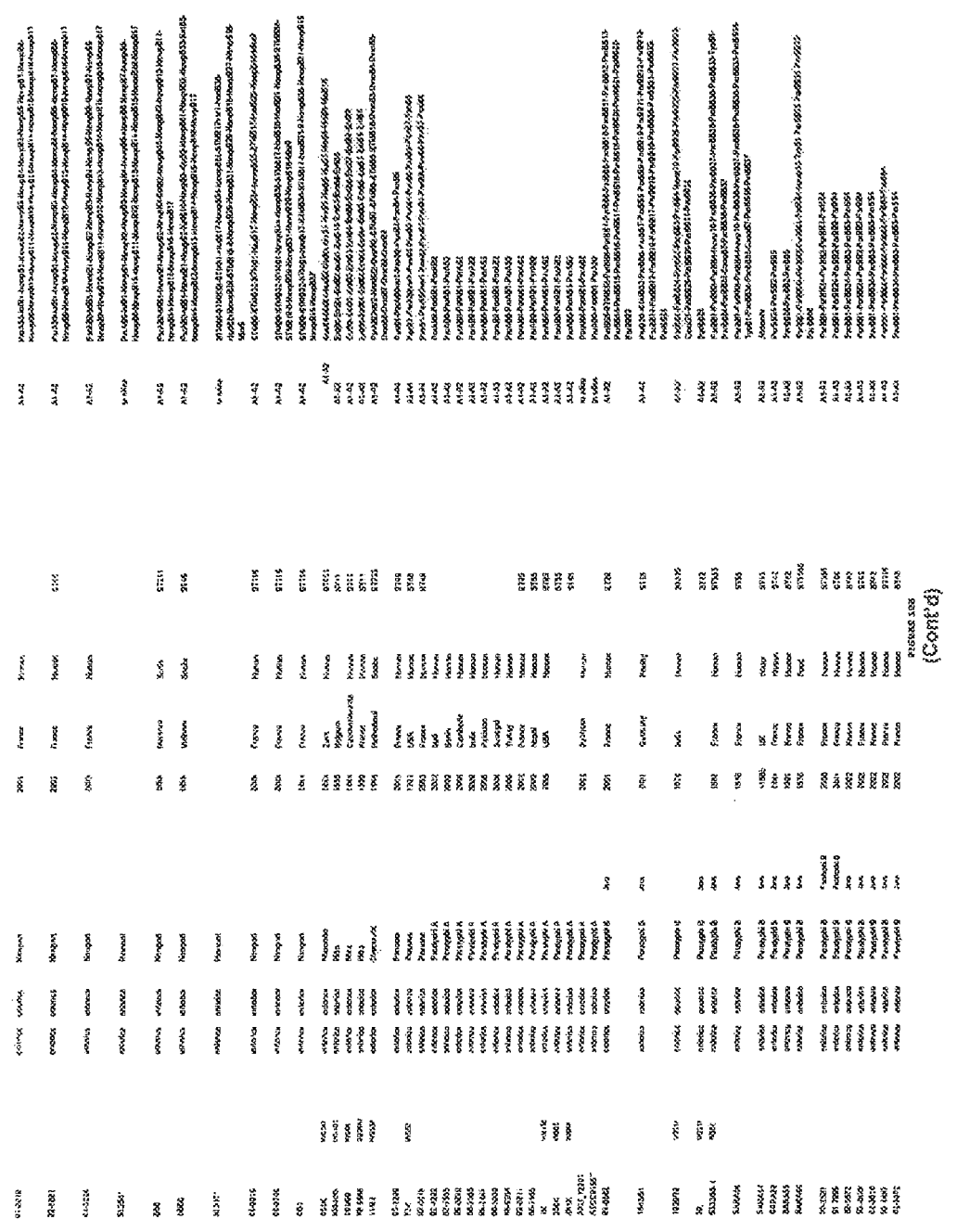

MOLECULAR TYPING AND SUBTYPING OF SALMONELLA BY IDENTIFICATION OF THE VARIABLE NUCLEOTIDE SEQUENCES OF THE CRISPR LOCI

SEQUENCE LISTING

The instant application contains a "lengthy" Sequence Listing which has been submitted via CD-R in lieu of a printed paper copy, and is hereby incorporated by reference in its entirety. Said CD-R, recorded on Nov. 15, 2011, are labeled CRF, "Copy 1" and "Copy 2", respectively, and each contains only one identical 533,358 bytes file (03495044.txt).

The present invention relates to the detection and identification of bacteria of the *Salmonella* genus, and also to diagnostic reagents, such as oligonucleotide primers and probes, for molecular typing and subtyping of these bacteria.

Salmonelloses are the primary cause of bacterial diarrhea of food origin in industrialized countries. The Institut de Veille Sanitaire [French Institute for Public Health Surveillance] estimated in 2004 that 30 000 to 40 000 confirmed cases of salmonellosis lead to 100 to 500 deaths annually in France. Owing to a vast animal reservoir, animal and human salmonelloses also constitute a considerable economic cost for the food-processing industry. Testing for *Salmonella* is therefore carried out throughout the food chain, from the livestock to the final food product. In the event of a positive *Salmonella* sample, a more precise typing of the salmonella is carried out by serotyping.

*Salmonella* serotyping is currently based on the recognition of bacterial antigens (a wall antigen and one or two flagellar antigens) using a battery of polyclonal antibodies prepared in the rabbit. More than 2500 serotypes have already been described in *Salmonella*. Serotyping is a lengthy (approximately 3 to 6 days in order to obtain a result) and expensive (high cost of sera and considerable labor costs since it is a manual method) technique. In addition, in order to be able to serotype all the 2500 serotypes, it is necessary to be able to have approximately 200 rabbit sera (a large part of which are not commercially available). Serotyping is important not only in the medical field, since it makes it possible to detect epidemics, but also in the food sector since it makes it possible to trace the strains responsible for food contamination.

Moreover, owing to the predominance of certain *Salmonella* serotypes (Typhimurium and Enteridis represent by themselves 70% of the *Salmonella* detected in France each year), it is necessary to use more discriminating methods for tracing a particular strain belonging to these serotypes. These "subtyping" methods, which use, for example, pulse-field electrophoresis, phage typing, or a study by VNTR (acronym for "Variable Number of Tandem Repeats", Lindstedt et al., 2003, J. Clin. Microbiol. 14, 1469-1479), are laborious from a technical point of view and require several additional days of manipulation.

The presence of a family of repeat sequences of genomic DNA, called CRISPR (acronym for "Clustered Regularly Interspaced Short Palindromic Repeats") has been identified in many procaryotic organisms by Jansen et al. (2002, Mol. Microbiol. 43, 1565-1575). A CRISPR locus is characterized by noncontiguous repeat sequences (or DRs) generally of 21 to 37 base pairs (bp), separated by unique sequences, generally of 20 to 40 base pairs, called variable sequences (or alternatively spacers). The number of repeat sequences within a CRISPR locus, the number of CRISPR loci (1 to 2 *Salmonella*) or else the presence of CRISPR loci can vary within the same bacterial species (van Embden et al., 2000, J. Bacteriol. 182, 2393-2401).

The CRISPR loci have therefore been used to type bacterial strains by the technique called spoligotyping or "CRISPR locus spacer oligonucleotide typing" (Kamerbeek et al., 1997, J. Clin. Microbiol. 43, 907-914; Hoe et al., 1999, Emerg. Infect. Dis. 5, 254-263). This technique consists in amplifying the CRISPR locus by PCR using oligonucleotide primers complementary to genomic DNA regions located only in the repeat sequences (DR) of the CRISPR loci. The presence or absence of the variable sequences (spacers) in the amplification product is then determined using a DNA chip to which are attached probes capable of hybridizing to these variable sequences.

Molecular typing and subtyping by spoligotyping have thus been described for various bacterial species, such as *Mycobacterium tuberculosis* (Kamerbeek et al., 1997, mentioned above; Song et al., 2007, J. Microbiol. Methods, 68, 430-433) and *Corynebacterium diphtheriae* (Mokrousov et al., 2005, J. Clin. Microbiol. 43, 1662-1668).

The principle of a method for differentiating bacterial strains of the *Salmonella* genus by spoligotyping has been described in very general terms in international application WO 99/51771. However, this application does not disclose the nucleotide sequences of the variable sequences that can be used for detecting the various *Salmonella* types or subtypes.

Pourcel et al. (2005, Microbiology 151, 653-663) have, moreover, described a method of phylogenetic analysis of bacterial strains of the *Yersinia pestis* species based on the study of the polymorphism of the CRISPR loci of these strains. This method comprises the PCR amplification of the CRISPR loci of *Y. pestis* strains using oligonucleotide primers complementary to a genomic DNA sequence adjacent to the CRISPR loci of *Y. pestis* and *Y. pseudotuberculosis*, and then the analysis of the arrangement of the variable sequences contained in these loci.

The use of the spoligotyping technique has several drawbacks. This is because, given that regions of the repeat sequences of the CRISPR loci serve as complementary strand to which the oligonucleotide primers hybridize during the PCR reaction, the amplification product consequently contains a mixture of DNA fragments of different sizes comprising from one to all the variable sequences (spacers) of a CRISPR locus. As a result, the identification of the order of the spacers and of the presence of new spacers in a CRISPR locus cannot be carried out by this method since the sequencing of this mixture of amplified DNA fragments proves to be impossible. In addition, since the oligonucleotide primers are specific for a repeat sequence of a given serotype, it is not only necessary to have several pairs of primers for identifying various serotypes, but also impossible to detect, by hybridization, serotypes having repeat sequences different from those for which the primers were designed.

The present invention has given itself the aim of providing a method which meets practical needs more successfully than the prior art methods, in particular in that the molecular typing and/or subtyping of bacteria of the *Salmonella* genus are rapid and can be readily automated.

Thus, the inventors have designed oligonucleotide primers in such a way as to amplify, by PCR, fragments of the genomic sequence of various strains of *Salmonella*; these fragments comprise one of the two, or both, CRISPR loci. These primers do not hybridize to a region of the repeat sequences located inside the CRISPR loci, but hybridize to a genomic sequence located outside these loci. The inventors have subsequently sequenced the amplified DNA fragments so as to identify the various variable sequences (spacers) in each CRISPR locus and thus determine their variable-sequence compositions.

The inventors have thus analyzed 564 *Salmonella* strains belonging to 86 serotypes of the two species and six subspecies of *Salmonella* (as identified by conventional serotyping methods), including those which are found most commonly in humans and animals and in foods. These serotypes belong to the two species of *Salmonella*: *S. enterica* (and its six subspecies: *arizonae, diarizonae, enterica, houtenae, indica, salamae*) and *S. bongori*. On the basis of the CRISPR loci of these strains, the inventors have identified approximately 2150 different variable sequences, having an average size of 34 nucleotides.

Surprisingly, the inventors have observed that the presence (from 1 to 30 per CRISPR locus) or the absence of certain variable sequences and also their arrangement in the CRISPR loci were characteristic of a serotype. Similarly, when several strains of the same serotype were studied, the variable-sequence composition could vary between the strains (loss of certain variable sequences or acquisition of new variable sequences). The inventors have also shown that this variability within the same serotype was in agreement with the conventional methods of subtyping.

The subject of the present invention is therefore an in vitro method for molecular typing and/or subtyping of a bacterium of the *Salmonella* genus, using a sample, said method being characterized in that it comprises at least the following steps:

(a) amplifying a nucleic acid fragment from a bacterium of the *Salmonella* genus, said fragment comprising the CRISPR1 locus and/or the CRISPR2 locus, using at least one set of primers, which primers have a size of less than or equal to 50 nucleotides, said sets of primers being chosen from the group constituted of:

a set of primers "A" capable of amplifying a nucleic acid fragment comprising the CRISPR1 locus, comprising at least one forward primer A1 constituted of an oligonucleotide sequence which exhibits at least 70%, preferably 80%, 85%, 95%, more preferably 99% identity with, or which is identical to, a fragment of the genomic sequence of a bacterium of the *Salmonella* genus located in a region of 1000 by in a position 5' of the CRISPR1 locus, said fragment of the genomic sequence located in a position 5' of the CRISPR1 locus being of the same size as said primer A1, and at least one reverse primer A2 constituted of an oligonucleotide sequence which exhibits 70%, preferably 80%, 85%, 95%, more preferably 99% identity with, or which is identical to, a fragment of the genomic sequence complementary to the genomic sequence of a bacterium of the *Salmonella* genus located in a position 3' of the CRISPR1 locus and in a position 5' of the CRISPR2 locus, preferably in a region of 1000 by in a position 3' of the CRISPR1 locus, said fragment of the complementary genomic sequence being of the same size as said primer A2;

a set of primers "B" capable of amplifying a nucleic acid fragment comprising the CRISPR2 locus, comprising at least one forward primer B1 constituted of an oligonucleotide sequence which exhibits at least 70%, preferably 80%, 85%, 95%, more preferably 99% identity with, or which is identical to, a fragment of the genomic sequence of a bacterium of the *Salmonella* genus located in a position 3' of the CRISPR1 locus and in a position 5' of the CRISPR2 locus, preferably in a region of 1000 by in a position 5' of the CRISPR2 locus, said fragment of the genomic sequence located in a position 3' of the CRISPR1 locus and in a position 5' of the CRISPR2 locus being of the same size as said primer B1, and at least one reverse primer B2 constituted of an oligonucleotide sequence which exhibits at least 70%, preferably 80%, 85%, 95%, more preferably 99% identity with, or which is identical to, a fragment of the genomic sequence complementary to the genomic sequence of a bacterium of the *Salmonella* genus located in a region of 1000 by in a position 3' of the CRISPR2 locus, said fragment of the complementary genomic sequence being of the same size as said primer B2;

a set of primers "C" capable of amplifying a nucleic acid fragment comprising the CRISPR1 locus and the CRISPR2 locus, comprising at least one forward primer A1 as defined above and at least one reverse primer B2 as defined above;

(b) determining the variable-sequence composition of the CRISPR1 locus and/or of the CRISPR2 locus included in the nucleic acid fragments amplified in step (a); and (c) comparing said variable-sequence composition of the CRISPR1 and/or CRISPR2 loci with a reference base which provides the variable-sequence composition of the CRISPR1 and CRISPR2 loci of types and subtypes of bacteria of the *Salmonella* genus, listed in FIGS. 10 and 9, or a part of this base.

The term "molecular typing" is intended to mean determining the serotype (or serovar) of a bacterium of the *Salmonella* genus belonging to the two species and six subspecies as described above, by characterization of a part of its genome (i.e. the CRISPR1 and/or CRISPR2 loci).

The term "molecular subtyping" is intended to mean determining the subtype of a bacterial strain belonging to a given *Salmonella* serotype, by characterization of a part of its genome (i.e. the CRISPR1 and/or CRISPR2 loci). The identification of the subtype of a bacterial strain of *Salmonella* is important, for example, for recognizing the foci of infection, detecting a cross transmission of *Salmonella*, determining the source of the infection or recognizing more particularly the virulent strains of *Salmonella*.

The term "CRISPR locus" is intended to mean a genomic DNA sequence composed of a series of repeat nucleotide sequences (called DR) having a size of approximately 21 to 37 base pairs, spaced out by variable nucleotide sequences (spacers) having a size of approximately 20 to 40 base pairs. The bacteria of the *Salmonella* genus have one or two CRISPR loci. The following table 1 shows the location of the CRISPR1 and CRISPR2 loci of some strains of bacteria of the *Salmonella* genus:

| Strains and accession numbers in the GenBank database referencing the genome of the strains | Location of the CRISPR1 locus in the genome of the bacteria, with reference to the accession number in the GenBank database | Location of the CRISPR2 locus in the genome of the bacteria, with reference to the accession number in the GenBank database |
| --- | --- | --- |
| *S. enterica* subsp *enterica* serotype: | | |
| Typhimurium strain LT2 AE008834 (GI: 16421485) and AE008835 (GI: 16421501), of Aug. 9, 2005 | nucleotides 1183-2719 | nucleotides 18852 (AE008834)-863 (AE008835) |

| Strains and accession numbers in the GenBank database referencing the genome of the strains | Location of the CRISPR1 locus in the genome of the bacteria, with reference to the accession number in the GenBank database | Location of the CRISPR2 locus in the genome of the bacteria, with reference to the accession number in the GenBank database |
|---|---|---|
| Typhi strain CT18 AL627276 (of Nov. 14, 2006; GI: 16503805) | nucleotides 224182-224567 | nucleotides 241124-241212 |
| Typhi strain Ty2 AE014613 (of Jan. 17, 2006; GI: 29140506) | nucleotides 2912041-2912461 | nucleotides 2929018-2929106 |
| Paratyphi A strain ATCC 9150 CP000026 (of Apr. 8, 2005; GI: 56126533) | nucleotides 2889569-2889902 | nucleotides 2906454-2906664 |
| Paratyphi A strain AKU_12601 FM200053 (of Oct. 23, 2008; GI: 197092687) | nucleotides 2885105-2885559 | nucleotides 2902112-2902322 |
| Enteritidis strain P225109 AM933172 (of Oct. 23, 2008; GI: 206707319) | nucleotides 2961370-2961886 | nucleotides 2978039-2978677 |
| Gallinarum strain 287/91 AM933173 (of Oct. 8, 2008; GI: 205271127) | nucleotides 2952175-2952327 | nucleotides 2968479-2969117 |
| Dublin strain CT_02021853 CP001144 (of Sep. 5, 2008; GI: 197936256) | nucleotides 3121101-3121251 | nucleotides 3137410-33137742 |
| Choleraesuis strain SC-B67 AE017220 (of Jan. 11, 2006; GI: 62126203) | nucleotides 3031533-3031805 | nucleotides 3049245-3049698 |
| Newport strain SL254 CP001113 (of Jul. 25, 2008; GI: 194400866 | nucleotides 3054859-3056473 | nucleotides 3073143-3074328 |
| Agona strain SL483 CP001138 (of Aug. 22, 2008; GI: 197211055) | nucleotides 2988105 to 2989231 | nucleotides 3005518 to 006033 |
| Heidelberg strain SL476 CP001120 (of Jul. 25, 2008; GI: 194405610) | nucleotides 3051217-3052879 | nucleotides 3069138-3070263 |
| Schwarzengrund strain CVM19633 CP001127 (of Jul. 30, 2008; GI: 194709404) | nucleotides 2981949-2982709 | nucleotides 2999470-3000534 |
| Paratyphi B strain SPB7 CP000886 (of Jan. 15, 2008; GI: 161361677) | nucleotides 3041329-3041479 | nucleotides 3050805-3051137 |
| *S. enterica* subsp *arizonae* serotype: | | |
| 62:z4,z23:- strain CDC346-86 CP000880 (of Jan. 15, 2008; GI: 160863331) | nucleotides 25560-25471 | nucleotides 17801-1773 |

In the context of the disclosure of the present invention, the CRISPR1 locus is defined as being located in a position 5' with respect to the CRISPR2 locus.

Unless otherwise specified, the identity percentages indicated in the context of the disclosure of the present invention are calculated over a window of comparison constituted of the entire sequence of the primer as reference sequence. The percentage of identical nucleotides can be calculated by those skilled in the art using a sequence comparison computer program.

The reference base according to the present invention indicates the variable-sequence composition of the CRISPR1 and/or CRISPR2 loci of the 564 *Salmonella* strains analyzed by the inventors or of a part of these strains. Said reference base includes in particular the *Salmonella* strains of clinical and food-product interest currently known. Of course, the variable-sequence composition of new *Salmonella* bacterial strains can be added to said reference base.

Advantageously, the method according to the present invention makes it possible not only to obtain a genomic DNA fragment comprising the whole of one or of the two CRISPR loci of a bacterium of the *Salmonella* genus, so as to determine the variable-sequence composition of these loci in order to be able to compare it with said reference base and thus determine the molecular type and/or subtype of the bacterium, but also to identify new *Salmonella* strains by determining the variable-sequence composition of these CRISPR loci.

The identity of the variable-sequence composition determined in step (b) of the method according to the invention with respect to a composition appearing in said reference base is thus indicative of the type and/or subtype of the bacterium of the *Salmonella* genus present in the sample.

The expression "determining the variable-sequence composition of the CRISPR1 locus and/or of the CRISPR2 locus" is intended to mean determining the number, the nucleotide sequence and, optionally, the order of the spacers in the CRISPR1 and/or CRISPR2 locus of *Salmonella*.

In one particular embodiment, the bacteria of the *Salmonella* genus for which the molecular typing and/or subtyping method according to the invention is carried out are chosen from the group constituted of:

i) the species *S. enterica*
    subspecies *enterica*; in particular the serotypes Abony, Abortusequi, Aesch, Agona, Albany, Altona, Anatum, Arechavalata, Bardo, Berta, Bispebjerg, Blegdam, Bovismorbificans, Brandenburg, Chester, Choleraesuis variety Decatur, Choleraesuis, Choleraesuis variety Kunzendorf, Choleraesuis sensu stricto, Concord, Crossness, Derby, Dublin, Duesseldorf, Emek, Enteritidis, Fulica, Gallinarum variety Duisburg, Gallinarum variety Gallinarum, Gallinarum variety Pullorum, Goettingen, Gueuletapee, Hadar, Heidelberg, Hessarek, Indiana, Infantis, Itami, Javiana, Johannesburg, Kentucky, Kiel, Kottbus, Kundunchi, Lindenburg, Manhattan, Maracaibo, Mbandaka, Miami, Mississippi, Montevideo, Muenchen, Napoli, Newport, Niarembe, Nitra, Overvecht, Panama, Paratyphi A, Paratyphi B, Paratyphi C, Poona, Potsdam, Reading, Rosenberg, Rubislaw, Saintpaul, Sandiego, Schwarzengrund, Sendai, Senftenberg, Stourbridge, Tallahassee, Tennessee, Typhi, Typhimurium, Typhisuis, Urbana, Virchow, Weltevreden, Zaiman, subspecies *salamae*; in particular the serotypes 11:1,z28: e,n,x; 57:z42:1,6:Rz53;

subspecies *arizonae*; in particular the serotypes 62:z4, z23:–; 53:g,z51:–; 56:z4,z23:–; 17:z29:–;

subspecies *diarizonae*; in particular the serotypes 38:z10: z53; 61:1,v:1,5,7;

subspecies *houtenae*; in particular the serotypes 6,7:z4, z24:–; 44:a:–; 1,40:z4,z24:–;

subspecies *indica*; in particular the serotypes 11:b:1,7; 6,7: z41:1,7;

ii) the species bongori; in particular the serotypes 60:z41:–; 66:z35:–; 48:z35:–; 66:z41:–.

The terms "nucleic acid" and "DNA" are equivalent and comprise single-stranded or double-stranded nucleic acids.

According to one advantageous embodiment of the method in accordance with the invention, the nucleic acid fragment to be amplified in step (a) above has a size of between 400 and 20 000 bp.

According to one embodiment of the method in accordance with the present invention, said amplification can be carried out by any method known to those skilled in the art. Preferably, the amplification can be carried out by a method selected from the group consisting of: polymerase chain reaction (PCR), ligase chain reaction (LCR), nucleic acid sequence-based amplification (NASBA), cycling probe technology (CPT), nested PCR and multiplex PCR.

According to one advantageous embodiment of the method in accordance with the invention, said fragment of the genomic sequence of a bacterium of the *Salmonella* genus located in a position 5' of the CRISPR1 locus, and/or said fragment of the genomic sequence complementary to the genomic sequence of a bacterium of the *Salmonella* genus located in a position 3' of the CRISPR2 locus, is(are) located at a distance from the CRISPR1 or CRISPR2 locus of less than 500 bp, preferably less than 100 bp.

The term "primer" denotes a single-stranded or double-stranded oligonucleotide, preferably a single-stranded oligonucleotide for optimal efficiency. A primer (an oligonucleotide primer), once hybridized to a single-stranded nucleic acid sequence, termed "template", is a substrate for at least one DNA polymerase (i.e. a primer hybridized to a nucleic acid sequence has the property of binding, at its 3'OH end, at least one DNA polymerase). In the presence of appropriate nucleotides (A, C, G, T), of a DNA polymerase (for example, the Taq polymerase), of an appropriate buffer (comprising cofactors or compounds affecting the pH or the ionic strength of the reaction medium, for example) and at an appropriate temperature, the 3'OH end of a primer can be extended, thus resulting in the synthesis of a strand complementary to the template sequence to which said primer is hybridized. The primers, according to the present invention, preferably have a length of less than or equal to 50 nucleotides, i.e. less than or equal to 40, 30, 20, 15 or 10 nucleotides. More preferably, the primers according to the present invention have a length of between 15 and 30 nucleotides, preferably between 18 and 25 nucleotides. The primers according to the present invention can be advantageously labeled.

For the purpose of the present invention, two nucleic acid molecules are "complementary" when each of the bases in successive positions of the 5' end of the first nucleic acid molecule is paired with the corresponding residue in the second molecule, starting from the 3' end, according to the rules of base-pair pairing (i.e. A and T, C and G). Under suitable conditions known to those skilled in the art, two complementary single strands of DNA reassociate to form a double-stranded DNA molecule.

According to one particular embodiment, the set of primers for amplifying the nucleic acid fragment comprising the CRISPR1 locus and/or the CRISPR2 locus is selected from the group constituted of:

the set of primers, capable of amplifying the CRISPR1 locus, constituted of the primer of sequence SEQ ID No.: 1326 (SALCRISP1-FB) combined with at least one of the primers of sequence SEQ ID Nos: 1327 (SALCRISP1-RB), 1328 (AriParaB-R), 1329 (BrPanCR1-R), 2151 (50K) and 2152 (HoutWS24R), the set of primers, capable of amplifying the CRISPR2 locus, constituted of the primer of sequence SEQ ID No.: 1330 (SALCRISP2-FB), combined with at least one of the primers of sequence SEQ ID Nos: 1331 (SALCRISP2-RA) and 1332 (SALCRISP2-RB), and the set of primers, capable of simultaneously amplifying the two loci CRISPR1 and CRISPR2, constituted of the primer of sequence SEQ ID No.: 1326, combined with at least one of the two primers of sequences 1331 and 1332 (the primers of sequence SEQ ID Nos: 1326 and 1331 being located at least 100 by from the CRISPR1 and CRISPR2 loci respectively, and the primer of sequence SEQ ID No.: 1332 being located at least 500 by from the CRISPR2 locus).

Consequently, the subject of the present invention is also a set of primers, as defined above, capable of amplifying a fragment of the genomic sequence of a bacterium of the *Salmonella* genus.

In one particular embodiment according to the invention, the forward primer A 1 is constituted of an oligonucleotide sequence which exhibits at least 70%, preferably 80%, 85%, 95%, more preferably 99% identity with, or which is identical to, a fragment of the genomic sequence of *S. enterica* serotype Typhimurium LT2 or of *S. enterica* serotype Typhi CT18, located in a region of 1000 by in a position 5' of the CRISPR1 locus (for example, for the LT2 strain, the region corresponding to nucleotides 183 to 1183 of the genomic sequence available under number AE008834 (GI: 16421485)), said fragment of the genomic sequence located in a position 5' of the CRISPR1 locus being of the same size as said primer A1.

In one particular embodiment according to the invention, the reverse primer A2 is constituted of an oligonucleotide sequence which exhibits 70%, preferably 80%, 85%, 95%, more preferably 99% identity with, or which is identical to, a fragment of the genomic sequence complementary to the genomic sequence of *S. enterica* serotype Typhimurium LT2 or of *S. enterica* serotype Typhi CT18, which is located in a position 3' of the CRISPR1 locus and in a position 5' of the CRISPR2 locus (for example, for the LT2 strain, the region corresponding to nucleotides 2727 to 18836, preferably 2727 to 3727, of the genomic sequence available under number AE008834 (GI: 16421485)), said fragment being of the same size as said primer A2.

In one particular embodiment according to the invention, the forward primer B1 is constituted of an oligonucleotide sequence which exhibits at least 70%, preferably 80%, 85%, 95%, more preferably 99% identity with, or which is identical to, a fragment of the genomic sequence of *S. enterica* serotype Typhimurium LT2 or of *S. enterica* serotype Typhi CT18, which is located in a position 3' of the CRISPR1 locus and in a position 5' of the CRISPR2 locus (for example, for the LT2 strain, the region corresponding to nucleotides 2727 to 18836, preferably 17836 to 18836, of the genomic sequence available under number AE008834 (GI: 16421485)), said fragment of the genomic sequence located in a position 3' of the CRISPR1 locus and in a position 5' of the CRISPR2 locus being of the same size as said primer.

In one particular embodiment according to the invention, the reverse primer B2 is constituted of an oligonucleotide sequence which has at least 70%, preferably 80%, 85%, 95%, more preferably 99% identity with, or which is identical to, a fragment of the genomic sequence complementary to the genomic sequence of *S. enterica* serotype Typhimurium LT2 or of *S. enterica* serotype Typhi CT18, which is located in a region of 1000 by in a position 3' of the CRISPR2 locus (for example, for the LT2 strain, the region corresponding to nucleotides 862 to 1862 of the genomic sequence available under number AE008835 (GI: 16421501)), said complementary genomic sequence fragment being of the same size as said primer.

According to one advantageous embodiment of the method in accordance with the invention, step (b) described above is carried out by means of a DNA sequencing method. By way of example, the sequencing can be carried out by the Sanger method or the Maxam and Gilbert method, which are methods well known to those skilled in the art.

According to one advantageous embodiment of the method in accordance with the invention, step (b) described above is carried out by:

(i) hybridization of the amplification products with one, several or all the set(s) of probes, chosen from:

set S1-1, comprising or constituted of at least one probe comprising at least or constituted of at least 8 consecutive nucleotides of any one of the nucleic acid sequences SEQ ID Nos.: 1106 to 1119, 1123 to 1140, 1142, 1143, 1914 and/or the nucleic acid sequences complementary thereto (nucleotide sequences corresponding to the various variable sequences of the CRISPR1 locus of the serotype Typhimurium);

set S1-2, comprising or constituted of at least one probe comprising at least or constituted of at least 8 consecutive nucleotides of any one of the nucleic acid sequences SEQ ID Nos.: 455, 1144 to 1153, 1155 to 1181 and/or the nucleic acid sequences complementary thereto (nucleotide sequences corresponding to the various variable sequences of the CRISPR2 locus of the serotype Typhimurium);

set S2-1, comprising or constituted of at least one probe comprising at least or constituted of at least 8 consecutive nucleotides of any one of the nucleic acid sequences SEQ ID Nos.: 256, 378 to 381, 383 to 387, 389 to 391, 1106, 1514, 1528, 2148 to 2153 and/or the nucleic acid sequences complementary thereto (nucleotide sequences corresponding to the various variable sequences of the CRISPR1 locus of the serotype Enteritidis);

set S2-2, comprising or constituted of at least one probe comprising at least or constituted of at least 8 consecutive nucleotides of any one of the nucleic acid sequences SEQ ID Nos.: 392 to 413, 519, 815, 972, 983, 989, 1529 to 1546, 1952 and/or the nucleic acid sequences complementary thereto (nucleotide sequences corresponding to the various variable sequences of the CRISPR2 locus of the serotype Enteritidis);

set S3-1, comprising or constituted of at least one probe comprising at least or constituted of at least 8 consecutive nucleotides of any one of the nucleic acid sequences SEQ ID Nos.: 421 to 442, 444, 445, 447 to 450 and/or the nucleic acid sequences complementary thereto (nucleotide sequences corresponding to the various variable sequences of the CRISPR1 locus of the serotype Hadar);

set S3-2, comprising or constituted of at least one probe comprising at least or constituted of at least 8 consecutive nucleotides of any one of the nucleic acid sequences SEQ ID Nos.: 451 to 465, 1144 to 1147, 1150 to 1152, 1154, 1155, 1158, 1169, 1172, 1175 to 1177, 1179, 1181 and/or the nucleic acid sequences complementary thereto (nucleotide sequences corresponding to the various variable sequences of the CRISPR2 locus of the serotype Hadar);

set S4-1, comprising or constituted of at least one probe comprising at least or constituted of at least 8 consecutive nucleotides of any one of the nucleic acid sequences SEQ ID Nos.: 65, 382, 1120, 1263 to 1302, 2024 to 2038 and/or the nucleic acid sequences complementary thereto (nucleotide sequences corresponding to the various variable sequences of the CRISPR1 locus of the serotype Virchow);

set S4-2, comprising or constituted of at least one probe comprising at least or constituted of at least 8 consecutive nucleotides of any one of the nucleic acid sequences SEQ ID Nos.: 83, 93, 94, 1304 to 1324 and/or the nucleic acid sequences complementary thereto (nucleotide sequences corresponding to the various variable sequences of the CRISPR2 locus of the serotype Virchow);

set S5-1, comprising or constituted of at least one probe comprising at least or constituted of at least 8 consecutive nucleotides of any one of the nucleic acid sequences SEQ ID Nos.: 531 to 562, 1106 and/or the nucleic acid sequences complementary thereto (nucleotide sequences corresponding to the various variable sequences of the CRISPR1 locus of the serotype Infantis);

set S5-2, comprising or constituted of at least one probe comprising at least or constituted of at least 8 consecutive nucleotides of any one of the nucleic acid sequences SEQ ID Nos.: 563 to 588 and/or the nucleic acid sequences complementary thereto (nucleotide sequences corresponding to the various variable sequences of the CRISPR2 locus of the serotype Infantis);

set S6-1, comprising or constituted of at least one probe comprising at least or constituted of at least 8 consecutive nucleotides of any one of the nucleic acid sequences SEQ ID Nos.: 1254 to 1259 and/or the nucleic acid sequences complementary thereto (nucleotide sequences corresponding to the various variable sequences of the CRISPR1 locus of the serotype Typhi);

set S6-2, comprising or constituted of at least one probe comprising at least or constituted of at least 8 consecutive nucleotides of the nucleic acid sequence SEQ ID No.: 1260 and/or the nucleic acid sequence complementary thereto (nucleotide sequences corresponding to the variable sequence of the CRISPR2 locus of the serotype Typhi);

set S7-1, comprising or constituted of at least one probe comprising at least or constituted of at least 8 consecutive nucleotides of any one of the nucleic acid sequences SEQ ID Nos: 448, 449, 860 to 884, 1719 to 1724, 1727 to 1743, 1745 and/or the nucleic acid sequences complementary thereto (nucleotide sequences corresponding to the various variable sequences of the CRISPR1 locus of the serotype Newport);

set S7-2, comprising or constituted of at least one probe comprising at least or constituted of at least 8 consecutive nucleotides of any one of the nucleic acid sequences SEQ ID Nos: 453 to 456, 563, 621, 622, 625, 626, 657, 885 to 896, 906 to 915, 933, 1144, 1145, 1155, 1156, 1172, 1174, 1748 to 1756, 1758, 1759, 1916 and/or the nucleic acid sequences complementary thereto (nucleotide sequences corresponding to the various variable sequences of the CRISPR2 locus of the serotype Newport);

set S8-1, comprising or constituted of at least one probe comprising at least or constituted of at least 8 consecutive nucleotides of any one of the nucleic acid sequences SEQ ID Nos: 295 to 299, 301 to 323, 738, 1106 to 1109, 1120, 1123, 1128 to 1131, 1133, 1137 to 1140, 1550, 1159 to 1561 and/or the nucleic acid sequences complementary thereto (nucleotide sequences corresponding to the various variable sequences of the CRISPR1 locus of the serotype Derby);

set S8-2, comprising or constituted of at least one probe comprising at least or constituted of at least 8 consecutive nucleotides of any one of the nucleic acid sequences SEQ ID Nos: 324 to 337, 455, 1144, 1145, 1149 to 1153, 1155 to 1160, 1163, 1172 to 1174 and/or the nucleic acid sequences complementary thereto (nucleotide sequences corresponding to the various variable sequences of the CRISPR2 locus of the serotype Derby);

set S9-1, comprising or constituted of at least one probe comprising at least or constituted of at least 8 consecutive nucleotides of any one of the nucleic acid sequences SEQ ID Nos: 295, 307, 602 to 614, 616 to 619, 1106, 1120 and/or the nucleic acid sequences complementary thereto (nucleotide sequences corresponding to the various variable sequences of the CRISPR1 locus of the serotype Kottbus);

set S9-2, comprising or constituted of at least one probe comprising at least or constituted of at least 8 consecutive nucleotides of any one of the nucleic acid sequences SEQ ID Nos: 563, 620 to 629, 885, 896, 907, 913, 914, 933 and/or the nucleic acid sequences complementary thereto (nucleotide sequences corresponding to the various variable sequences of the CRISPR2 locus of the serotype Kottbus);

set S10-1, comprising or constituted of at least one probe comprising at least or constituted of at least 8 consecutive nucleotides of any one of the nucleic acid sequences SEQ ID Nos: 422 to 425, 448 to 450, 504 to 518 and/or the nucleic acid sequences complementary thereto (nucleotide sequences corresponding to the various variable sequences of the CRISPR1 locus of the serotype Indiana);

set S10-2, comprising or constituted of at least one probe comprising at least or constituted of at least 8 consecutive nucleotides of any one of the nucleic acid sequences SEQ ID Nos: 246, 258, 269, 392, 415, 519 to 530 and/or the nucleic acid sequences complementary thereto (nucleotide sequences corresponding to the various variable sequences of the CRISPR2 locus of the serotype Indiana);

set S11-1, comprising or constituted of at least one probe comprising at least or constituted of at least 8 consecutive nucleotides of any one of the nucleic acid sequences SEQ ID Nos: 11 to 23, 238, 948, 1120, 1123, 1133 and/or the nucleic acid sequences complementary thereto (nucleotide sequences corresponding to the various variable sequences of the CRISPR1 locus of the serotype Agona);

set S11-2, comprising or constituted of at least one probe comprising at least or constituted of at least 8 consecutive nucleotides of any one of the nucleic acid sequences SEQ ID Nos: 24 to 31 and/or the nucleic acid sequences complementary thereto (nucleotide sequences corresponding to the various variable sequences of the CRISPR2 locus of the serotype Agona);

set S12-1, comprising or constituted of at least one probe comprising at least or constituted of at least 8 consecutive nucleotides of any one of the nucleic acid sequences SEQ ID Nos: 830 to 841, 1120 and/or the nucleic acid sequences complementary thereto (nucleotide sequences corresponding to the various variable sequences of the CRISPR1 locus of the serotype Napoli);

set S12-2, comprising or constituted of at least one probe comprising at least or constituted of at least 8 consecutive nucleotides of any one of the nucleic acid sequences SEQ ID Nos: 842 to 859 and/or the nucleic acid sequences complementary thereto (nucleotide sequences corresponding to the various variable sequences of the CRISPR2 locus of the serotype Napoli);

set S13-1, comprising or constituted of at least one probe comprising at least or constituted of at least 8 consecutive nucleotides of any one of the nucleic acid sequences SEQ ID Nos: 926 to 932 and/or the nucleic acid sequences complementary thereto (nucleotide sequences corresponding to the various variable sequences of the CRISPR1 locus of the serotype Paratyphi A);

set S13-2, comprising or constituted of at least one probe comprising at least or constituted of at least 8 consecutive nucleotides of any one of the nucleic acid sequences SEQ ID Nos: 933, 935, 936 and/or the nucleic acid sequences complementary thereto (nucleotide sequences corresponding to the various variable sequences of the CRISPR2 locus of the serotype Paratyphi A);

set S14-1, comprising or constituted of at least one probe comprising at least or constituted of at least 8 consecutive nucleotides of any one of the nucleic acid sequences SEQ ID Nos: 707, 937 to 971, 1106, 1128 to 1130, 1133, 1138, 1140, 1802 to 1808, 1915 and/or the nucleic acid sequences complementary thereto (nucleotide sequences corresponding to the various variable sequences of the CRISPR1 locus of the serotypes Paratyphi B and Paratyphi B Java);

set S14-2, comprising or constituted of at least one probe comprising at least or constituted of at least 8 consecutive nucleotides of any one of the nucleic acid sequences SEQ ID Nos: 861, 972 to 987, 989 to 992 996, 1172, 1262, 1462, 1497, 1810 to 1825 and/or the nucleic acid sequences complementary thereto (nucleotide sequences corresponding to the various variable sequences of the CRISPR2 locus of the serotypes Paratyphi B and Paratyphi B Java);

set S15-1, comprising or constituted of at least one probe comprising at least or constituted of at least 8 consecutive nucleotides of any one of the nucleic acid sequences SEQ ID Nos: 232, 238, 239, 997 to 1002, 1106 and/or the nucleic acid sequences complementary thereto (nucleotide sequences corresponding to the various variable sequences of the CRISPR1 locus of the serotype Paratyphi C);

set S15-2, comprising or constituted of at least one probe comprising at least or constituted of at least 8 consecutive nucleotides of any one of the nucleic acid sequences SEQ ID Nos: 280, 290, 291, 392, 393, 415, 1003 to 1006, 1262 and/or the nucleic acid sequences complementary thereto (nucleotide sequences corresponding to the various variable sequences of the CRISPR2 locus of the serotype Paratyphi C);

set S16-1, comprising or constituted of at least one probe comprising at least or constituted of at least 8 consecutive nucleotides of any one of the nucleic acid sequences SEQ ID Nos: 211 to 224, 421, 427, 428, 432, 443 to 445, 447 to 449, 504 and/or the nucleic acid sequences complementary thereto (nucleotide sequences corresponding to the various variable sequences of the CRISPR1 locus of the serotype Bovismorbificans);

set S16-2, comprising or constituted of at least one probe comprising at least or constituted of at least 8 consecutive nucleotides of any one of the nucleic acid sequences SEQ ID Nos: 196 to 209, 994, 1144, 1145, 1172 and/or the nucleic acid sequences complementary thereto (nucleotide sequences corresponding to the various variable sequences of the CRISPR2 locus of the serotype Bovismorbificans);

set S17-1, comprising or constituted of at least one probe comprising at least or constituted of at least 8 consecutive nucleotides of the nucleic acid sequence SEQ ID No.: 916 and/or the nucleic acid sequence complementary thereto (nucleotide sequences corresponding to the variable sequences of the CRISPR1 locus of the serotype Panama);

set S17-2, comprising or constituted of at least one probe comprising at least or constituted of at least 8 consecutive nucleotides of any one of the nucleotide sequences SEQ ID Nos: 918 to 925, 934 and/or the nucleic acid sequences complementary thereto (nucleotide sequences corresponding to the various variable sequences of the CRISPR2 locus of the serotype Panama);

set S18-1, comprising or constituted of at least one probe comprising at least or constituted of at least 8 consecutive nucleotides of any one of the nucleotide sequences SEQ ID Nos: 11, 16, 67, 74, 442, 444, 446 to 448, 602, 937, 948, 1120, 1128 to 1130, 1182 to 1200, 1937 to 1950, and/or the nucleic acid sequences complementary thereto (nucleotide sequences corresponding to the various variable sequences of the CRISPR1 locus of the serotype Saintpaul);

set S18-2, comprising or constituted of at least one probe comprising at least or constituted of at least 8 consecutive nucleotides of any one of the nucleotide sequences SEQ ID Nos: 972, 983, 989, 1201 to 1214, 1216 to 1227, 1952 to 1960 and/or the nucleic acid sequences complementary thereto (nucleotide sequences corresponding to the various variable sequences of the CRISPR2 locus of the serotype Saintpaul);

set S19-1, comprising or constituted of at least one probe comprising at least or constituted of at least 8 consecutive nucleotides of any one of the nucleotide sequences SEQ ID Nos: 514, 1062 to 1089, 1100, 1284, 1886 to 1911 and/or the nucleic acid sequences complementary thereto (nucleotide sequences corresponding to the various variable sequences of the CRISPR1 locus of the serotype Senftenberg);

set S19-2, comprising or constituted of at least one probe comprising at least or constituted of at least 8 consecutive nucleotides of any one of the nucleotide sequences SEQ ID Nos: 300, 1090 to 1097, 1101 to 1103, 1304, 1315, 1318 to 1320 and/or the nucleic acid sequences complementary thereto (nucleotide sequences corresponding to the various variable sequences of the CRISPR2 locus of the serotype Senftenberg);

set S20-1, comprising or constituted of at least one probe comprising at least or constituted of at least 8 consecutive nucleotides of any one of the nucleotide sequences SEQ ID Nos: 67, 74 to 80 and/or the nucleic acid sequences complementary thereto (nucleotide sequences corresponding to the various variable sequences of the CRISPR1 locus of the serotype Anatum);

set S20-2, comprising or constituted of at least one probe comprising at least or constituted of at least 8 consecutive nucleotides of any one of the nucleotide sequences SEQ ID Nos: 83 to 94, 1304, 1315, 1318 to 1322, 1324, 1390 to 1397 and/or the nucleic acid sequences complementary thereto (nucleotide sequences corresponding to the various variable sequences of the CRISPR2 locus of the serotype Anatum);

set S21-1, comprising or constituted of at least one probe comprising at least or constituted of at least 8 consecutive nucleotides of any one of the nucleotide sequences SEQ ID Nos: 379, 383 to 385, 388 and/or the nucleic acid sequences complementary thereto (nucleotide sequences corresponding to the various variable sequences of the CRISPR1 locus of the serotypes Gallinarum);

set S21-2, comprising or constituted of at least one probe comprising at least or constituted of at least 8 consecutive nucleotides of any one of the nucleotide sequences SEQ ID Nos: 392, 393, 404, 407 to 415 and/or the nucleic acid sequences complementary thereto (nucleotide sequences corresponding to the various variable sequences of the CRISPR2 locus of the serotypes Gallinarum);

set S22-1, comprising or constituted of at least one probe comprising at least or constituted of at least 8 consecutive nucleotides of the nucleic acid sequence SEQ ID No.: 917 and/or the nucleic acid sequence complementary thereto (nucleotide sequences corresponding to the variable sequence of the CRISPR1 locus of the serotype Brandenburg);

set S22-2, comprising or constituted of at least one probe comprising at least or constituted of at least 8 consecutive nucleotides of any one of the nucleic acid sequences SEQ ID Nos: 225 to 231 and/or the nucleic acid sequences complementary thereto (nucleotide sequences corresponding to the various variable sequences of the CRISPR2 locus of the serotype Brandenburg);

set S23-1, comprising or constituted of at least one probe comprising at least or constituted of at least 8 consecutive nucleotides of any one of the nucleic acid sequences SEQ ID Nos: 378, 379 and/or the nucleic acid sequences complementary thereto (nucleotide sequences corresponding to the various variable sequences of the CRISPR1 locus of the serotype Dublin);

set S23-2, comprising or constituted of at least one probe comprising at least or constituted of at least 8 consecutive nucleotides of any one of the nucleic acid sequences SEQ ID Nos: 392, 393, 411, 412 and/or the nucleic acid sequences complementary thereto (nucleotide sequences corresponding to the various variable sequences of the CRISPR2 locus of the serotype Dublin);

set S24-1, comprising or constituted of at least one probe comprising at least or constituted of at least 8 consecutive nucleotides of any one of the nucleic acid sequences SEQ ID Nos: 1, 1106 and/or the nucleic acid sequences complementary thereto (nucleotide sequences corresponding to the various variable sequences of the CRISPR1 locus of the serotype Abortusequi);

set S24-2, comprising or constituted of at least one probe comprising at least or constituted of at least 8 consecutive nucleotides of any one of the nucleic acid sequences SEQ ID Nos: 2 to 10, 130 and/or the nucleic acid sequences complementary thereto (nucleotide sequences corresponding to the various variable sequences of the CRISPR2 locus of the serotype Abortusequi);

set S25-1, comprising or constituted of at least one probe comprising at least or constituted of at least 8 consecutive nucleotides of any one of the nucleic acid sequences SEQ ID Nos: 378, 379 and/or the nucleic acid sequences complementary thereto (nucleotide sequences corresponding to the various variable sequences of the CRISPR1 locus of the serotype Kiel);

set S25-2, comprising or constituted of at least one probe comprising at least or constituted of at least 8 consecutive nucleotides of any one of the nucleic acid sequences SEQ ID Nos: 392, 393, 411, 412 and/or the nucleic acid sequences complementary thereto (nucleotide sequences corresponding to the various variable sequences of the CRISPR2 locus of the serotype Kiel);

set S26-1, comprising or constituted of at least one probe comprising at least or constituted of at least 8 consecutive nucleotides of any one of the nucleic acid sequences SEQ ID Nos: 509, 510, 512, 513, 637 to 660, 1086, 1107 and/or the nucleic acid sequences complementary thereto (nucleotide sequences corresponding to the various variable sequences of the CRISPR1 locus of the serotype Mbandaka);

set S26-2, comprising or constituted of at least one probe comprising at least or constituted of at least 8 consecutive nucleotides of any one of the nucleic acid sequences SEQ ID Nos: 661 to 666, 668, 669, 672, 683, 690 to 695, 731, 918 and/or the nucleic acid sequences complementary thereto (nucleotide sequences corresponding to the various variable sequences of the CRISPR2 locus of the serotype Mbandaka);

set S27-1, comprising or constituted of at least one probe comprising at least or constituted of at least 8 consecutive nucleotides of any one of the nucleic acid sequences SEQ ID No.: 916 and/or the nucleic acid sequence complementary thereto (nucleotide sequences corresponding to the various variable sequences of the CRISPR1 locus of the serotype Miami);

set S27-2, comprising or constituted of at least one probe comprising at least or constituted of at least 8 consecutive nucleotides of any one of the nucleic acid sequences SEQ ID Nos: 25, 696 to 700 and/or the nucleic acid sequences complementary thereto (nucleotide sequences corresponding to the various variable sequences of the CRISPR2 locus of the serotype Miami);

set S28-1, comprising or constituted of at least one probe comprising at least or constituted of at least 8 consecutive nucleotides of any one of the nucleic acid sequences SEQ ID Nos: 55, 701 to 730, 732 to 768, 1115, 1228, 1232 to 1237, 1601, 1671 to 1680, 1682 to 1694, 1747 and/or the nucleic acid sequences complementary thereto (nucleotide sequences corresponding to the various variable sequences of the CRISPR1 locus of the serotype Montevideo);

set S28-2, comprising or constituted of at least one probe comprising at least or constituted of at least 8 consecutive nucleotides of any one of the nucleic acid sequences SEQ ID Nos: 589, 769 to 829, 933, 1245, 1697, 1698 and/or the nucleic acid sequences complementary thereto (nucleotide sequences corresponding to the various variable sequences of the CRISPR2 locus of the serotype Montevideo);

set S29-1, comprising or constituted of at least one probe comprising at least or constituted of at least 8 consecutive nucleotides of any one of the nucleic acid sequences SEQ ID Nos: 379, 380, 383 to 385, 387, 389 to 391 and/or the nucleic acid sequences complementary thereto (nucleotide sequences corresponding to the various variable sequences of the CRISPR1 locus of the serotype Nitra);

set S29-2, comprising or constituted of at least one probe comprising at least or constituted of at least 8 consecutive nucleotides of any one of the nucleic acid sequences SEQ ID Nos: 392 to 394, 404, 407 to 413, 519 and/or the nucleic acid sequences complementary thereto (nucleotide sequences corresponding to the various variable sequences of the CRISPR2 locus of the serotype Nitra);

set S30-1, comprising or constituted of at least one probe comprising at least or constituted of at least 8 consecutive nucleotides of any one of the nucleic acid sequences SEQ ID Nos: 931, 932, 1104, 1105 and/or the nucleic acid sequences complementary thereto (nucleotide sequences corresponding to the various variable sequences of the CRISPR1 locus of the serotype Sendai);

set S30-2, comprising or constituted of at least one probe comprising at least or constituted of at least 8 consecutive nucleotides of the nucleic acid sequence SEQ ID No.: 936 and/or the nucleic acid sequence complementary thereto (nucleotide sequences corresponding to the variable sequence of the CRISPR2 locus of the serotype Sendai);

set S31-1, comprising or constituted of at least one probe comprising at least or constituted of at least 8 consecutive nucleotides of any one of the nucleic acid sequences SEQ ID Nos: 714 to 716, 1228 to 1239 and/or the nucleic acid sequences complementary thereto (nucleotide sequences corresponding to the various variable sequences of the CRISPR1 locus of the serotype Schwarzengrund);

set S31-2, comprising or constituted of at least one probe comprising at least or constituted of at least 8 consecutive nucleotides of any one of the nucleic acid sequences SEQ ID Nos: 196, 992, 995, 1172, 1240 to 1244, 1246 to 1253 and/or the nucleic acid sequences complementary thereto (nucleotide sequences corresponding to the various variable sequences of the CRISPR2 locus of the serotype Schwarzengrund);

set S32-1, comprising or constituted of at least one probe comprising at least or constituted of at least 8 consecutive nucleotides of any one of the nucleic acid sequences SEQ ID Nos: 232, 238, 239, 998, 999, 1002, 1106, 1261 and/or the nucleic acid sequences complementary thereto (nucleotide sequences corresponding to the various variable sequences of the CRISPR1 locus of the serotype Typhisuis);

set S32-2, comprising or constituted of at least one probe comprising at least or constituted of at least 8 consecutive nucleotides of the nucleic acid sequence SEQ ID No.: 1262 and/or the nucleic acid sequence complementary thereto (nucleotide sequences corresponding to the variable sequence of the CRISPR2 locus of the serotype Typhisuis);

set S33-1, comprising or constituted of at least one probe comprising at least or constituted of at least 8 consecutive nucleotides of any one of the nucleic acid sequences SEQ ID Nos: 466 to 486 and/or the nucleic acid sequences complementary thereto (nucleotide sequences corresponding to the various variable sequences of the CRISPR1 locus of the various serotypes of the *houtenae* subspecies);

set S33-2, comprising or constituted of at least one probe comprising at least or constituted of at least 8 consecutive nucleotides of any one of the nucleic acid sequences SEQ ID Nos: 487 to 490 and/or the nucleic acid sequences complementary thereto (nucleotide sequences corresponding to the various variable sequences of the CRISPR2 locus of the various serotypes of the *houtenae* subspecies);

set S34-1, comprising or constituted of at least one probe comprising at least or constituted of at least 8 consecutive nucleotides of any one of the nucleic acid sequences SEQ ID Nos: 338 to 376 and/or the nucleic acid sequences complementary thereto (nucleotide sequences corresponding to the various variable sequences of the CRISPR1 locus of the various serotypes of the *diarizonae* subspecies);

set S34-2, comprising or constituted of at least one probe comprising at least or constituted of at least 8 consecutive nucleotides of the nucleic acid sequence SEQ ID No.: 377 and/or the nucleic acid sequence complementary thereto (nucleotide sequences corresponding to the variable sequence of the CRISPR2 locus of the various serotypes of the *diarizonae* subspecies);

set S35-1, comprising or constituted of at least one probe comprising at least or constituted of at least 8 consecutive nucleotides of any one of the nucleic acid sequences SEQ ID Nos: 1007 to 1037, 1848 to 1884 and/or the nucleic acid sequences complementary thereto (nucleotide sequences corresponding to the various variable sequences of the CRISPR1 locus of the *salamae* subspecies);

set S35-2, comprising or constituted of at least one probe comprising at least or constituted of at least 8 consecutive nucleotides of any one of the nucleic acid sequences SEQ ID Nos: 1038 to 1061, 1885 and/or the nucleic acid sequences complementary thereto (nucleotide sequences corresponding to the various variable sequences of the CRISPR2 locus of the *salamae* subspecies);

set S36, comprising or constituted of at least one probe comprising at least or constituted of at least 8 consecutive nucleotides of the nucleic acid sequence SEQ ID No.: 95 and/or the nucleic acid sequence complementary thereto (nucleotide sequences corresponding to the variable sequence of the CRISPR1 locus of the various serotypes of the *arizonae* subspecies);

set S37-1, comprising or constituted of at least one probe comprising at least or constituted of at least 8 consecutive nucleotides of any one of the nucleic acid sequences SEQ ID Nos: 491 to 499 and/or the nucleic acid sequences complementary thereto (nucleotide sequences corresponding to the various variable sequences of the CRISPR1 locus of the various serotypes of the *indica* subspecies);

set S37-2, comprising or constituted of at least one probe comprising at least or constituted of at least 8 consecutive nucleotides of any one of the nucleic acid sequences SEQ ID Nos: 500 to 503, 1574 to 1589 and/or the nucleic acid sequences complementary thereto (nucleotide sequences corresponding to the various variable sequences of the CRISPR2 locus of the various serotypes of the *indica* subspecies);

set S38-1, comprising or constituted of at least one probe comprising at least or constituted of at least 8 consecutive nucleotides of any one of the nucleic acid sequences SEQ ID Nos: 32 to 66, 382, 416, 667, 2036 and/or the nucleic acid sequences complementary thereto (nucleotide sequences corresponding to the various variable sequences of the CRISPR1 locus of the serotype Altona);

set S38-2, comprising or constituted of at least one probe comprising at least or constituted of at least 8 consecutive nucleotides of any one of the nucleic acid sequences SEQ ID Nos: 854, 933, 1095, 1306, 1354 to 1389, 1696 and/or the nucleic acid sequences complementary thereto (nucleotide sequences corresponding to the various variable sequences of the CRISPR2 locus of the serotype Altona);

set S39-1, comprising or constituted of at least one probe comprising at least or constituted of at least 8 consecutive nucleotides of any one of the nucleic acid sequences SEQ ID Nos: 240, 241, 1120, 1121 and/or the nucleic acid sequences complementary thereto (nucleotide sequences corresponding to the various variable sequences of the CRISPR1 locus of the serotype Choleraesuis variety Decatur);

set S39-2, comprising or constituted of at least one probe comprising at least or constituted of at least 8 consecutive nucleotides of any one of the nucleic acid sequences SEQ ID Nos: 225, 247 to 251, 253 to 256, 259 to 268, 270 to 279, 281 to 289, 292 to 294 and/or the nucleic acid sequences complementary thereto (nucleotide sequences corresponding to the various variable sequences of the CRISPR2 locus of the serotype Choleraesuis variety Decatur);

set S40-1, comprising or constituted of at least one probe comprising at least or constituted of at least 8 consecutive nucleotides of any one of the nucleic acid sequences SEQ ID Nos: 11, 232, 238, 239, 240, 242 to 245, 233 to 237, 959, 1106, 1120 and/or the nucleic acid sequences complementary thereto (nucleotide sequences corresponding to the various variable sequences of the CRISPR1 locus of the serotype Choleraesuis variety Kunzendorf);

set S40-2, comprising or constituted of at least one probe comprising at least or constituted of at least 8 consecutive nucleotides of any one of the nucleic acid sequences SEQ ID Nos: 246, 252, 258, 269, 280, 290, 291, 392, 563, 933 and/or the nucleic acid sequences complementary thereto (nucleotide sequences corresponding to the various variable sequences of the CRISPR2 locus of the serotype Choleraesuis variety Kunzendorf);

set S41-1, comprising or constituted of at least one probe comprising at least or constituted of at least 8 consecutive nucleotides of any one of the nucleic acid sequences SEQ ID Nos: 11, 242 to 245, 232 to 239, 959, 1000, 1106, 1139, 1120 and/or the nucleic acid sequences complementary thereto (nucleotide sequences corresponding to the various variable sequences of the CRISPR1 locus of the serotypes Choleraesuis and Choleraesuis sensu stricto);

set S41-2, comprising or constituted of at least one probe comprising at least or constituted of at least 8 consecutive nucleotides of any one of the nucleic acid sequences SEQ ID Nos: 246, 252, 258, 269, 280, 290, 291, 392, 563, 574, 933, 1003, 1004 and/or the nucleic acid sequences complementary thereto (nucleotide sequences corresponding to the various variable sequences of the CRISPR2 locus of the serotypes Choleraesuis and Choleraesuis sensu stricto);

set S42-1, comprising or constituted of at least one probe comprising at least or constituted of at least 8 consecutive nucleotides of any one of the nucleic acid sequences SEQ ID Nos: 416 to 420, 1122 and/or the nucleic acid sequences complementary thereto (nucleotide sequences corresponding to the various variable sequences of the CRISPR1 locus of the serotype Goettingen);

set S42-2, comprising or constituted of at least one probe comprising at least or constituted of at least 8 consecutive nucleotides of the nucleic acid sequence SEQ ID No.: 1548 and/or the nucleic acid sequence complementary thereto (nucleotide sequences corresponding to the variable sequence of the CRISPR2 locus of the serotype Goettingen);

set S43-1, comprising or constituted of at least one probe comprising at least or constituted of at least 8 consecutive nucleotides of any one of the nucleic acid sequences SEQ ID Nos: 630 to 636, 937, 948, 1120, 1143 and/or the nucleic acid sequences complementary thereto (nucleotide sequences corresponding to the various variable sequences of the CRISPR1 locus of the serotype Manhattan);

set S43-2, comprising or constituted of at least one probe comprising at least or constituted of at least 8 consecutive nucleotides of any one of the nucleic acid sequences SEQ ID Nos: 392, 1653 and/or the nucleic acid sequences complementary thereto (nucleotide sequences corresponding to the various variable sequences of the CRISPR2 locus of the serotype Manhattan);

set S44-1, comprising or constituted of at least one probe comprising at least or constituted of at least 8 consecutive nucleotides of any one of the nucleic acid sequences SEQ ID Nos: 96 to 155 and/or the nucleic acid sequences complementary thereto (nucleotide sequences corresponding to the various variable sequences of the CRISPR1 locus of certain serotypes of the species *S. bongori*);

set S44-2, comprising or constituted of at least one probe comprising at least or constituted of at least 8 consecutive nucleotides of any one of the nucleic acid sequences SEQ ID Nos: 156 to 195, 1421 to 1430 and/or the nucleic acid sequences complementary thereto (nucleotide sequences corresponding to the various variable sequences of the CRISPR2 locus of certain serotypes of the species *S. bongori*);

set S45-1, comprising or constituted of at least one probe comprising at least or constituted of at least 8 consecutive nucleotides of any one of the nucleic acid sequences SEQ ID Nos: 962, 1106, 1133, 1804, 1808 and/or the nucleic acid sequences complementary thereto (nucleotide sequences corresponding to the various variable sequences of the CRISPR1 locus of the serotype Abony);

set S45-2, comprising or constituted of at least one probe comprising at least or constituted of at least 8 consecutive nucleotides of any one of the nucleic acid sequences SEQ ID Nos: 972, 989, 1334 to 1339, 1474, 1499 and/or the nucleic acid sequences complementary thereto (nucleotide sequences corresponding to the various variable sequences of the CRISPR2 locus of the serotype Abony);

set S46-1, comprising or constituted of at least one probe comprising at least or constituted of at least 8 consecutive nucleotides of any one of the nucleic acid sequences SEQ ID Nos: 448, 860 to 875, 882, 883, 1340 to 1345, 1721 to 1723 and/or the nucleic acid sequences complementary thereto (nucleotide sequences corresponding to the various variable sequences of the CRISPR1 locus of the serotype Aesch);

set S46-2, comprising or constituted of at least one probe comprising at least or constituted of at least 8 consecutive nucleotides of any one of the nucleic acid sequences SEQ ID Nos: 563, 625, 626, 885, 887 to 893, 896, 933, 1346 to 1348, 1749, 1759 and/or the nucleic acid sequences complementary thereto (nucleotide sequences corresponding to the various variable sequences of the CRISPR2 locus of the serotype Aesch);

set S47-1, comprising or constituted of at least one probe comprising at least or constituted of at least 8 consecutive nucleotides of any one of the nucleic acid sequences SEQ ID Nos: 834, 1120, 1349, 1350, 1351, 1713, 1718 and/or the nucleic acid sequences complementary thereto (nucleotide sequences corresponding to the various variable sequences of the CRISPR1 locus of the serotype Albany);

set S47-2, comprising or constituted of at least one probe comprising at least or constituted of at least 8 consecutive nucleotides of any one of the nucleic acid sequences SEQ ID Nos: 842, 852, 1352, 1353 and/or the nucleic acid sequences complementary thereto (nucleotide sequences corresponding to the various variable sequences of the CRISPR2 locus of the serotype Albany);

set S48-1, comprising or constituted of at least one probe comprising at least or constituted of at least 8 consecutive nucleotides of the nucleic acid sequence SEQ ID No.: 917 and/or the nucleic acid sequence complementary thereto (nucleotide sequences corresponding to the variable sequence of the CRISPR1 locus of the serotype Arechavalata);

set S48-2, comprising or constituted of at least one probe comprising at least or constituted of at least 8 consecutive nucleotides of any one of the nucleic acid sequences SEQ ID Nos: 225, 227 to 231, 1398 and/or the nucleic acid sequences complementary thereto (nucleotide sequences corresponding to the various variable sequences of the CRISPR2 locus of the serotype Arechavalata);

set S49-1, comprising or constituted of at least one probe comprising at least or constituted of at least 8 consecutive nucleotides of any one of the nucleic acid sequences SEQ ID Nos: 448, 449, 860, 871 to 873, 878, 895, 903 to 905, 907, 1719 to 1721, 1745 and/or the nucleic acid sequences complementary thereto (nucleotide sequences corresponding to the various variable sequences of the CRISPR1 locus of the serotype Bardo);

set S49-2, comprising or constituted of at least one probe comprising at least or constituted of at least 8 consecutive nucleotides of any one of the nucleic acid sequences SEQ ID Nos: 563, 622, 626, 885, 886 to 890, 893, 896, 907, 910 to 915, 933, 1756 to 1758 and/or the nucleic acid sequences complementary thereto (nucleotide sequences corresponding to the various variable sequences of the CRISPR2 locus of the serotype Bardo);

set S50-1, comprising or constituted of at least one probe comprising at least or constituted of at least 8 consecutive nucleotides of any one of the nucleic acid sequences SEQ ID Nos: 82, 1401 and/or the nucleic acid sequences complementary thereto (nucleotide sequences corresponding to the various variable sequences of the CRISPR1 locus of the serotype Berta);

set S50-2, comprising or constituted of at least one probe comprising at least or constituted of at least 8 consecutive nucleotides of any one of the nucleic acid sequences SEQ ID Nos: 246, 918, 933, 1401, 1448 and/or the nucleic acid sequences complementary thereto (nucleotide sequences corresponding to the various variable sequences of the CRISPR2 locus of the serotype Berta);

set S51-1, comprising or constituted of at least one probe comprising at least or constituted of at least 8 consecutive nucleotides of any one of the nucleic acid sequences SEQ ID Nos: 1, 37, 1106, 1402 to 1416, 2055 and/or the nucleic acid sequences complementary thereto (nucleotide sequences corresponding to the various variable sequences of the CRISPR1 locus of the serotype Bispebjerg);

set S51-2, comprising or constituted of at least one probe comprising at least or constituted of at least 8 consecutive nucleotides of any one of the nucleic acid sequences SEQ ID Nos: 2 to 4, 9, 1417 to 1420, 1547, 1572 and/or the nucleic acid sequences complementary thereto (nucleotide sequences corresponding to the various variable sequences of the CRISPR2 locus of the serotype Bispebjerg);

set S52-1, comprising or constituted of at least one probe comprising at least or constituted of at least 8 consecutive nucleotides of any one of the nucleic acid sequences SEQ ID Nos: 379, 380, 383, 385, 387, 389 to 391 and/or the nucleic acid sequences complementary thereto (nucleotide sequences corresponding to the various variable sequences of the CRISPR1 locus of the serotype Blegdam);

set S52-2, comprising or constituted of at least one probe comprising at least or constituted of at least 8 consecutive nucleotides of any one of the nucleic acid sequences SEQ ID Nos: 392 to 394, 404, 407, 412, 413, 519 and/or the nucleic acid sequences complementary thereto (nucleotide sequences corresponding to the various variable sequences of the CRISPR2 locus of the serotype Blegdam);

set S53-1, comprising or constituted of at least one probe comprising at least or constituted of at least 8 consecutive nucleotides of the nucleic acid sequence SEQ ID No.: 917 and/or the nucleic acid sequence complementary thereto (nucleotide sequences corresponding to the variable sequence of the CRISPR1 locus of the serotype Chester);

set S53-2, comprising or constituted of at least one probe comprising at least or constituted of at least 8 consecutive nucleotides of any one of the nucleic acid sequences SEQ ID Nos: 933, 1445 to 1447 and/or the nucleic acid sequences complementary thereto (nucleotide sequences corresponding to the various variable sequences of the CRISPR2 locus of the serotype Chester);

set S54-1, comprising or constituted of at least one probe comprising at least or constituted of at least 8 consecutive nucleotides of any one of the nucleic acid sequences SEQ ID Nos: 1449 to 1454, 1460, 1467 to 1473 and/or the nucleic acid sequences complementary thereto (nucleotide sequences corresponding to the various variable sequences of the CRISPR1 locus of the serotype Concord);

set S54-2, comprising or constituted of at least one probe comprising at least or constituted of at least 8 consecutive nucleotides of any one of the nucleic acid sequences SEQ ID Nos: 972, 1474 to 1493, 1495 to 1499 and/or the nucleic acid sequences complementary thereto (nucleotide sequences corresponding to the various variable sequences of the CRISPR2 locus of the serotype Concord);

set S55-1, comprising or constituted of at least one probe comprising at least or constituted of at least 8 consecutive nucleotides of any one of the nucleic acid sequences SEQ ID Nos: 1106, 1107 to 1109, 1123, 1128 to 1131, 1133, 1137 to 1140, 1550, 1559 to 1561 and/or the nucleic acid sequences complementary thereto (nucleotide sequences corresponding to the various variable sequences of the CRISPR1 locus of the serotype Crossness);

set S55-2, comprising or constituted of at least one probe comprising at least or constituted of at least 8 consecutive nucleotides of any one of the nucleic acid sequences SEQ ID Nos: 455, 1144, 1145, 1149 to 1153, 1155 to 1160, 1163, 1172 to 1174 and/or the nucleic acid sequences complementary thereto (nucleotide sequences corresponding to the various variable sequences of the CRISPR2 locus of the serotype Crossness);

set S56-1, comprising or constituted of at least one probe comprising at least or constituted of at least 8 consecutive nucleotides of any one of the nucleic acid sequences SEQ ID Nos: 834, 1120, 1349 to 1351, 1713, 1718 and/or the nucleic acid sequences complementary thereto (nucleotide sequences corresponding to the various variable sequences of the CRISPR1 locus of the serotype Duesseldorf);

set S56-2, comprising or constituted of at least one probe comprising at least or constituted of at least 8 consecutive nucleotides of any one of the nucleic acid sequences SEQ ID Nos: 842, 852, 1352, 1353, 1501 to 1503 and/or the nucleic acid sequences complementary thereto (nucleotide sequences corresponding to the various variable sequences of the CRISPR2 locus of the serotype Duesseldorf);

set S57-1, comprising or constituted of at least one probe comprising at least or constituted of at least 8 consecutive nucleotides of any one of the nucleic acid sequences SEQ ID Nos: 941, 1504 to 1508 and/or the nucleic acid sequences complementary thereto (nucleotide sequences corresponding to the various variable sequences of the CRISPR1 locus of the serotype Emek);

set S57-2, comprising or constituted of at least one probe comprising at least or constituted of at least 8 consecutive nucleotides of any one of the nucleic acid sequences SEQ ID Nos: 1260, 1509 to 1524, 1526, 1527 and/or the nucleic acid sequences complementary thereto (nucleotide sequences corresponding to the various variable sequences of the CRISPR2 locus of the serotype Emek);

set S58-1, comprising or constituted of at least one probe comprising at least or constituted of at least 8 consecutive nucleotides of the nucleic acid sequence SEQ ID No.: 558 and/or the nucleic acid sequence complementary thereto (nucleotide sequences corresponding to the variable sequence of the CRISPR1 locus of the serotype Fulica);

set S58-2, comprising or constituted of at least one probe comprising at least or constituted of at least 8 consecutive nucleotides of any one of the nucleic acid sequences SEQ ID Nos: 2, 4, 5, 1333, 1547 and/or the nucleic acid sequences complementary thereto (nucleotide sequences corresponding to the various variable sequences of the CRISPR2 locus of the serotype Fulica);

set S59-1, comprising or constituted of at least one probe comprising at least or constituted of at least 8 consecutive nucleotides of the nucleic acid sequence SEQ ID No.: 917 and/or the nucleic acid sequence complementary thereto (nucleotide sequences corresponding to the variable sequence of the CRISPR1 locus of the serotype Gueuletapee);

set S59-2, comprising or constituted of at least one probe comprising at least or constituted of at least 8 consecutive nucleotides of any one of the nucleic acid sequences SEQ ID Nos: 597, 918 to 925, 933, 1549 and/or the nucleic acid sequences complementary thereto (nucleotide sequences corresponding to the various variable sequences of the CRISPR2 locus of the serotype Gueuletapee);

set S60-1, comprising or constituted of at least one probe comprising at least or constituted of at least 8 consecutive nucleotides of any one of the nucleic acid sequences SEQ ID Nos: 1106 to 1109, 1111 to 1116, 1118, 1123, 1128 to 1131, 1133, 1137 to 1140, 1150, 1151, 1555 to 1562 and/or the nucleic acid sequences complementary thereto (nucleotide sequences corresponding to the various variable sequences of the CRISPR1 locus of the serotype Heidelberg);

set S60-2, comprising or constituted of at least one probe comprising at least or constituted of at least 8 consecutive nucleotides of any one of the nucleic acid sequences SEQ ID Nos: 455, 1144, 1145, 1149 to 1153, 1155 to 1163, 1172 to 1174, 1563 and/or the nucleic acid sequences complementary thereto (nucleotide sequences corresponding to the various variable sequences of the CRISPR2 locus of the serotype Heidelberg);

set S61-1, comprising or constituted of at least one probe comprising at least or constituted of at least 8 consecutive nucleotides of any one of the nucleic acid sequences SEQ ID Nos: 558, 1565 to 1571 and/or the nucleic acid sequences complementary thereto (nucleotide sequences corresponding to the various variable sequences of the CRISPR1 locus of the serotype Hessarek);

set S61-2, comprising or constituted of at least one probe comprising at least or constituted of at least 8 consecutive nucleotides of any one of the nucleic acid sequences SEQ ID Nos: 2 to 4, 1547, 1572, 1573 and/or the nucleic acid sequences complementary thereto (nucleotide sequences corresponding to the various variable sequences of the CRISPR2 locus of the serotype Hessarek);

set S62-1, comprising or constituted of at least one probe comprising at least or constituted of at least 8 consecutive nucleotides of any one of the nucleic acid sequences SEQ ID Nos: 1591, 1592, 1667 and/or the nucleic acid sequences complementary thereto (nucleotide sequences corresponding to the various variable sequences of the CRISPR1 locus of the serotype Itami);

set S62-2, comprising or constituted of at least one probe comprising at least or constituted of at least 8 consecutive nucleotides of any one of the nucleic acid sequences SEQ ID Nos: 918, 1593 to 1600, 1744 and/or the nucleic acid sequences complementary thereto (nucleotide sequences corresponding to the various variable sequences of the CRISPR2 locus of the serotype Itami);

set S63-1, comprising or constituted of at least one probe comprising at least or constituted of at least 8 consecutive nucleotides of any one of the nucleic acid sequences SEQ ID Nos: 1601 to 1606, 1687 and/or the nucleic acid sequences complementary thereto (nucleotide sequences corresponding to the various variable sequences of the CRISPR1 locus of the serotype Javiana);

set S63-2, comprising or constituted of at least one probe comprising at least or constituted of at least 8 consecutive nucleotides of any one of the nucleic acid sequences SEQ ID Nos: 589 to 601, 973, 1607, 1608 and/or the nucleic acid sequences complementary thereto (nucleotide sequences corresponding to the various variable sequences of the CRISPR2 locus of the serotype Javiana);

set S64-1, comprising or constituted of at least one probe comprising at least or constituted of at least 8 consecutive nucleotides of any one of the nucleic acid sequences SEQ ID Nos: 1609 to 1621, 1494, 1525 and/or the nucleic acid sequences complementary thereto (nucleotide sequences corresponding to the various variable sequences of the CRISPR1 locus of the serotype Johannesburg);

set S64-2, comprising or constituted of at least one probe comprising at least or constituted of at least 8 consecutive nucleotides of any one of the nucleic acid sequences SEQ ID Nos: 918, 1697, 1698 and/or the nucleic acid sequences complementary thereto (nucleotide sequences corresponding to the various variable sequences of the CRISPR2 locus of the serotype Johannesburg);

set S65-1, comprising or constituted of at least one probe comprising at least or constituted of at least 8 consecutive nucleotides of any one of the nucleic acid sequences SEQ ID Nos: 444, 448, 1184, 1622 to 1637 and/or the nucleic acid sequences complementary thereto (nucleotide sequences corresponding to the various variable sequences of the CRISPR1 locus of the serotype Kentucky);

set S65-2, comprising or constituted of at least one probe comprising at least or constituted of at least 8 consecutive nucleotides of any one of the nucleic acid sequences SEQ ID Nos: 385, 519, 1638 to 1652, 1746 and/or the nucleic acid sequences complementary thereto (nucleotide sequences corresponding to the various variable sequences of the CRISPR2 locus of the serotype Kentucky);

set S66-1, comprising or constituted of at least one probe comprising at least or constituted of at least 8 consecutive nucleotides of the nucleic acid sequence SEQ ID No.: 67 and/or the nucleic acid sequence complementary thereto (nucleotide sequences corresponding to the variable sequence of the CRISPR1 locus of the serotype Kundunchi);

set S66-2, comprising or constituted of at least one probe comprising at least or constituted of at least 8 consecutive nucleotides of any one of the nucleic acid sequences SEQ ID Nos: 972, 983, 989, 1201, 1204, 1205, 1210 to 1212 and/or the nucleic acid sequences complementary thereto (nucleotide sequences corresponding to the various variable sequences of the CRISPR2 locus of the serotype Kundunchi);

set S67-1, comprising or constituted of at least one probe comprising at least or constituted of at least 8 consecutive nucleotides of any one of the nucleic acid sequences SEQ ID Nos: 448, 449, 860, 871, 878 to 881, 1721, 1724 and/or the nucleic acid sequences complementary thereto (nucleotide sequences corresponding to the various variable sequences of the CRISPR1 locus of the serotype Lindenburg);

set S67-2, comprising or constituted of at least one probe comprising at least or constituted of at least 8 consecutive nucleotides of any one of the nucleic acid sequences SEQ ID Nos: 563, 622, 885, 886, 896, 907, 910 to 915, 933, 1748, 1757 and/or the nucleic acid sequences complementary thereto (nucleotide sequences corresponding to the various variable sequences of the CRISPR2 locus of the serotype Lindenburg);

set S68-1, comprising or constituted of at least one probe comprising at least or constituted of at least 8 consecutive nucleotides of the nucleic acid sequence SEQ ID No.: 917 and/or the nucleic acid sequence complementary thereto (nucleotide sequences corresponding to the variable sequence of the CRISPR1 locus of the serotype Maracaibo);

set S68-2, comprising or constituted of at least one probe comprising at least or constituted of at least 8 consecutive nucleotides of any one of the nucleic acid sequences SEQ ID Nos: 1240, 1247, 1248, 1654 to 1656 and/or the nucleic acid sequences complementary thereto (nucleotide sequences corresponding to the various variable sequences of the CRISPR2 locus of the serotype Maracaibo);

set S69-1, comprising or constituted of at least one probe comprising at least or constituted of at least 8 consecutive nucleotides of any one of the nucleic acid sequences SEQ ID Nos: 627, 834, 1120, 1660 to 1669 and/or the nucleic acid sequences complementary thereto (nucleotide sequences corresponding to the various variable sequences of the CRISPR1 locus of the serotype Mississippi);

set S69-2, comprising or constituted of at least one probe comprising at least or constituted of at least 8 consecutive nucleotides of any one of the nucleic acid sequences SEQ ID Nos: 842, 1670 and/or the nucleic acid sequences complementary thereto (nucleotide sequences corresponding to the various variable sequences of the CRISPR2 locus of the serotype Mississippi);

set S70-1, comprising or constituted of at least one probe comprising at least or constituted of at least 8 consecutive nucleotides of any one of the nucleic acid sequences SEQ ID Nos: 941, 942, 949, 1699 to 1712, 2109 and/or the nucleic acid sequences complementary thereto (nucleotide sequences corresponding to the various variable sequences of the CRISPR1 locus of the serotype Muenchen);

set S70-2, comprising or constituted of at least one probe comprising at least or constituted of at least 8 consecutive nucleotides of any one of the nucleic acid sequences SEQ ID Nos: 392, 1653 and/or the nucleic acid sequences complementary thereto (nucleotide sequences corresponding to the various variable sequences of the CRISPR2 locus of the serotype Muenchen);

set S71-1, comprising or constituted of at least one probe comprising at least or constituted of at least 8 consecutive nucleotides of any one of the nucleic acid sequences SEQ ID Nos: 11, 1120, 1497, 1760 to 1775, 1809 and/or the nucleic acid sequences complementary thereto (nucleotide sequences corresponding to the various variable sequences of the CRISPR1 locus of the serotype Niarembe);

set S71-2, comprising or constituted of at least one probe comprising at least or constituted of at least 8 consecutive nucleotides of any one of the nucleic acid sequences SEQ ID Nos: 90, 1776 to 1785 and/or the nucleic acid sequences complementary thereto (nucleotide sequences corresponding to the various variable sequences of the CRISPR2 locus of the serotype Niarembe);

set S72-1, comprising or constituted of at least one probe comprising at least or constituted of at least 8 consecutive nucleotides of any one of the nucleic acid sequences SEQ ID Nos: 666, 1786 to 1791 and/or the nucleic acid sequences complementary thereto (nucleotide sequences corresponding to the various variable sequences of the CRISPR1 locus of the serotype Overvecht);

set S72-2, comprising or constituted of at least one probe comprising at least or constituted of at least 8 consecutive nucleotides of any one of the nucleic acid sequences SEQ ID Nos: 783, 1146, 1178, 1179, 1181, 1792 to 1799, 1801 and/or the nucleic acid sequences complementary thereto (nucleotide sequences corresponding to the various variable sequences of the CRISPR2 locus of the serotype Overvecht);

set S73-1, comprising or constituted of at least one probe comprising at least or constituted of at least 8 consecutive nucleotides of the nucleic acid sequences SEQ ID No.: 917 and/or the nucleic acid sequence complementary thereto (nucleotide sequences corresponding to the variable sequence of the CRISPR1 locus of the serotype Poona);

set S73-2, comprising or constituted of at least one probe comprising at least or constituted of at least 8 consecutive nucleotides of any one of the nucleic acid sequences SEQ ID Nos: 82, 87, 918, 933, 1826 and/or the nucleic acid sequences complementary thereto (nucleotide sequences corresponding to the various variable sequences of the CRISPR2 locus of the serotype Poona);

set S74-1, comprising or constituted of at least one probe comprising at least or constituted of at least 8 consecutive nucleotides of any one of the nucleic acid sequences SEQ ID Nos: 295 to 297, 307, 313, 317, 323, 1120, 1825, 1827 to 1837, 2023 and/or the nucleic acid sequences complementary thereto (nucleotide sequences corresponding to the various variable sequences of the CRISPR1 locus of the serotype Potsdam);

set S74-2, comprising or constituted of at least one probe comprising at least or constituted of at least 8 consecutive nucleotides of any one of the nucleic acid sequences SEQ ID Nos: 663, 1304, 1838 to 1847 and/or the nucleic acid sequences complementary thereto (nucleotide sequences corresponding to the various variable sequences of the CRISPR2 locus of the serotype Potsdam);

set S75-1, comprising or constituted of at least one probe comprising at least or constituted of at least 8 consecutive nucleotides of the nucleic acid sequence SEQ ID No.: 917 and/or the nucleic acid sequence complementary thereto (nucleotide sequences corresponding to the variable sequence of the CRISPR1 locus of the serotype Reading);

set S75-2, comprising or constituted of at least one probe comprising at least or constituted of at least 8 consecutive nucleotides of the nucleic acid sequence SEQ ID No.: 225 and/or the nucleic acid sequence complementary thereto (nucleotide sequences corresponding to the variable sequence of the CRISPR2 locus of the serotype Reading);

set S76-1, comprising or constituted of at least one probe comprising at least or constituted of at least 8 consecutive nucleotides of any one of the nucleic acid sequences SEQ ID Nos: 379, 380, 383 to 385, 387, 389, 390 and/or the nucleic acid sequences complementary thereto (nucleotide sequences corresponding to the various variable sequences of the CRISPR1 locus of the serotype Rosenberg);

set S76-2, comprising or constituted of at least one probe comprising at least or constituted of at least 8 consecutive nucleotides of any one of the nucleic acid sequences SEQ ID Nos: 392, 393, 404, 407 to 413 and/or the nucleic acid sequences complementary thereto (nucleotide sequences corresponding to the various variable sequences of the CRISPR2 locus of the serotype Rosenberg);

set S77-1, comprising or constituted of at least one probe comprising at least or constituted of at least 8 consecutive nucleotides of the nucleic acid sequence SEQ ID No.: 917 and/or the nucleic acid sequence complementary thereto (nucleotide sequences corresponding to the variable sequence of the CRISPR1 locus of the serotype Rubislaw);

set S77-2, comprising or constituted of at least one probe comprising at least or constituted of at least 8 consecutive nucleotides of the nucleic acid sequence SEQ ID No.: 225 and/or the nucleic acid sequence complementary thereto (nucleotide sequences corresponding to the variable sequence of the CRISPR1 locus of the serotype Rubislaw);

set S78-1, comprising or constituted of at least one probe comprising at least or constituted of at least 8 consecutive nucleotides of any one of the nucleic acid sequences SEQ ID Nos: 1525, 1609 to 1621 and/or the nucleic acid sequences complementary thereto (nucleotide sequences corresponding to the various variable sequences of the CRISPR2 locus of the serotype Sandiego);

set S78-2, comprising or constituted of at least one probe comprising at least or constituted of at least 8 consecutive nucleotides of any one of the nucleic acid sequences SEQ ID Nos: 225 to 227, 229 to 231 and/or the nucleic acid sequences complementary thereto (nucleotide sequences corresponding to the various variable sequences of the CRISPR2 locus of the serotype Sandiego);

set S79-1, comprising or constituted of at least one probe comprising at least or constituted of at least 8 consecutive nucleotides of any one of the nucleic acid sequences SEQ ID Nos: 1106, 1456, 1917 to 1924 and/or the nucleic acid sequences complementary thereto (nucleotide sequences corresponding to the various variable sequences of the CRISPR1 locus of the serotype Stourbridge);

set S79-2, comprising or constituted of at least one probe comprising at least or constituted of at least 8 consecutive nucleotides of any one of the nucleic acid sequences SEQ ID Nos: 918, 1093, 1925 to 1936 and/or the nucleic acid sequences complementary thereto (nucleotide sequences corresponding to the various variable sequences of the CRISPR2 locus of the serotype Stourbridge);

set S80-1, comprising or constituted of at least one probe comprising at least or constituted of at least 8 consecutive nucleotides of any one of the nucleic acid sequences SEQ ID Nos: 1961 to 1963 and/or the nucleic acid sequences complementary thereto (nucleotide sequences corresponding to the various variable sequences of the CRISPR1 locus of the serotype Tallahassee);

set S80-2, comprising or constituted of at least one probe comprising at least or constituted of at least 8 consecutive nucleotides of any one of the nucleic acid sequences SEQ ID Nos: 25, 603, 2127, 2133, 1964 to 1966 and/or the nucleic acid sequences complementary thereto (nucleotide sequences corresponding to the various variable sequences of the CRISPR2 locus of the serotype Tallahassee);

set S81-1, comprising or constituted of at least one probe comprising at least or constituted of at least 8 consecutive nucleotides of any one of the nucleic acid sequences SEQ ID Nos: 67, 929, 1967 to 2005 and/or the nucleic acid sequences complementary thereto (nucleotide sequences corresponding to the various variable sequences of the CRISPR1 locus of the serotype Tennessee);

set S81-2, comprising or constituted of at least one probe comprising at least or constituted of at least 8 consecutive nucleotides of any one of the nucleic acid sequences SEQ ID Nos: 24, 769, 1550, 1659, 2006 to 2022 and/or the nucleic acid sequences complementary thereto (nucleotide sequences corresponding to the various variable sequences of the CRISPR2 locus of the serotype Tennessee);

set S82-1, comprising or constituted of at least one probe comprising at least or constituted of at least 8 consecutive nucleotides of the nucleic acid sequence SEQ ID No.: 916 and/or the nucleic acid sequence complementary thereto (nucleotide sequences corresponding to the variable sequence of the CRISPR1 locus of the serotype Urbana);

set S82-2, comprising or constituted of at least one probe comprising at least or constituted of at least 8 consecutive nucleotides of any one of the nucleic acid sequences SEQ ID Nos: 1697, 1698, 1800 and/or the nucleic acid sequences complementary thereto (nucleotide sequences corresponding to the various variable sequences of the CRISPR2 locus of the serotype Urbana);

set S83-1, comprising or constituted of at least one probe comprising at least or constituted of at least 8 consecutive nucleotides of any one of the nucleic acid sequences SEQ ID Nos: 948, 1120, 1123, 1325, 2039 to 2078 and/or the nucleic acid sequences complementary thereto (nucleotide sequences corresponding to the various variable sequences of the CRISPR1 locus of the serotype Weltevreden);

set S83-2, comprising or constituted of at least one probe comprising at least or constituted of at least 8 consecutive nucleotides of any one of the nucleic acid sequences SEQ ID Nos: 254 to 256, 2079 to 2108 and/or the nucleic acid sequences complementary thereto (nucleotide sequences corresponding to the various variable sequences of the CRISPR2 locus of the serotype Weltevreden);

set S84-1, comprising or constituted of at least one probe comprising at least or constituted of at least 8 consecutive nucleotides of any one of the nucleic acid sequences SEQ ID Nos: 1312, 1690, 2141, 2142 and/or the nucleic acid sequences complementary thereto (nucleotide sequences corresponding to the various variable sequences of the CRISPR1 locus of the serotype Zaiman);

set S84-2, comprising or constituted of at least one probe comprising at least or constituted of at least 8 consecutive nucleotides of any one of the nucleic acid sequences SEQ ID Nos: 1697, 1698, 1800, 1924, 2143, 2144 and/or the nucleic acid sequences complementary thereto (nucleotide sequences corresponding to the various variable sequences of the CRISPR2 locus of the serotype Zaiman); and (ii) detection of the hybridized probes.

According to one advantageous mode of this aspect of the invention, when the first two nucleotides (in the 5' position) of said nucleic acid sequences are the dinucleotide "AC" or "AT", then said probes comprise at least or are constituted of at least 8 consecutive nucleotides of these nucleic acid sequences without said nucleotides "AC" or "AT" (i.e., in which said nucleotides "AC" or "AT" are absent), and/or the nucleic acid sequences complementary thereto.

For the purpose of the present invention, the term "at least one probe" is intended to mean one, several or all of the probes of one of the sets of probes defined above.

The term "probe" denotes an oligonucleotide, constituted of at least 8 nucleotides, having the same technical characteristics as a primer (defined above), except that its 3'OH end may not be capable of binding a DNA polymerase. A probe (an oligonucleotide probe) has a specificity of hybridization under suitable conditions (in particular indicated hereinafter) so as to form a hybridization complex with a target nucleic acid. The probes according to the present invention can be synthesized or can be derived from suitable biological preparations according to methods well known to those skilled in the art. Preferably, the probes according to the present invention are DNA and have a length of less than or equal to 150 nucleotides, i.e. less than or equal to 140, 130, 120, 110, 100, 90, 80, 70, 60, 50, 40, 30, 20 or 10 nucleotides. More preferably, the probes according to the present invention have a length of between 8 and 76 nucleotides, preferably between 8 and 34 nucleotides.

According to one advantageous arrangement of the above embodiment, step (b) is carried out by hybridization with at least one probe of each of sets S1-1 to S6-2 (sets of probes for typing and/or subtyping bacteria of the Salmonella genus of serotype Typhimurium, Enteritidis, Hadar, Virchow, Infantis and Typhi).

According to another advantageous arrangement of the above embodiment, step (b) is carried out by hybridization with at least one probe of each of sets S1-1 to S10-2 (sets of probes for typing and/or subtyping bacteria of the Salmonella genus, in addition to those of serotypes mentioned above, those of serotypes Newport, Derby, Kottbus and Indiana).

According to yet another advantageous arrangement of the above embodiment, step (b) is carried out by hybridization with at least one probe of each of sets S1-1 to S44-2 (sets of probes for typing and/or subtyping all the serotypes of bacteria of the Salmonella genus mentioned above).

The subject of the present invention is also a probe or a set of probes capable of identifying a bacterium of the Salmonella genus, each probe comprising at least or being constituted of at least 8 consecutive nucleotides of any one of the nucleic acid sequences selected from the group constituted of the nucleic acid sequences SEQ ID Nos: 1 to 256, 258 to 614, 616 to 876, 878 to 1043, 1045 to 1147, 1149 to 1302, 1304 to 1325, 1333 to 2150 and the nucleic acid sequences complementary thereto.

The probes and primers according to the present invention are capable of hybridizing to a target nucleic acid under stringent conditions as described below or well known to those skilled in the art (see, for example, Sambrook J. et al., Molecular Cloning: A Laboratory Manual. 2000. Third Edition; Ausubel F M. et al., Current Protocols in Molecular Biology, Greene Publishing Assoc. and Wiley-Interscience 1987 & Suppl. 49, 2000). Typically, the parameters that define the stringency conditions depend on the use (i) of a low ionic strength and of a high temperature for the washing, for example 0.015 M sodium chloride/0.0015 M sodium citrate/0.1% sodium dodecyl sulfate (SDS) at 50° C.; (ii) of a denaturing agent during the step of hybridization of the primer or of the probe with a target nucleic acid, such as formamide, for example, 50% (v/v) of formamide with 0.1% of bovine serum albumin (BSA)/0.1% of Ficoll/0.1% of polyvinylpyrrolidone/50 mM sodium phosphate buffer at pH 6.5 with 750 mM sodium chloride, 75 mM sodium citrate at 42° C.; or (iii) of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS and 10% dextran sulfate at 42° C., with washes at 42° C. in 0.2×SSC (sodium chloride/sodium citrate) and 50% formamide at 55° C., followed by a wash under high stringency conditions consisting of 0.1×SSC containing EDTA at 55° C.

According to this advantageous embodiment of the method in accordance with the invention, the amplification product comprising the CRISPR1 and/or CRISPR2 loci is labeled, hybridized to at least one of the probes as defined above and detected. For example, the (PCR) amplification product can be labeled with a cyanin of Cy5 type. The labeled product (i.e. functionally bound to at least one label) is then fragmented, mechanically or chemically, and is then hybridized (for example at a temperature of 42° C.) on a microarray-type chip comprising at least one of the probes as defined above, synthesized in situ. After washing, the hybridization signals are detected (for example using a fluorescence scanner).

The term "label" denotes an atom or a molecule capable of directly or indirectly generating a detectable and/or quantifiable signal, and which can be functionally bonded to a nucleic acid. The signal generated by a label can be detected, for example, by fluorescence, luminescence, radioactivity, colorimetry, gravimetric analysis, X-ray diffraction or absorption, magnetism, enzyme reaction, mass spectrometry, binding affinity, hybridization, radiofrequency or nanocrystals. The nucleic acids are labeled by methods known in themselves to those skilled in the art. By way of example, a nucleic acid can be labeled with a radioisotope (for example, $^{32}P$), a fluorochrome such as the cyanins Cy3 and Cy5, a cold probe such as biotin (dUTP-biotin) (biotin is a ligand for avidin or for streptavidin, which itself can be coupled to a fluorochrome or to an enzyme or taken up by an anti-avidin antibody, the signal of which is amplified). Other alternatives comprise the use of labeling with digoxigenin (dUTP-digoxigenin) revealed with anti-digoxigenin antibodies or by coupling, in the presence of glutaraldehyde, to peroxidase which will be rapidly revealed on an X-ray film by bioluminescence using 3-aminophthalic acid hydrazide (luminol).

The primers and probes according to the invention can also be labeled in such a way that the products of gene amplification or hybridization, respectively, are detected by means of the signal generated by the label to which they are bonded.

The sample according to the invention may be of very varied origin. By way of example, the sample may be a sample of food, human, animal or environmental (earth, water or waste, for example) origin.

Preferably, the sample is an isolated bacterial strain of the *Salmonella* genus.

For the purpose of the present invention, the term "isolated" means that a pure culture of a bacterial strain of the *Salmonella* genus has been obtained from a mixture of bacterial strains or from a sample of food, human, animal or environmental origin. The isolation of a bacterial strain is carried out by conventional methods (for example: streaking technique, suspension-dilution technique), known in themselves to those skilled in the art.

According to one advantageous embodiment in accordance with the invention, the method according to the invention is preceded by a step of extraction of nucleic acids present in said sample. The various bacterial DNA extraction techniques are well known to those skilled in the art.

The subject of the present invention is also a reagent for detecting or identifying the molecular type and subtype of a bacterium of the *Salmonella* genus. Said reagent is selected from the group constituted of at least one set of probes and/or one set of primers as defined above.

The subject of the present invention is also a DNA chip comprising the probes included in at least one or all the set(s) of primers as defined above (S1-1 to S44-2), or the probes included in the sets of probes S1-1 to S10-2, or else the probes included in the sets of probes S1-1 to S6-2.

The term "DNA chip" denotes a set of spots bound to a solid support (for example, glass, silicon, metal, silicone, gel or ceramic slide, or nylon or plastic membrane); each spot independently containing one or more oligonucleotides (for example, the probes of the present invention) which have been deposited thereon or synthesized in situ thereon. DNA chips are known under various names, for instance "biochips", "arrays", "microarrays" or "DNA-microarrays". The spots may range from a few millimeters to a few micrometers in size. A single DNA chip can contain ten or so to several thousand spots, each spot containing a different nucleic acid molecule (for example, a different probe). In general, a composition containing the test DNA is brought into contact with the DNA chip; the hybridization between an oligonucleotide (a probe) and the test DNA (for example, a nucleic acid fragment comprising the *Salmonella* CRISPR1 locus and/or CRISPR2 locus) can then take place under conditions known to those skilled in the art (D. Amaratunga et al., Exploration and Analysis of DNA Microarray and Protein Array Data, John Wiley & Sons, Inc., 2003). The detection of the hybridization then makes it possible to determine the presence of a DNA sequence that is being sought (for example, the variable sequence of a *Salmonella* CRISPR locus).

The subject of the present invention is also a kit or pack for detecting or identifying the molecular type and/or subtype of a bacterium of the *Salmonella* genus, comprising at least one set of primers and/or one set of probes, a reference base as defined above or a part of this reference base, and, optionally, a DNA chip as defined above.

The subject of the present invention is also the use of a set of primers, of a set of probes, or of a DNA chip as defined above, for detecting or identifying the molecular type and/or subtype of a bacteria of the *Salmonella* genus.

In addition to the above arrangements, the invention also comprises other arrangements, which will emerge from the description that follows, which refers to exemplary embodiments of the method which is the subject of the present invention and also to the attached drawings, in which:

FIG. 1 represents diagrammatically the separate gene amplification (FIG. 1A) or gene amplification during the same reaction (FIG. 1B) of the *Salmonella* CRISPR1 and CRISPR2 loci.

Figure 2A:
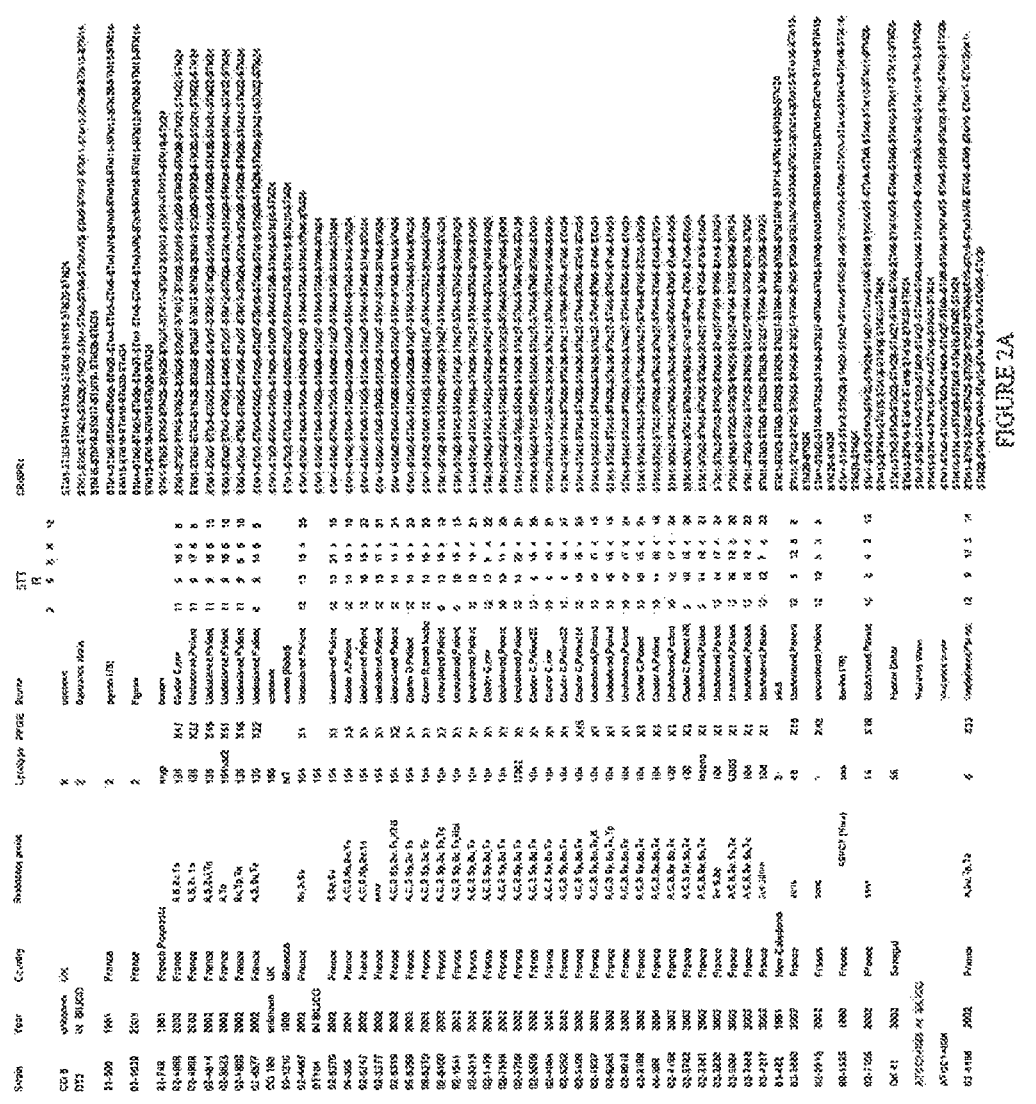
Figure 2A:
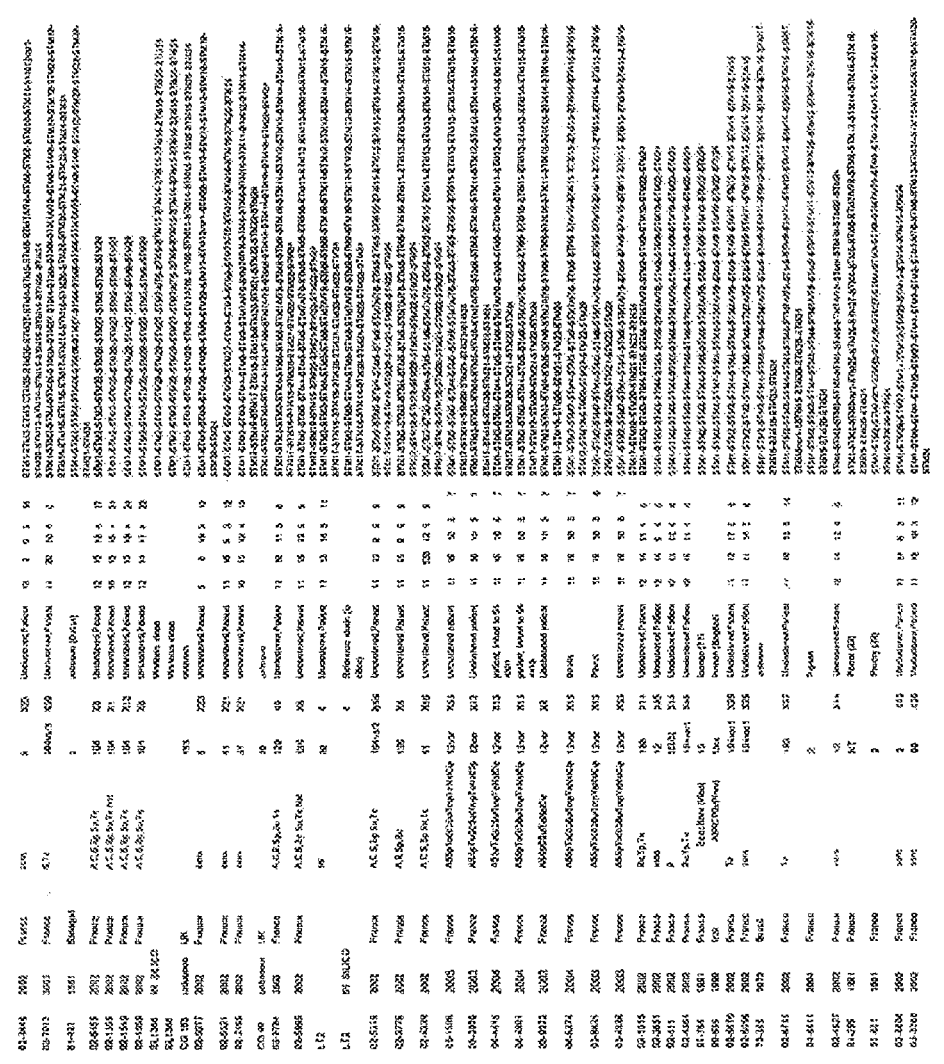
Figure 2B:
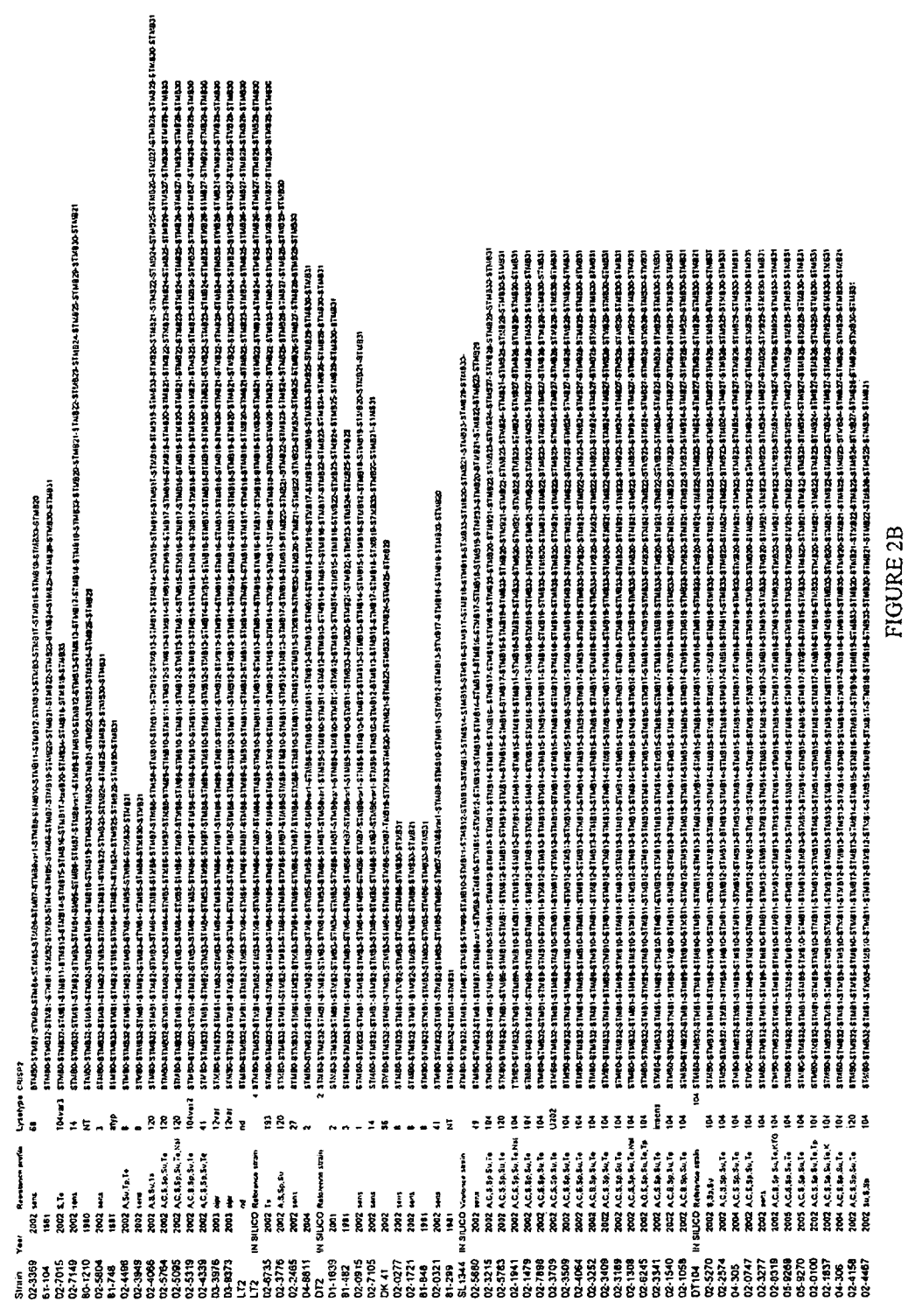

FIG. 2 indicates the variable-sequence (spacer) composition of the CRISPR1 (FIG. 2A) and CRISPR2 (FIG. 2B) loci of 91 strains of *Salmonella* of serotype Typhimurium. Also represented are the results of the conventional subtyping: antibiotype (A=amoxicillin, C=chloramphenicol, Cip=ciprofloxacin, G=gentamicin, K=kanamycin, Nal=nalidixic acid, S=streptomycin, Sp=spectinomycin, Su or Sul=sulfamides, T or To=tobramycin, Te=tetracycline, Tp or Tmp=trimethoprim, sens=sensitive), lysotype (Anderson et al., 1977, J. Hyg. (Lond) 78, 297-300), pulse-field electrophoresis profile (PFGE, method described in Weill et al., 2006, J. Clin. Microbiol. 44, 700-708; Weill et al., 2004, J. Clin. Microbiol. 42, 2432-2437), STTR (type according to the "Multiple-Locus Variable-Number Tandem Repeat Analysis" method, said method being described in Lindstedt et al., (2003, J. Clin. Microbiol. 41, 1469-1479)) and epidemiological data (of human or animal origin).

Figure 3:
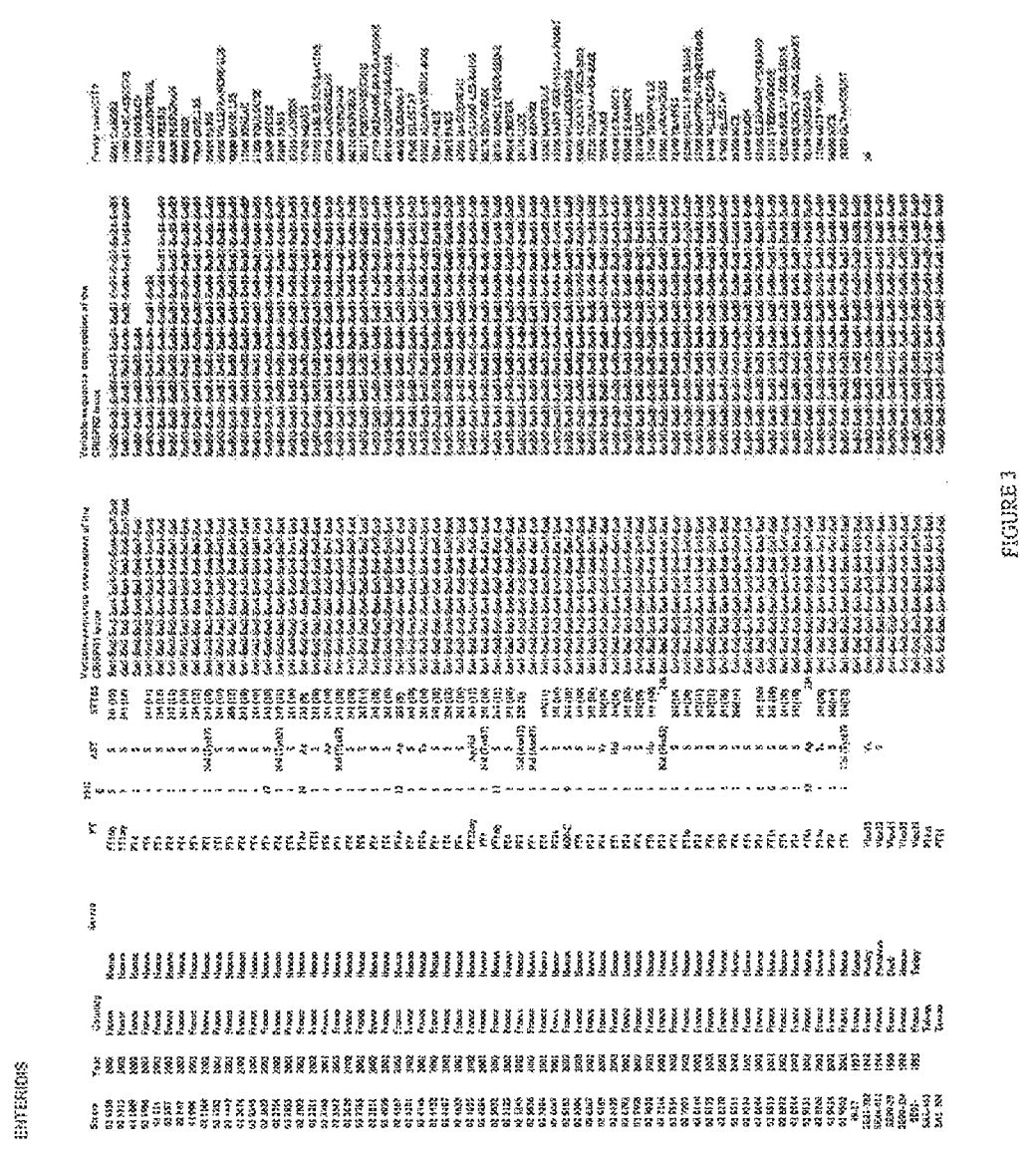
Figure 3:
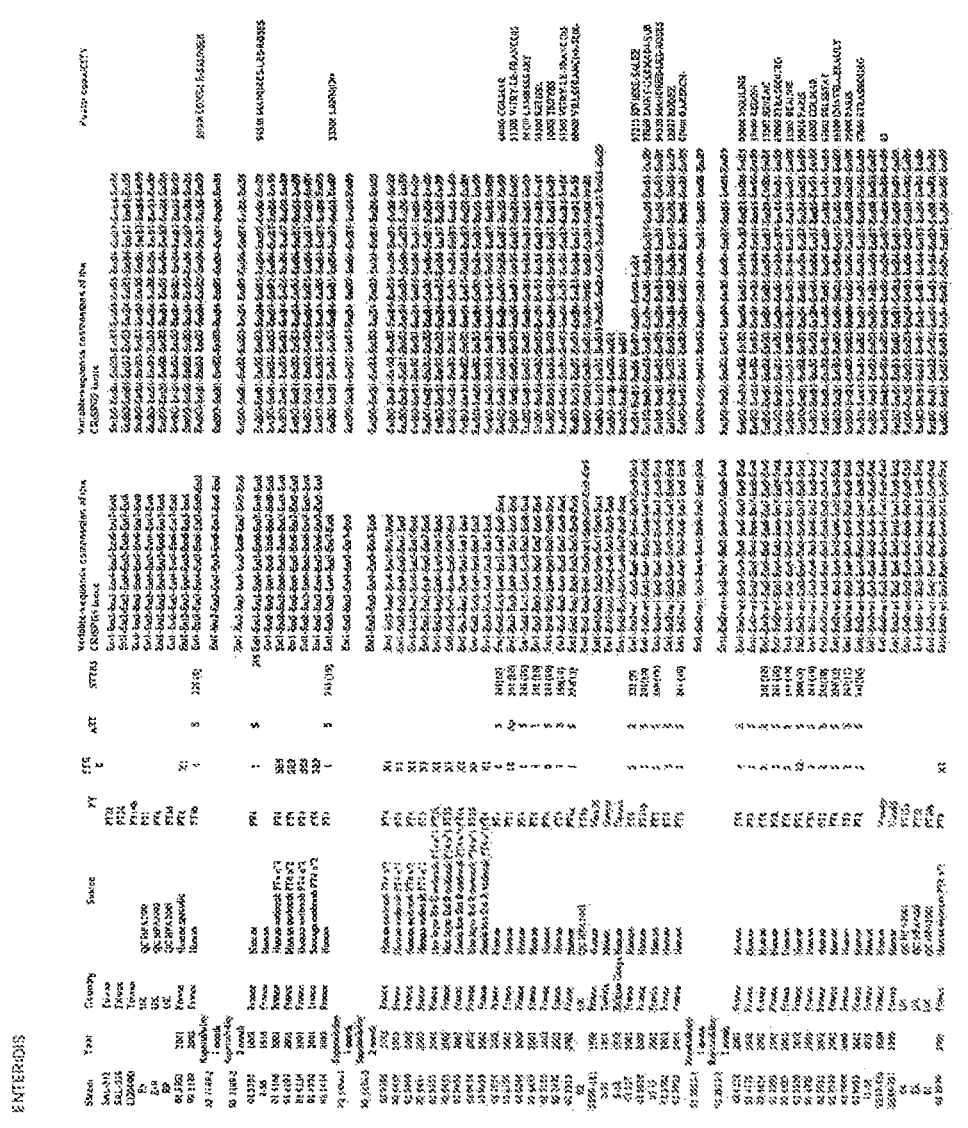
Figure 3:
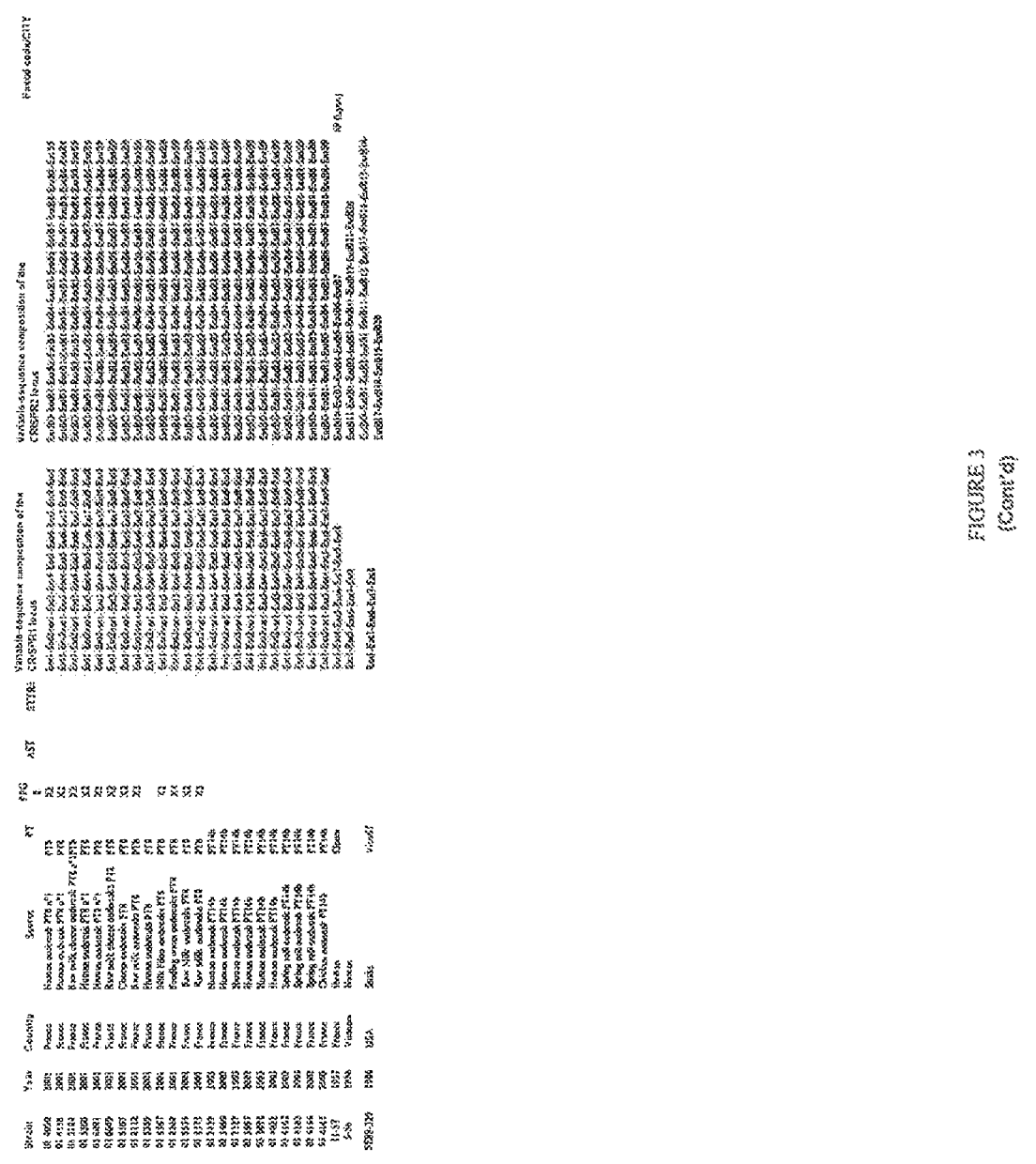
Figure 3A:
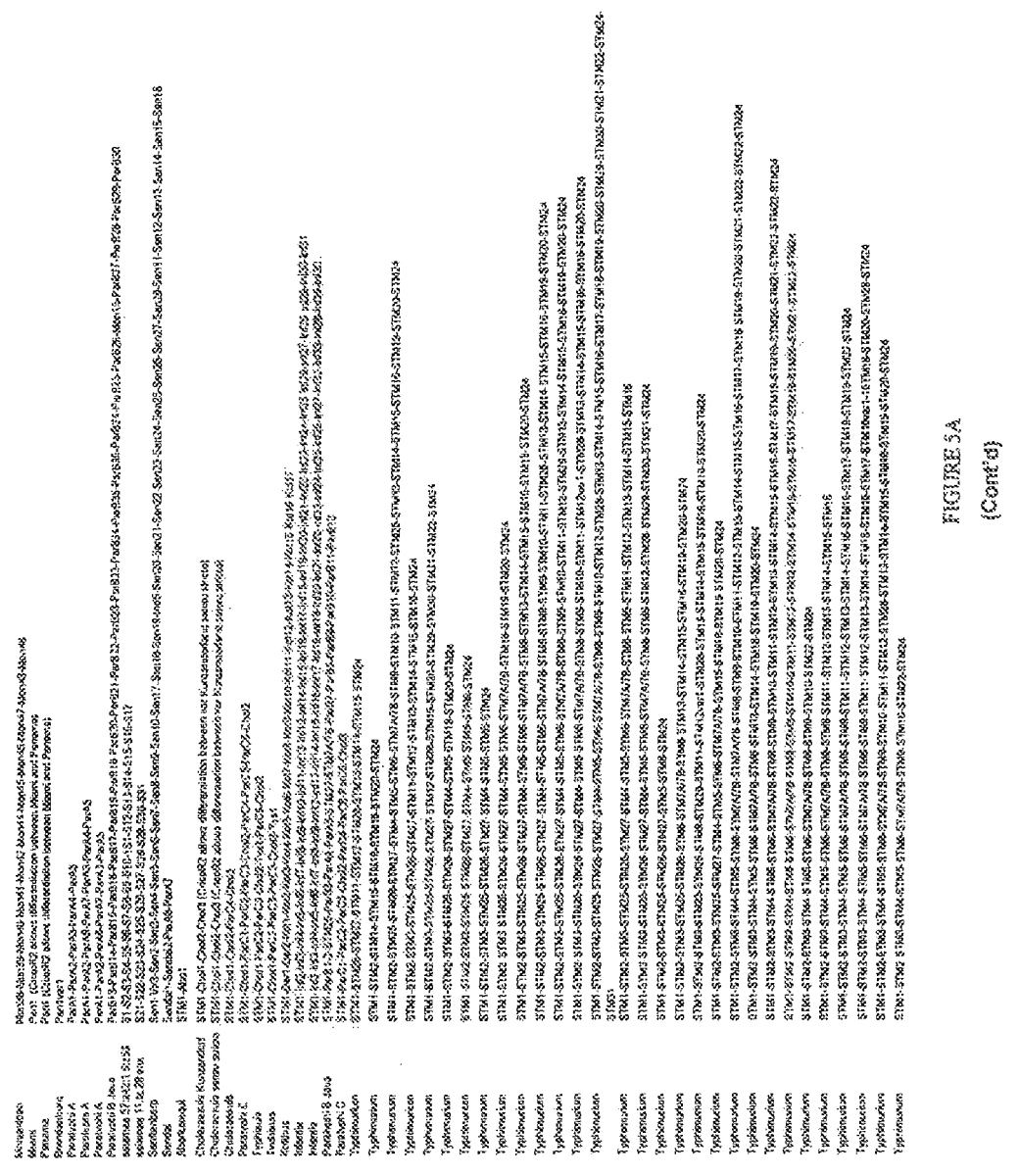
Figure 3A:
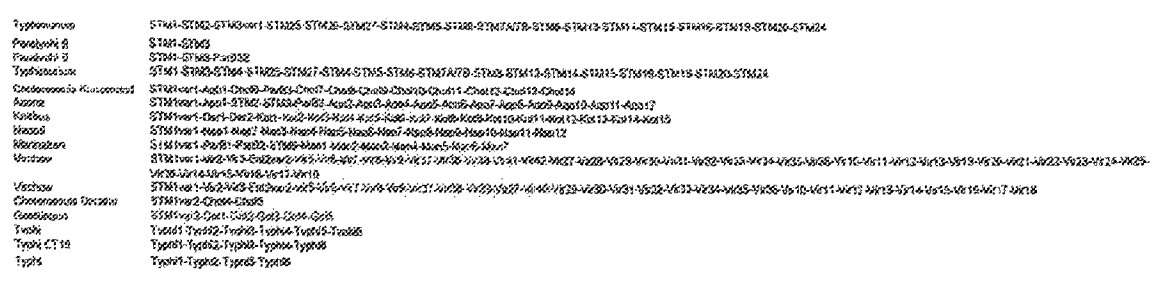

FIG. 3 indicates the variable-sequence (spacer) composition of the CRISPR1 (FIG. 3A) and CRISPR2 (FIG. 3B) loci at 154 strains of *Salmonella* of serotype Enteritidis. Also represented are the results of the conventional subtyping and epidemiological data (legend identical to that of FIG. 2).

Figure 4A:
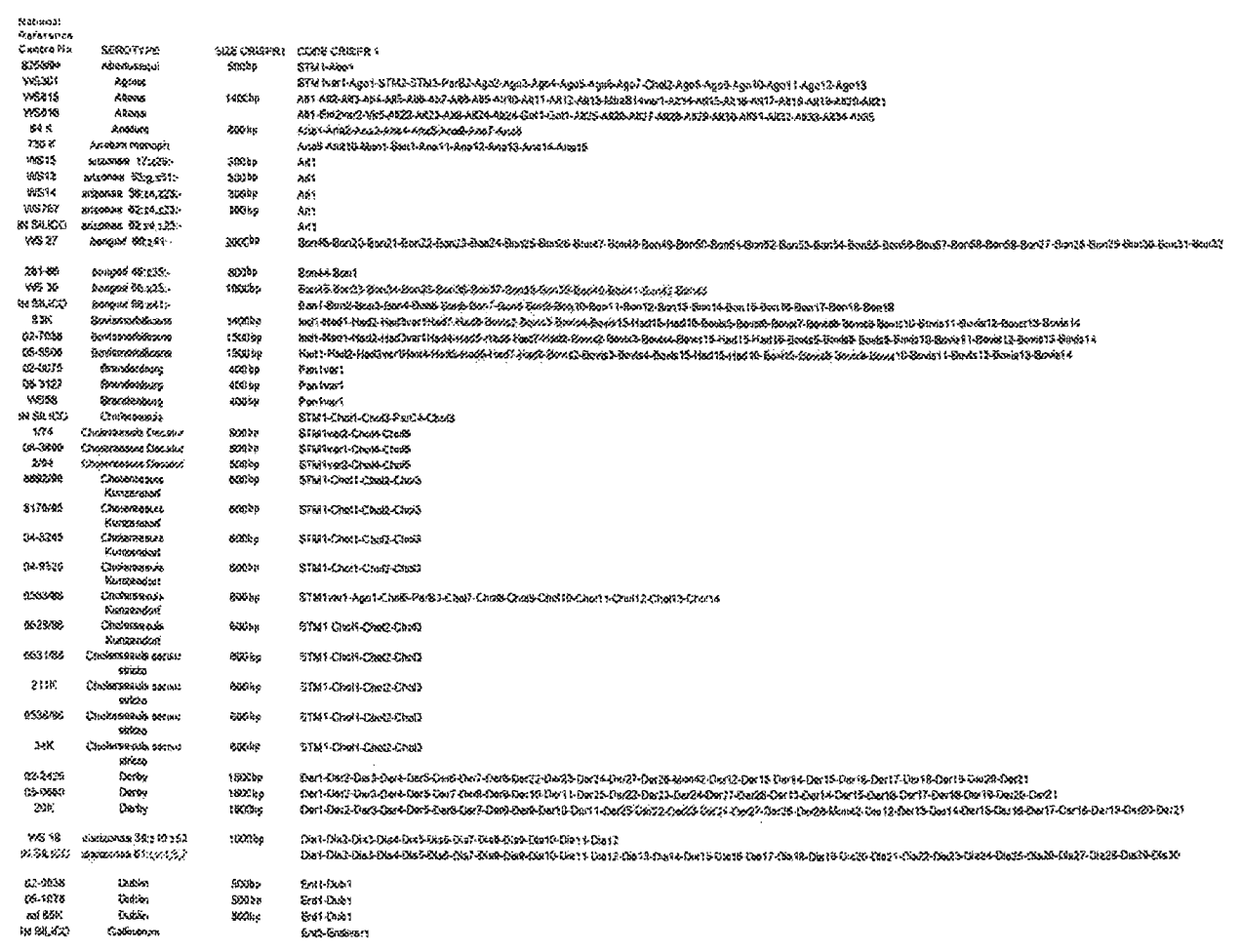
Figure 4A:
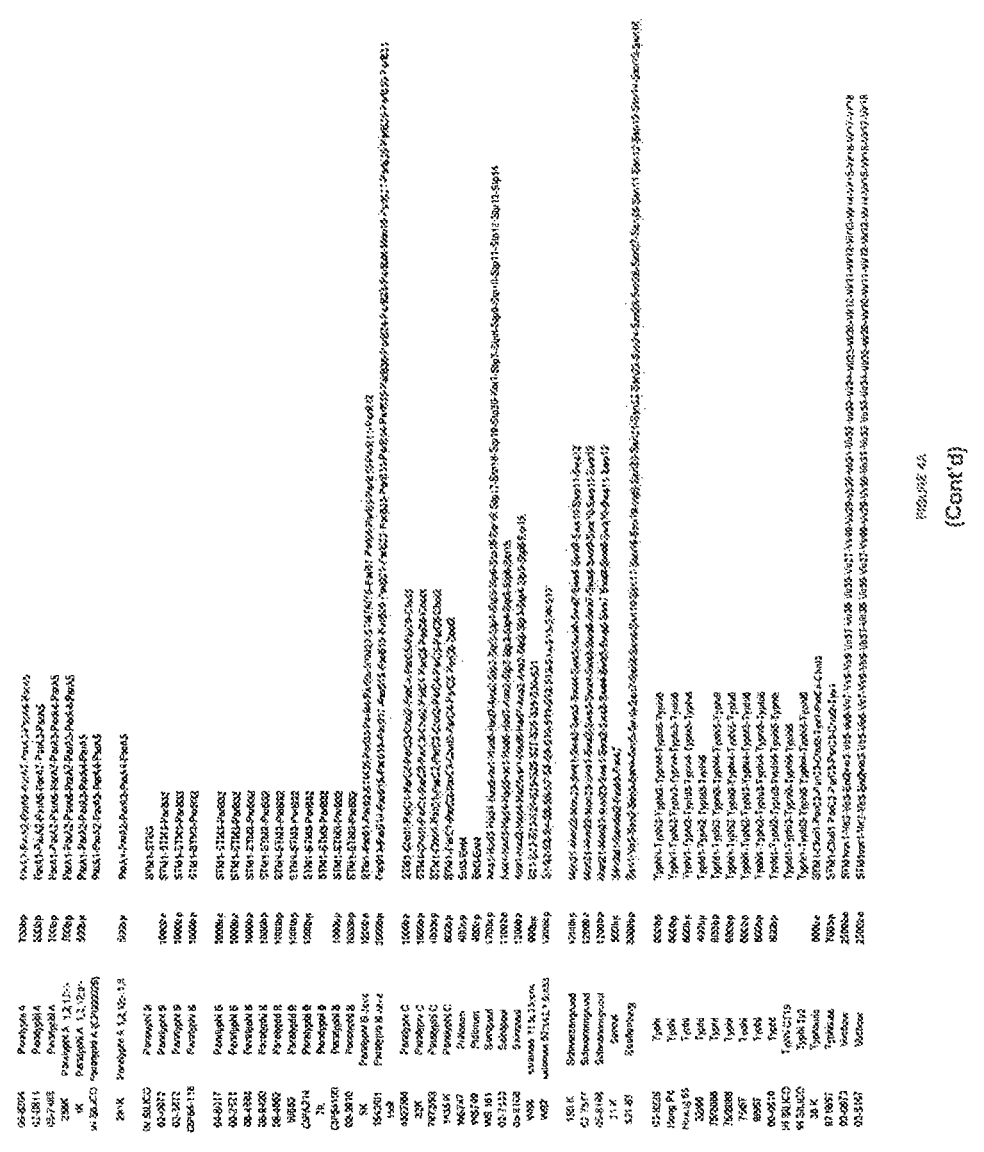
Figure 4B:
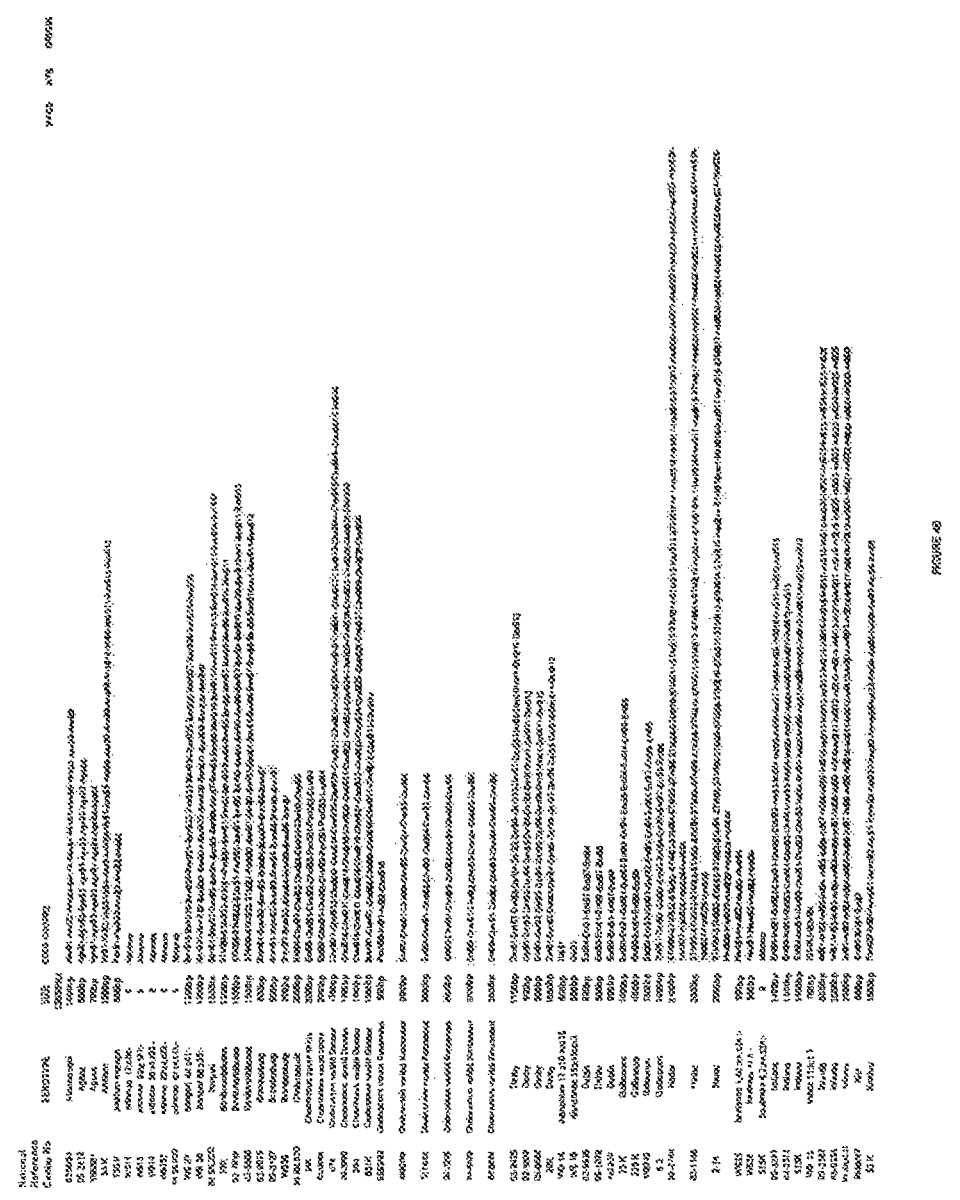
Figure 4:
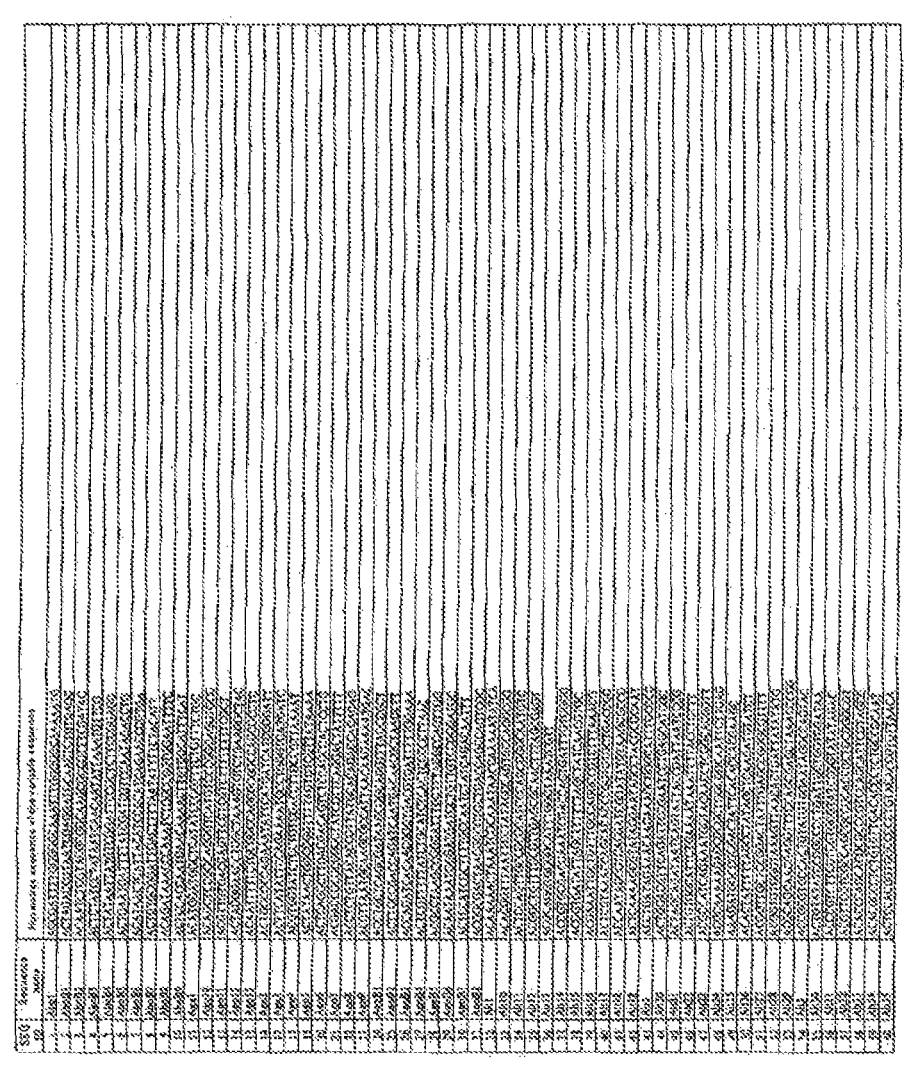

FIG. 4 indicates the variable-sequence (spacer) composition of the CRISPR1 (FIG. 4A) and CRISPR2 (FIG. 4B) loci, respectively of 95 and 85 strains of *Salmonella* belonging neither to the serotype Typhimurium nor to the serotype Enteritidis. Also represented are the results of the conventional subtyping and epidemiological data (sporadic cases, epidemic cases and origin of isolates).

Figure 5B:
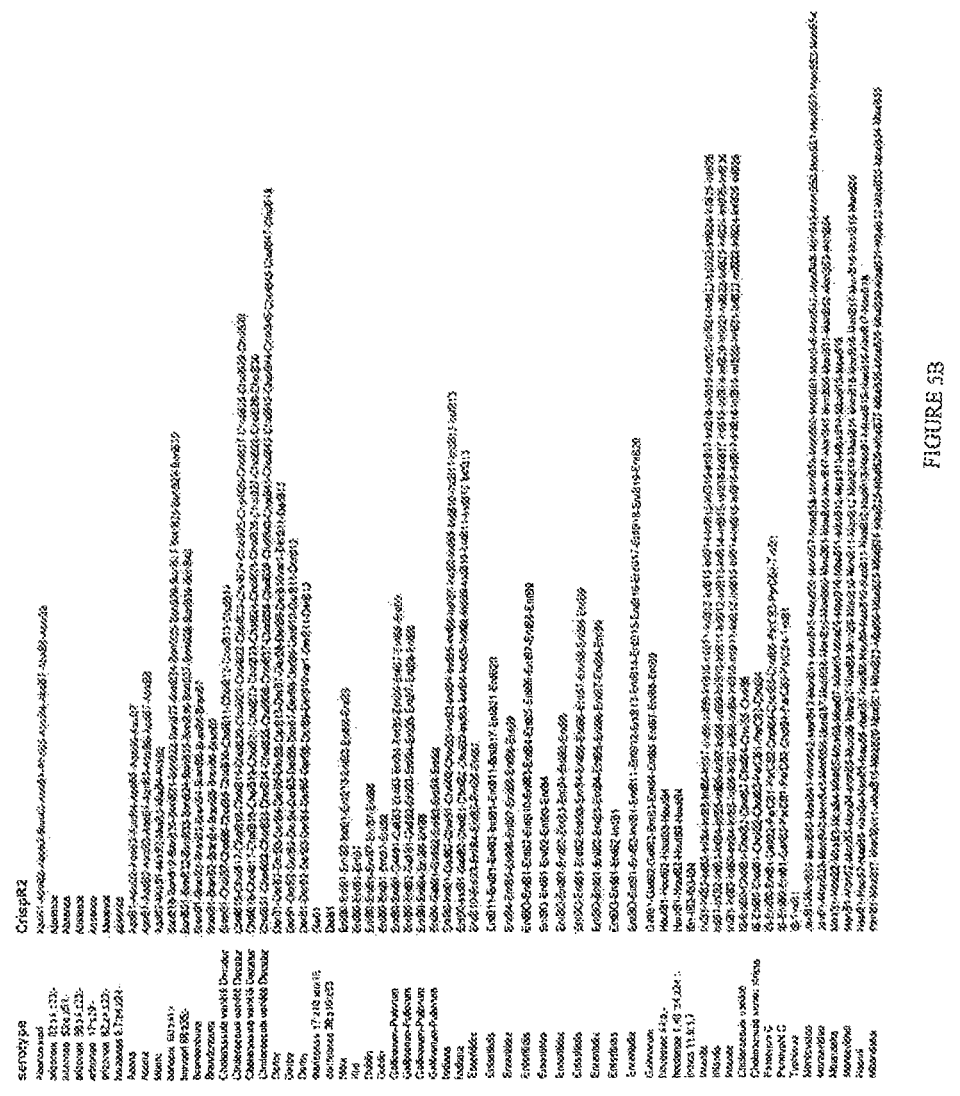
Figure 5B:
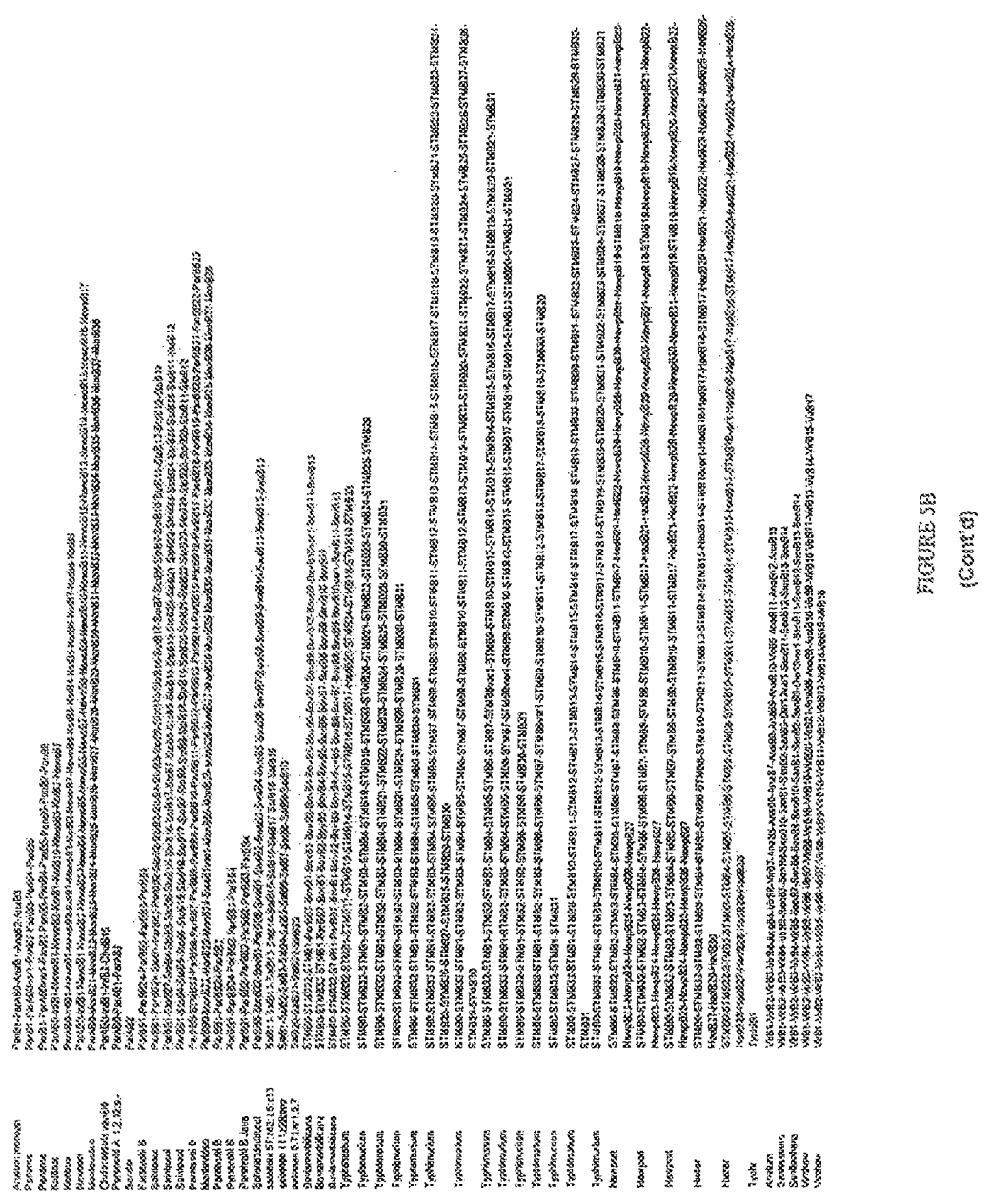

FIG. 5 shows the variation in the variable-sequence composition of CRISPR1 (FIG. 5A) and CRISPR2 (FIG. 5B) of some *Salmonella* strain serotypes.

FIGS. 6A and 6B represent the result of the sequencing (5'-3') of the CRISPR1 (SEQ ID NO: 2153) and CRISPR2 (SEQ ID NO: 2154) loci, respectively, of a *Salmonella* strain to be identified. The repeat sequences or direct repeats (DR) are shaded (the variable nucleotides within the DRs are represented in bold and italics). The variable sequences (spacers) are boxed in.

FIGS. 7A and 7B represent the result of the sequencing (5'-3') of the CRISPR1SEQ ID NO: 2155) and CRISPR2 (SEQ ID NO: 2156) loci, respectively, of a Salmonella strain to be identified (legend identical to that of FIG. 6).

Figure 9:
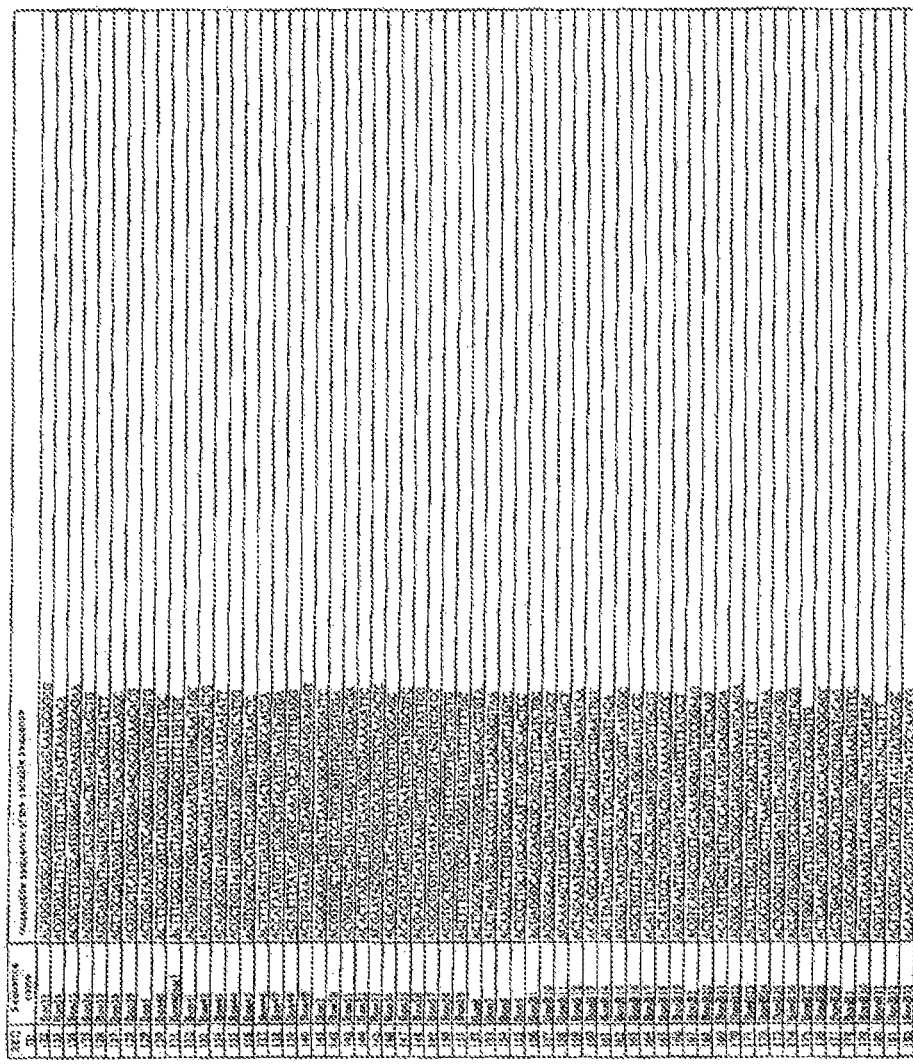
Figure 9:
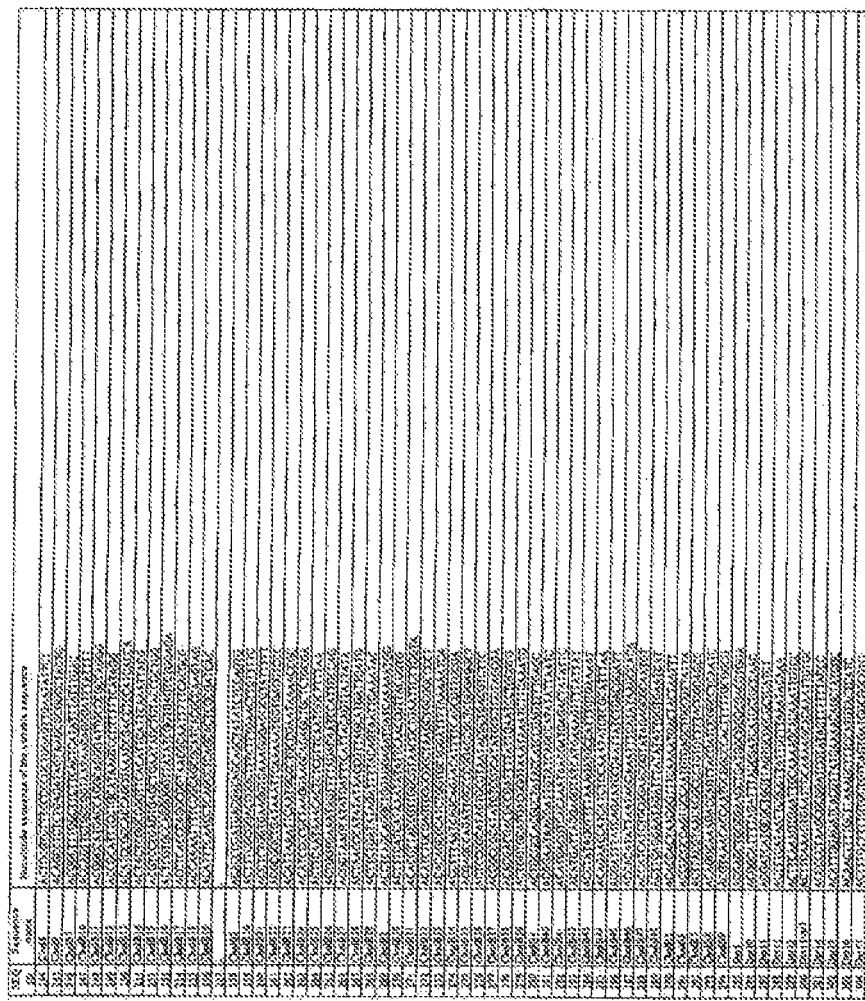

FIG. 9 indicates, for each variable sequence of the *Salmonella* CRISPR loci, the name which has been assigned thereto.

Figure 10A:
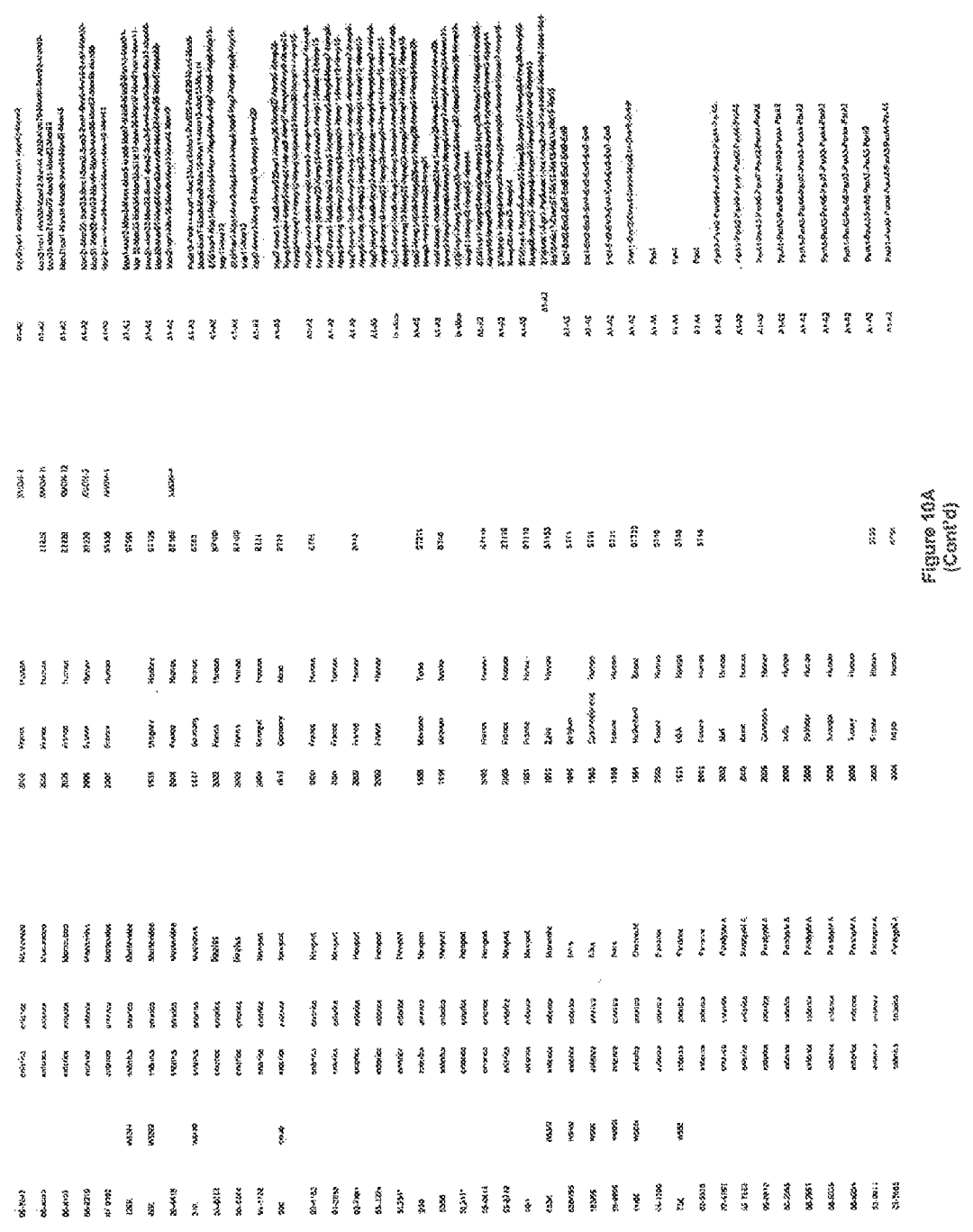
Figure 10B:
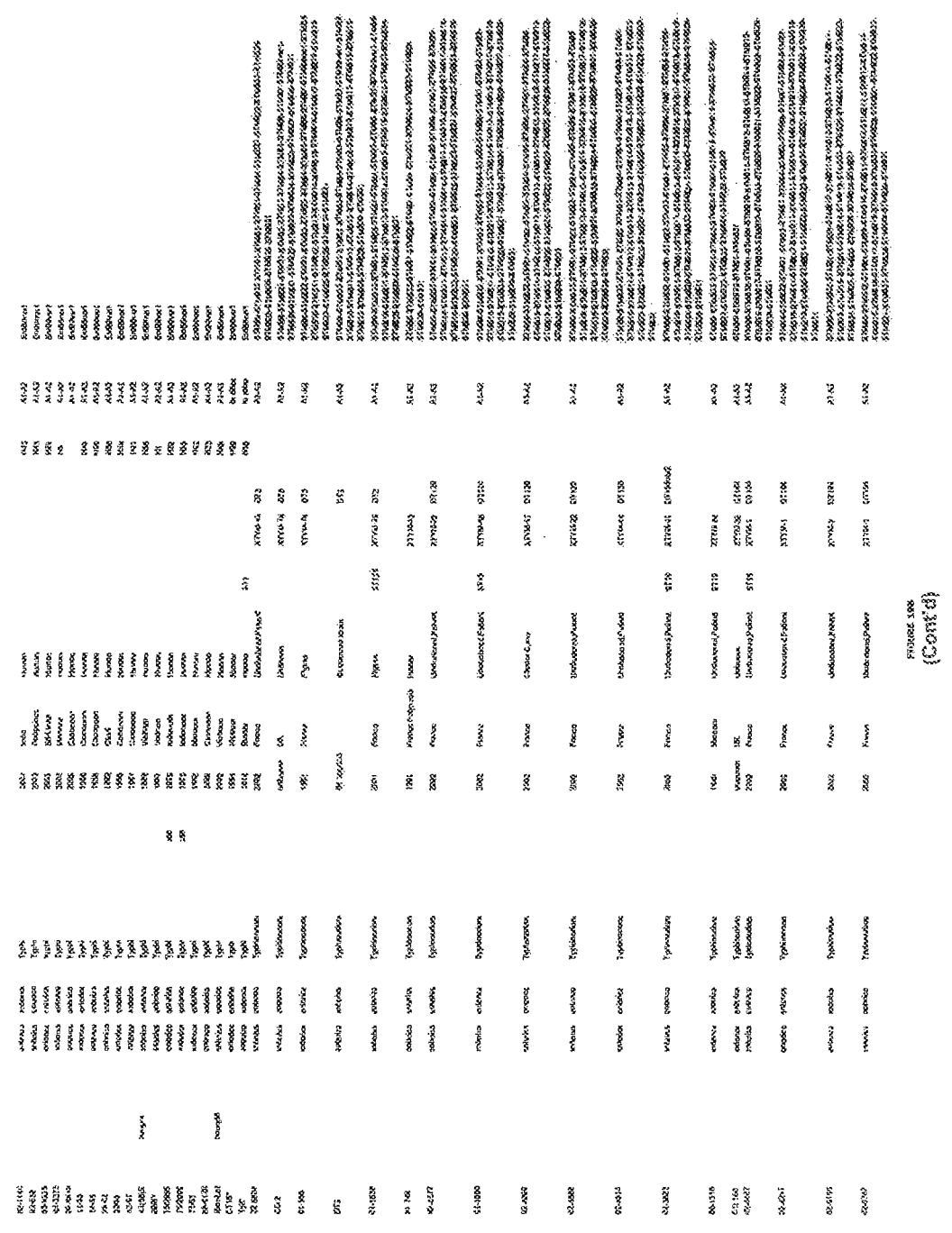

FIG. 10 indicates the variable-sequence (spacer) composition of the CRISPR1 (FIG. 10A) and CRISPR2 (FIG. 10B)

loci of 564 *Salmonella* strains. Also represented are the results of the conventional subtyping and epidemiological data (legend identical to that of FIG. 2). This comprises the variable-sequence composition of the CRISPR1 and CRISPR2 loci of types and subtypes of bacteria of the *Salmonella* genus, listed in FIGS. 2, 3 and 4.

It should be clearly understood that these examples are given only by way of illustration of the subject of the invention, of which they in no way constitute a limitation.

EXAMPLE 1

Forming of the Reference Base Listing the Composition of the Variable Sequences of the Two Loci CRISPR1 and CRISPR2 of *Salmonella*

1) Materials and Methods
1-1) Design of the Oligonucleotide Primers for Amplifying the CRISPR1 and/or CRISPR2 Loci in *Salmonella*
The primers, capable of amplifying the CRISPR1 and/or CRISPR2 loci of bacteria of the *Salmonella* genus, were designed on the basis of the genomic sequences of:
- *S. enterica* serotype Typhimurium LT2 (genome available under number AE008834 in the GenBank database, dated Aug. 9, 2005),
- *S. enterica* subsp. *enterica* serotype Choleraesuis strain SC-B67 (genome available under number AE017220 in the GenBank database, dated Jan. 11, 2006),
- *S. enterica* subsp. *enterica* serotype Paratyphi A strain ATCC 9150 (genome available under number CP000026 in the GenBank database, dated Apr. 8, 2005),
- *S. enterica* serotype Typhi strain CT18 (genome available under number AL627276 in the GenBank database, dated Nov. 14, 2006),
- *S. enterica* serotype Enteritidis PT4 NCTC 13349 (genome available on the Internet site of the Sanger Institute at the following address: http://www.sanger.ac.uk/Projects/Salmonella/),
- *S. bongori* 12419 ATCC 43975 (genome available on the Internet site of the Sanger Institute at the following address: http://www.sanger.ac.uk/Projects/*Salmonella*/, and at the following link: http://genome.wustl.edu/sub_genome_group.cgi?GROUP=3&SUB_GROUP=3),
- *S. enterica* subsp. *arizonae* serotype 62:z4,z23:– (genome available under number CP000880 in the GenBank database, dated Nov. 28, 2007), and *S. enterica* subsp. *diarizonae* serotype 61:1,v:1,5,7 (genomes available on the Internet at the following link: http://genome.wustl.edu/sub_genome_group.cgi?GROUP=3&SUB_GROUP=3).

Primers Capable of Amplifying the CRISPR1 Locus:
The position of the nucleotides is given with reference to the genome of *S. enterica* serotype Typhimurium LT2, available under number AE008834 in the GenBank database, dated Aug. 9, 2005, or of *S. enterica* serotype Typhi CT18, available under number AL627276 in the GenBank database, dated Nov. 14, 2006.

Forward primer called SALCRISP1-FB (=A1) (position of nucleotides: AE008834, 1109-1128):

(SEQ ID No.: 1326)
5'-GT(A/G)GT(A/G)CGGATAATGCTGCC-3'

Reverse primer called SALCRISP1-RB (=A2) (position of nucleotides: AE008834, 2878-2856):

(SEQ ID No.: 1327)
5'-CGTATTCCGGTAGAT(G/C/T)T(A/G/T)GATGG-3'

Primer called AriParaB-R (=A3) (reverse) (position of nucleotides: AE008834, 10289-10310): 5'-CTATTTTGG(A/G)CT(A/G)CCGAC(A/G)ATG-3'(SEQ ID No.: 1328)
This primer serves to amplify the *Salmonella* strains of the *arizonae* subspecies, the septicemic strains of serotype Paratyphi B, some strains of the *indica* subspecies, and the majority of the strains of serotype Mbandaka. These strains have a deletion downstream of the CRISPR1 locus.
Primer called BrPanCR1-R (=A4) (reverse) (position of nucleotides: AL627276, 232226-232206): 5'-GCAATCG-GAGCGATTGATGGC-3' (SEQ ID No.: 1329)
This primer serves to amplify the strains of serotypes Brandenburg and Panama. These strains have a deletion downstream of the CRISPR1 locus.
Primer called 50K (=A5) (reverse) (position of nucleotides: AL627276, 233322-233341): 5'-TCAACACTCTCT-TCACCCAG-3' (SEQ ID No: 2151).
This primer serves to amplify some of the serotypes Newport and Bardo.
Primer called HoutWS24R A6) (reverse) (position of nucleotides: AL627276 (233298-233017): 5'-TAACCAGC-CCTCTTCTGCCTG-3' (SEQ ID No.: 2152)
This primer serves to amplify certain strains of the *houtenae* subspecies.

Primers Capable of Amplifying the CRISPR2 Locus:
The position of the nucleotides is given with reference to the genome of *S. enterica* serotype Typhimurium LT2, available under number AE008834 or AE008835 in the GenBank database, dated Aug. 9, 2005.

Forward primer called SALCRISP2-FB (=B1) (position of nucleotides: AE008834, 18727-18751):

(SEQ ID No.: 1330)
5'-GAGCAATAC(C/T)(C/T)T(A/G)ATCGTTAACGCC-3'

(region missing in the *S. arizonae* subspecies).

Reverse primer 1 called SALCRISP2-RA (=B2) (position of nucleotides: AE008835, 931-906): 5'-GTTGC(A/G/T)ATA(G/T)GT(C/T)G(A/G)T(A/G)G(A/G)ATGT(A/G)G-3' (SEQ ID No.: 1331) (region missing in the *diarizonae* subspecies).

Reverse primer 2 called SALCRISP2-RB (=B3) (position of nucleotides: AE008835, 1205-1185):

(SEQ ID No.: 1332)
5'-CTGGCGGCTGTCTATGCAAAC-3'.

This sequence has, however, a mismatch in *S. enterica* serotype Typhimurium LT2 at position 1201.
1-2) Amplification of the CRISPR1 and CRISPR2 Loci
1-2-1) *Salmonella* Strains Used
The *Salmonella* strains analyzed come from the Centre National de Reference des *Salmonella* [National *Salmonella* Reference Center] and from the Centre Collaborateur OMS des *Salmonella* [WHO Collaborating Center for *Salmonella*], Emergent Pathogenic Bacteria Biodiversity Unit, 25 rue du Docteur Roux, 75724 Paris, Cedex 15. The strains are of human or animal or food origin, isolated from 1885 to 2005. They come from sporadic cases or were collected during investigated epidemics.

564 strains belonging to 86 serotypes of the 2 species and 6 subspecies of *Salmonella* were analyzed (between parentheses, the number of strains analyzed):

i) the species *S. enterica*
subspecies *enterica*:

serotypes Abony (1), Abortusequi (1), Aesch (1), Agona (12), Albany (1), Altona (2), Anatum (3), Arechavalata (1), Bardo (1), Berta (1), Bispebjerg (1), Blegdam (1), Bovismorbificans (3), Brandenburg (3), Chester (1), Choleraesuis variety Decatur (3), Choleraesuis (1), Choleraesuis variety Kunzendorf (9), Choleraesuis sensu stricto (2), Concord (1), Crossness (1), Derby (4), Dublin (6), Duesseldorf (1), Emek (2), Enteritidis (173), Fulica (1), Gallinarum variety Duisburg (1), Gallinarum variety Gallinarum (4), Gallinarum variety Pullorum (2), Goettingen (1). Gueuletapee (1), Hadar (5), Heidelberg (6), Hessarek (1), Indiana (3), Infantis (4), Itami (1), Javiana (4), Johannesburg (1), Kentucky (2), Kiel (3), Kottbus (2), Kundunchi (1), Lindenburg (1), Manhattan (8), Maracaibo (1), Mbandaka (2), Miami (1), Mississippi (1), Montevideo (12), Muenchen (1), Napoli (2), Newport (13), Niarembe (1), Nitra (3), Overvecht (1), Panama (3), Paratyphi A (14), Paratyphi B (35), Paratyphi C (4), Poona (1), Potsdam (1), Reading (1), Rosenberg (1), Rubislaw (1), Saintpaul (5), Sandiego (1), Schwarzengrund (5), Sendai (1), Senftenberg (3), Stourbridge (6), Tallahassee (1), Tennessee (1), Typhi (20), Typhimurium (104), Typhisuis (1), Urbana (1), Virchow (4), Weltevreden (2), Zaiman (1), subspecies *salamae*:
serotypes 11:1,z28:e,n,x (1), 57:z42:1,6:Rz53 (1), 6,7:1,w: 1,5,7 (1), subspecies *arizonae*:
serotypes 62:z4,z23:– (2), 53:g,z51:– (1), 56:z4,z23:– (1), 17:z29:– (1), subspecies *diarizonae*:
serotypes 38:z10:z53 (1), 61:1,v:1,5,7 (1), subspecies *houtenae*:
serotypes 6,7:z4,z24:– (1), 44:a:–(1), 1,40:z4,z24:– (1), subspecies *indica*:
serotypes 11:b:1,7 (1), 6,7:z41:1,7 (1);

ii) the species *bongori*
serotypes 60:z41:– (1), 66:z35:– (1), 48:z35:– (1), 66:z41:– (1).

1-2-2) Extraction of *Salmonella* DNA

The DNA was extracted using the Instagene Matrix kit (BioRad) or the Wizard kit (Proméga) by following the manufacturer's instructions.

1-2-3) Gene Amplification Reactions

The *Salmonella* CRISPR1 and CRISPR2 loci were amplified either separately (FIG. 1A) or during the same reaction (FIG. 1B), by polymerase chain reaction (PCR).

1-2-3-1) Separate Gene Amplification of the two Loci CRISPR1 and CRISPR2 a) Primers Used:

Primers used for amplifying the CRISPR1 locus by multiplex PCR:

SALCRISP1-FB (SEQ ID No.: 1326)
and

SALCRISP1-RB, (SEQ ID No.: 1327)

AriParaB-R, (SEQ ID No.: 1328)

BrPanCR1-R, (SEQ ID No.: 1329)

50K (SEQ ID No.: 2151)
and

HoutWS24R. (SEQ ID No.: 2152)

Primers used to amplify the CRISPR2 locus by multiplex PCR:

SALCRISP2-FB, (SEQ ID No.: 1330)

SALCRISP2-RA (SEQ ID No.: 1331)
and

SALCRISP2-RB. (SEQ ID No.: 1332)

b) Reaction Mix:
DNA, extracted according to the method above, diluted to 1/10: 2 µl
Primers: 10 pmol for each primer
Deoxynucleoside triphosphates: 100 µM
Taq DNA polymerase (Ampli Taq Gold, Roche): 0.85 U
10× buffer (Roche): 10%
$MgCl_2$ (Roche): 1.5 mM
DMSO (Sigma): 5%
Pure water of molecular biology quality qs: 50 µl c) Amplification Conditions for the Two Loci:
94° C., 10 min (one cycle)
94° C., 1 min; 59° C., 1 min; 72° C., 1 min 30 s (35 cycles)
72° C. 10 min (one cycle).

d) Electrophoretic Separation of the Amplification Products

Loading of the samples (per well): 5 µl of PCR amplification product with 1 µl of 6× loading buffer added (loading buffer: 0.25% bromophenol blue; 0.25% xylene cyanol; 30% glycerol).

Markers used: 100 by DNA ladder and 1 kb DNA ladder (Biolabs, New England).

Migration Conditions:
Loading onto a 1% agarose gel in 0.5×TBE [45 mM Tris HCl (pH 8); 45 mM boric acid; 10 mM EDTA (pH 8)].

Horizontal electrophoresis in 0.5×TBE at 100 V for 40 min.

Photograph taken after staining with ethidium bromide for 15 min.

1-2-3-2) Gene Amplification of the Two Loci CRISPR1 and CRISPR2 During the Same Amplification Reaction The gene amplification of the two loci CRISPR1 and CRISPR2 was carried out in a single step using the Expend Long Template PCR System (Roche).

a) Primers Used:

SALCRISP1-FB (SEQ ID No.: 1326)
and

SALCRISP2-RB (SEQ ID No.: 1332)

b) Reaction Mix:
DNA, extracted according to the method 2.5 µl above, pure:
Primers: 0.3 µM for each primer
Deoxynucleoside triphosphates: 0.5 mM
Taq DNA polymerase (provided with the kit): 3.75 U
10× buffer 2 (provided with the kit): 10%
Pure water of molecular biology quality qs: 50 µl c) Amplification Conditions for the Two Loci:
94° C., 2 min (one cycle)
94° C., 10 s; 58° C., 30 s; 68° C., 15 min (10 cycles)
94° C., 10 s; 58° C., 30 s; 68° C., 15 min, with an increase of 20 s in each cycle (20 cycles)
72° C., 7 min (one cycle)

d) Electrophoretic Separation of the Amplification Products

Loading of the samples (per well): 5 µl of PCR amplification product with 1 µl of 6× loading buffer added (loading buffer: 0.25% bromophenol blue; 0.25% xylene cyanol; 30% glycerol).

Markers used: Raoul™ (Qbiogene).

Migration Conditions:

Loading onto a 0.75% agarose gel in 0.5×TBE [45 mM Tris HCl (pH 8); 45 mM boric acid; 10 mM EDTA (pH 8)].

Horizontal electrophoresis in 0.5×TBE at 100 V for 3 hours.

Photograph taken after staining with ethidium bromide for 15 min.

2) Amplification Results 2-1) Amplification of the CRISPR1 Locus

The CRISPR1 locus of all the strains listed in FIG. 10 (with the exception of two *houtenae* strains, since they do not contain the CRISPR1 locus) was amplified using the primers SALCRISP1-FB (SEQ ID No.: 1326), SALCRISP1-RB (SEQ ID No.: 1327), AriParaB-R (SEQ ID No.: 1328), BrPanCR1-R (SEQ ID No.: 1329), 50K (SEQ ID No.: 2151) and HoutWS24R (SEQ ID No.: 2152); the size of the amplicons is between 400 by and 3000 bp.

2-2) Amplification of the CRISPR2 Locus

The CRISPR2 locus of all the strains listed in FIG. 10, with the exception of the strains below which do not possess the CRISPR2 locus, was amplified; the size of the amplicons is between 400 by and 3000 bp:

*S. enterica* subsp. *arizonae* serotypes 62:z4,z23:–, 53:g,z51:–, 56:z4,z23:–, 17:z29:–

*S. enterica* subsp. *diarizonae* serotypes 61:1,v:1,5,7

*S. enterica* subsp. *houtenae* serotypes 6,7:z4,z24:–

*S. enterica* subsp. *indica* serotypes 6,7:z41:1,7.

It is noted that the serotypes for which no amplification of the CRISPR2 locus was obtained could be amplified by the gene amplification method in a single step (cf. below).

2-3) Amplification of the CRISPR1 and CRISPR2 Loci During the Same Reaction

The CRISPR1 and CRISPR2 loci of the following serotypes were amplified simultaneously. The size of the amplicons is between 8 and 20 kb (for example, it is 20 kb for the region containing the two complete loci of *S. enterica* serotype Typhimurium LT2):

i S. enterica subsp. *enterica* of the serotypes Brandenburg and Panama

*S. enterica* subsp. *arizonae* serotypes 62:z4,z23 53:g,z51 56:z4.z23:–, 17:z29:–

*S. enterica* subsp. *diarizonae* serotypes 61:1,v:1,5,7

*S. enterica* subsp. *houtenae* serotypes 6,7:z4.z24:–, 44:a:–.

3) Sequencing of PCR Products

All the PCR amplification products were sequenced according to a method known to those skilled in the art, using the BigDye version 3.1 chemistry kit (Applied Biosystems, Foster City, Calif.) and an ABI 3700 instrument (Applied Biosystems).

4) Nucleotide Sequence Analysis and Variable-sequence Extraction

The nucleotide sequences were analyzed manually. The nucleotide sequences of the variable sequences (spacers) were extracted and also their order within the two CRISPR loci. A name was given to each variable sequence according to the serotype in which it was identified for the first time. All the variable sequences inventoried are listed in the sequence listing (sequences SEQ ID No.: 1 to 256, 258 to 614, 616 to 876, 878 to 1043, 1045 to 1147, 1149 to 1302, 1304 to 1325, 1333 to 2150) and in FIG. 9.

5) Correlation Between the Variable-sequence Composition and the Serotype and Subtype FIGS. 2, 3, 4, 5 and 10 (FIG. 10 also comprises the strains listed in FIGS. 2, 3, 4 and 5) give the variable-sequence (spacer) composition of the *Salmonella* strains analyzed. Also mentioned, in particular for the two main serotypes, Typhimurium and Enteritidis, are the results of the conventional subtyping (lysotype, antibiotype, pulse-field electrophoresis profile, MLVA type) and epidemiological data (sporadic cases, epidemic cases, etc.). FIG. 10 gives the various variable-sequence (spacer) compositions for all the *Salmonella* strains analyzed.

EXAMPLE 2

Analysis of the Variable-Sequence Composition of the CRISPR Loci of Three *Salmonella* Strains for the Purpose of Determining their Molecular Type and Subtype Three *Salmonella* strains were isolated from one sample. For each strain, the DNA was extracted according to the method described in example 1 and the CRISPR1 locus and/or the CRISPR2 locus was (were) amplified in a separate gene amplification as described in paragraph 1-2-3-1) above. The variable-sequence composition of each locus was determined by sequencing the DNA.

This composition can also be determined by hybridization of the amplified DNA fragments (labeled during the amplification, or after said amplification, with a radioactive or cold label, for example cyanin 3 or 5) with the sets of probes S1-1 to S44-2 using a DNA chip.

In order to determine the serotype and the subtype of each strain isolated, the composition of the CRISPR1 and/or CRISPR2 loci was compared to the reference base (FIGS. 10 and 9).

1) Analysis of the First Strain 02-1442

Figure 6:
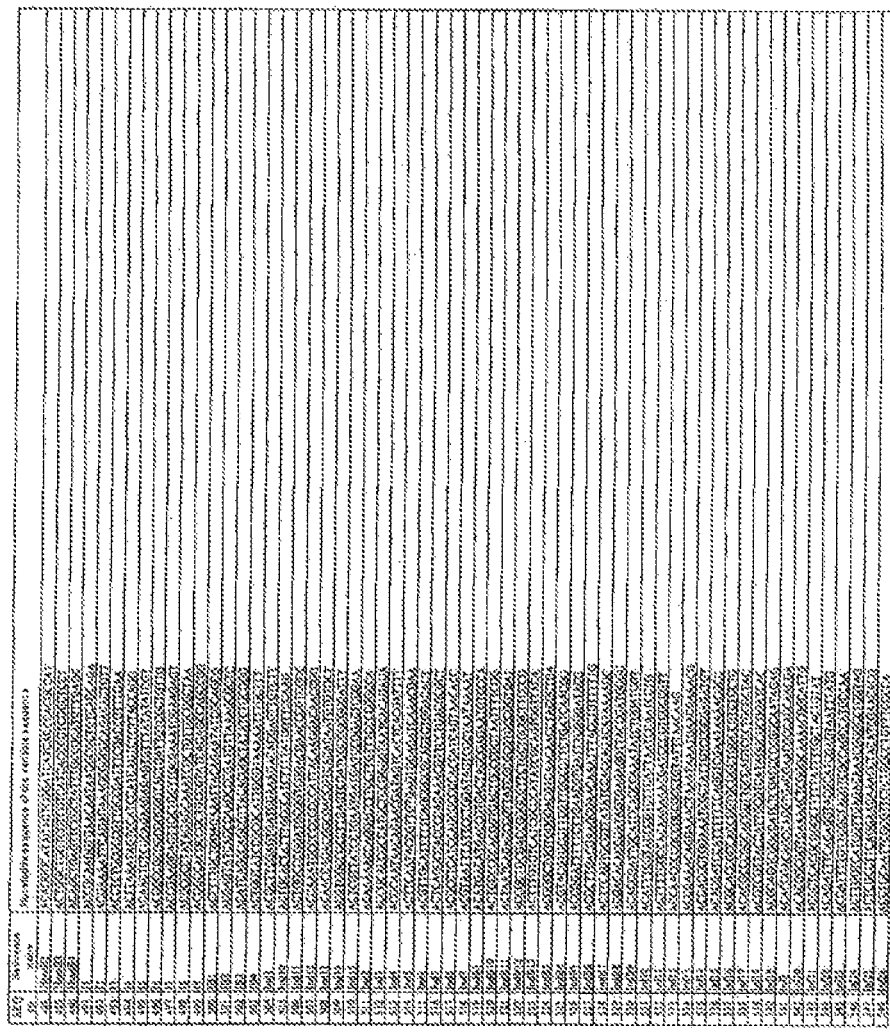
Figure 9:
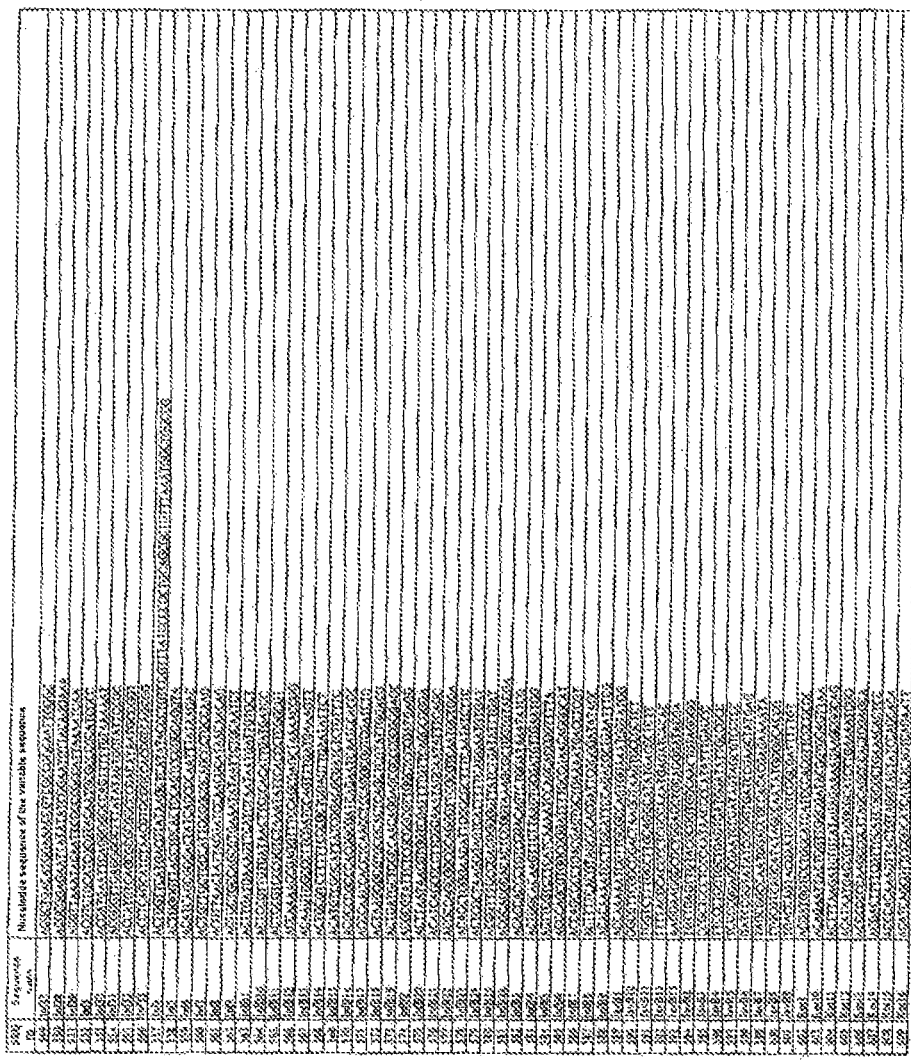
Figure 9:
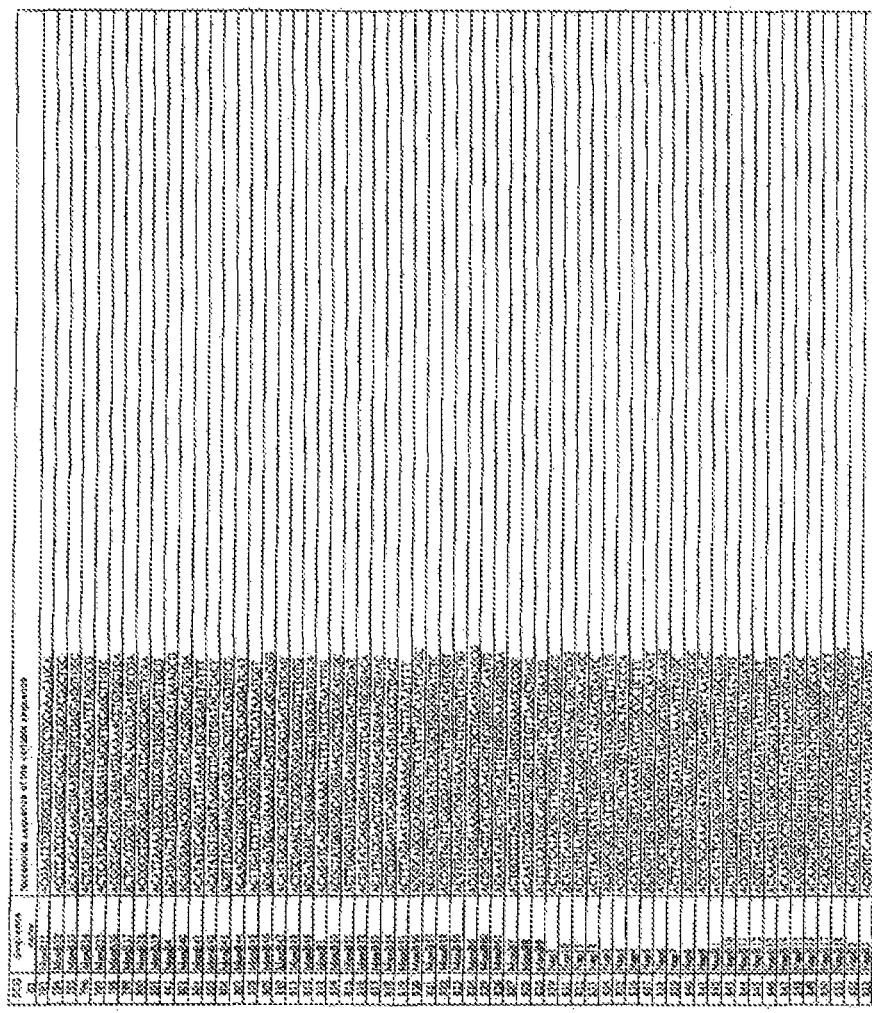
Figure 9:
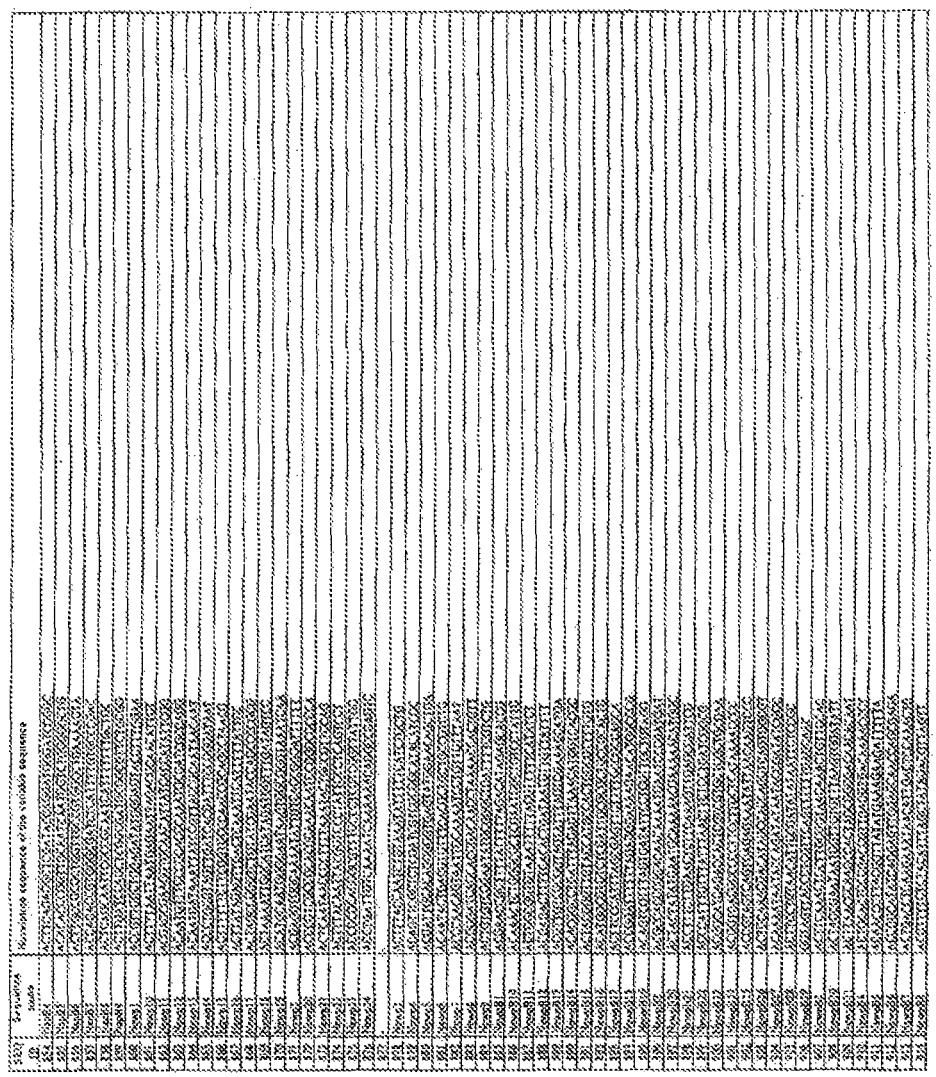
Figure 9:
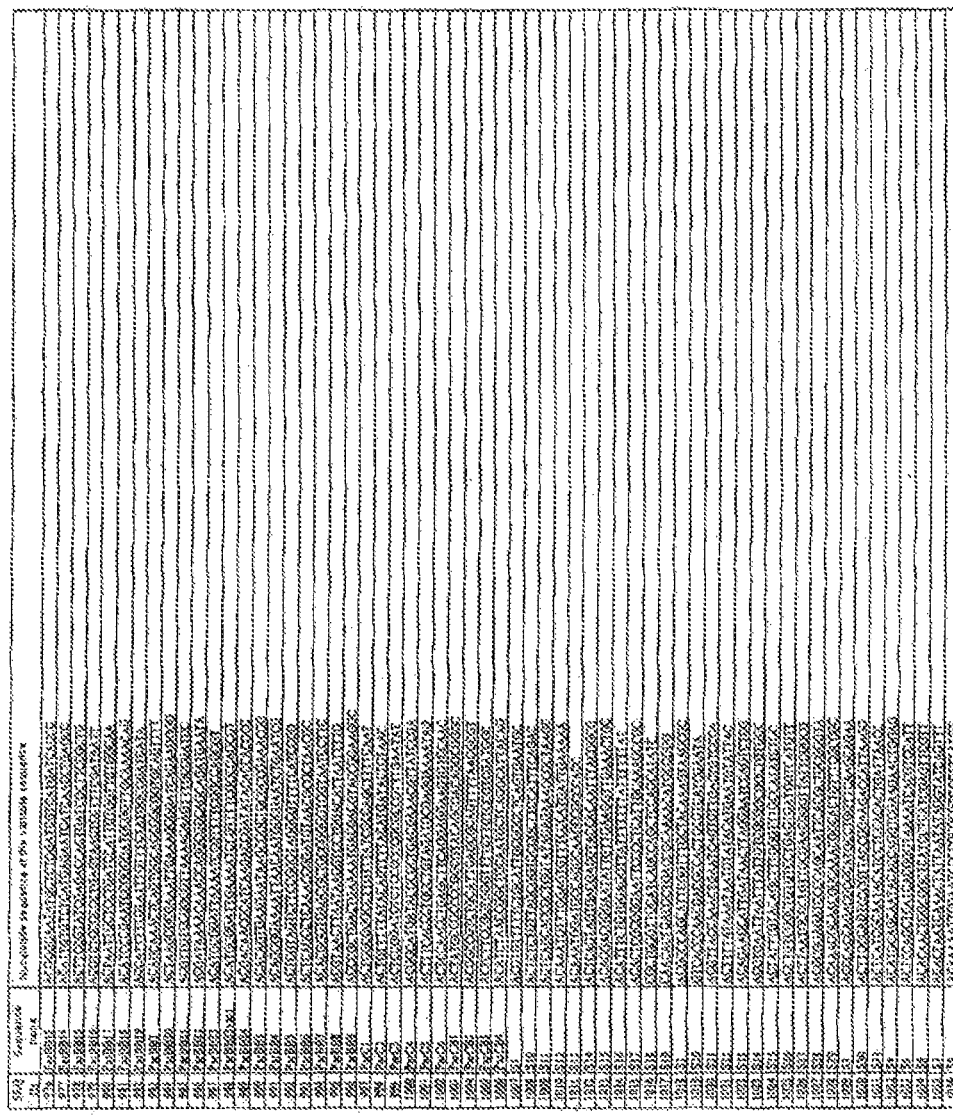
Figure 9:
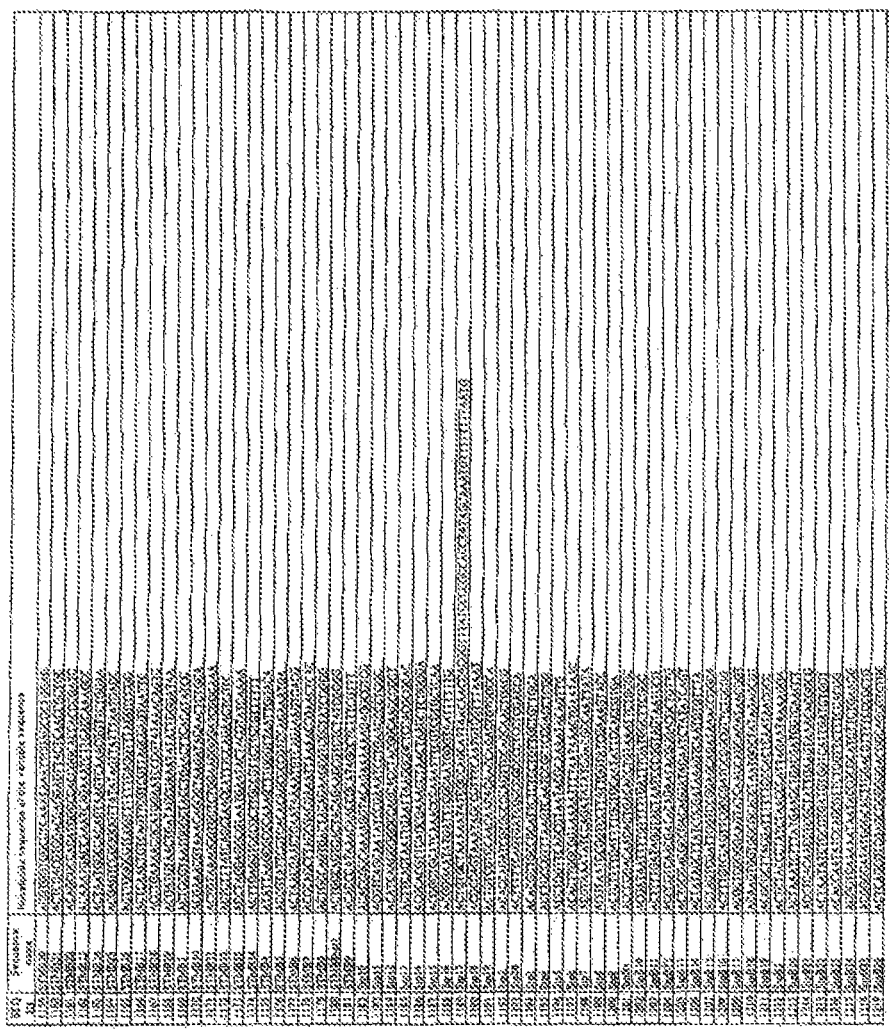
Figure 9:
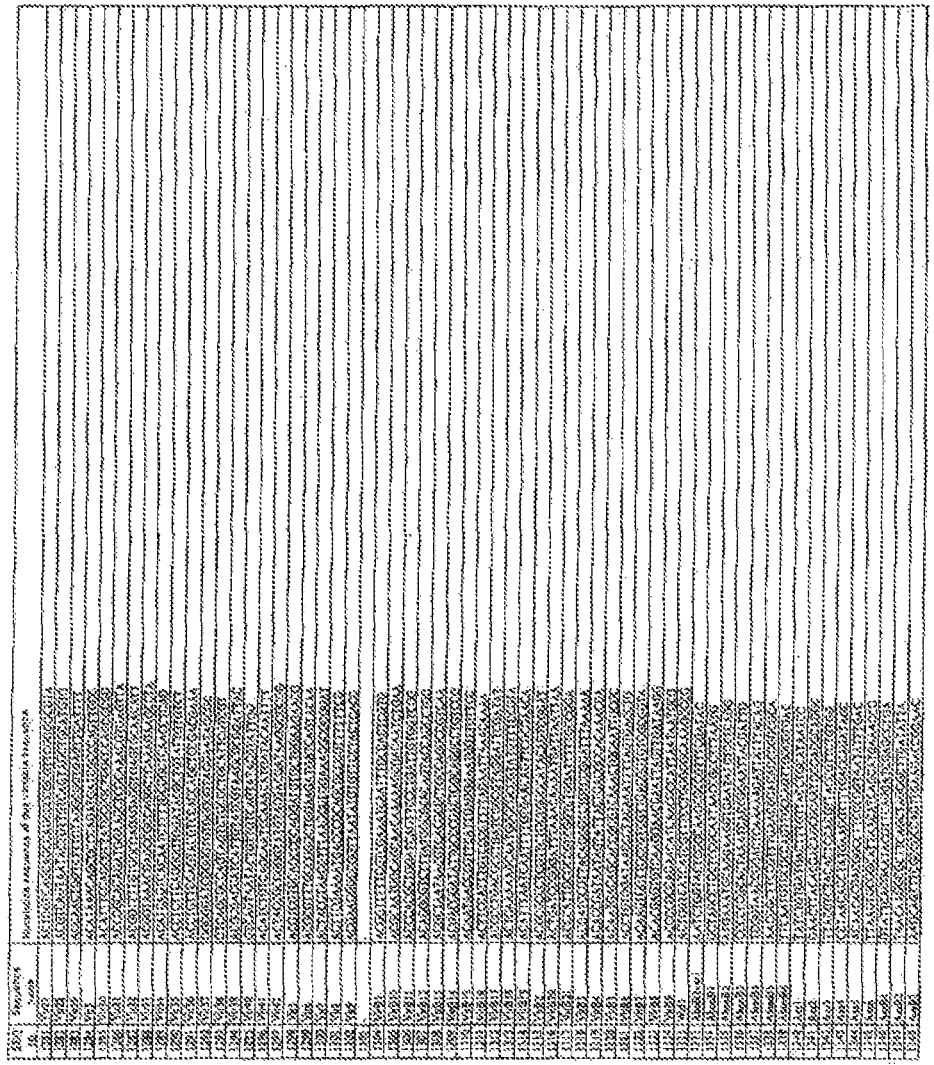
Figure 9:
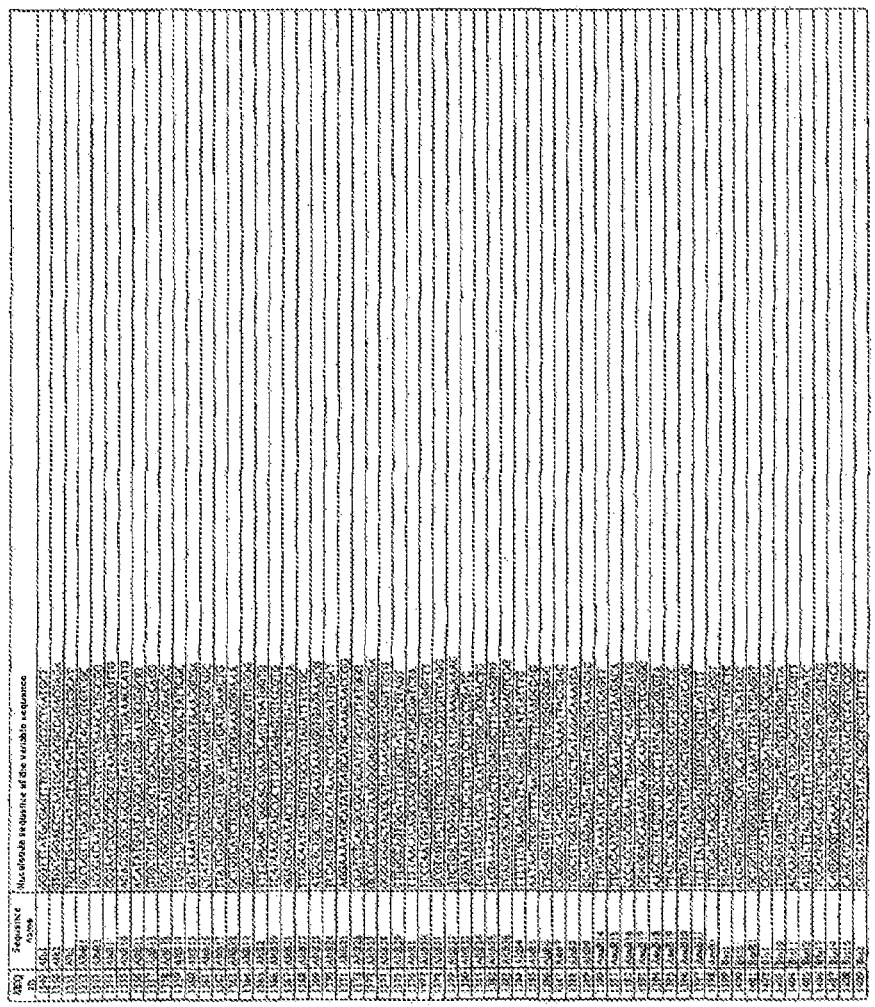
Figure 9:
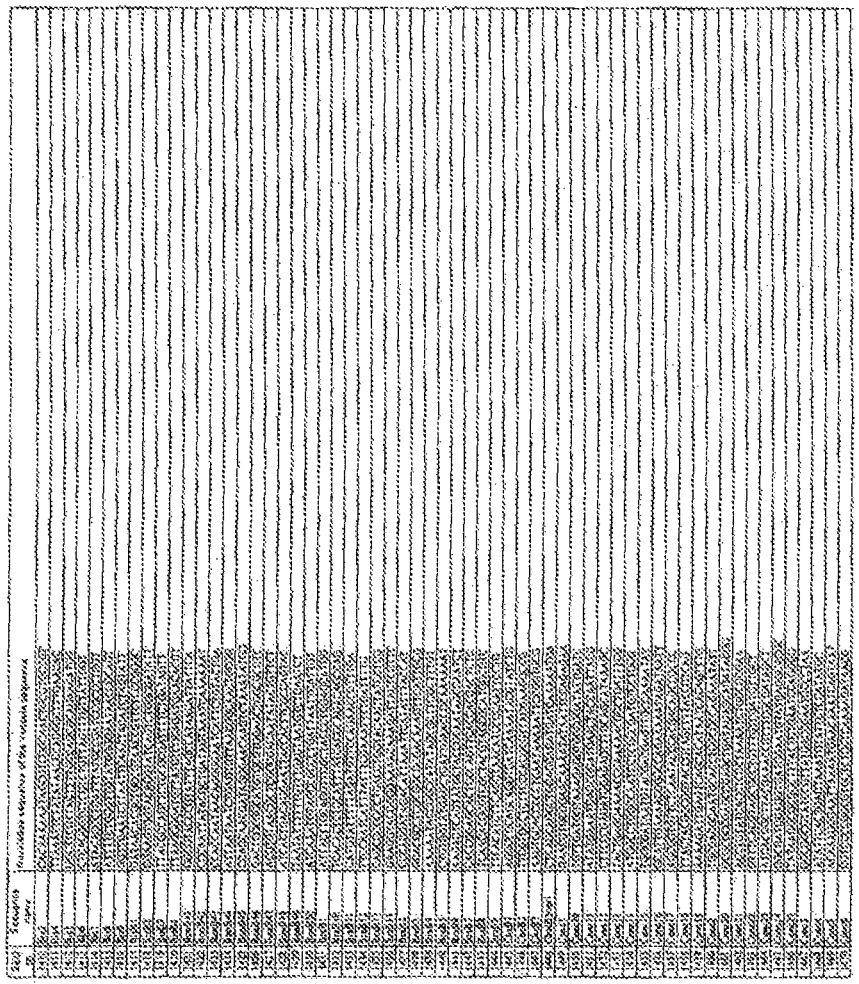
Figure 9:
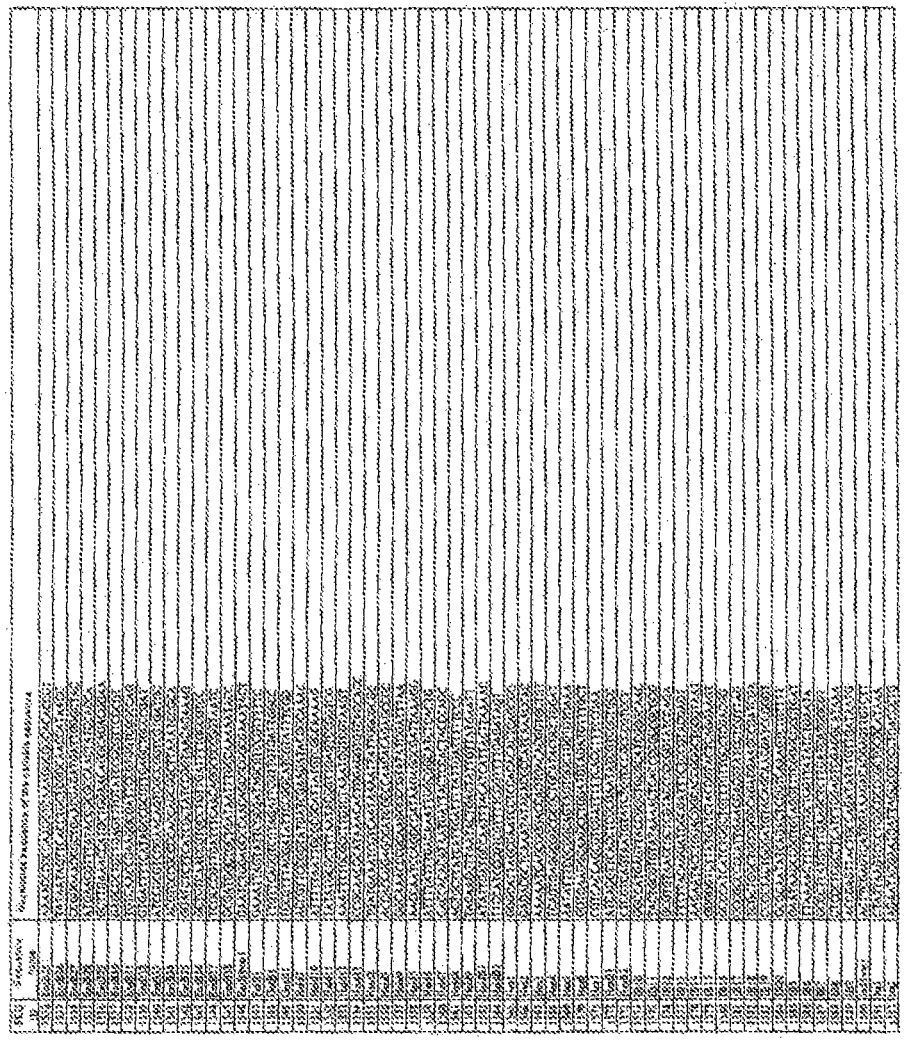
Figure 9:
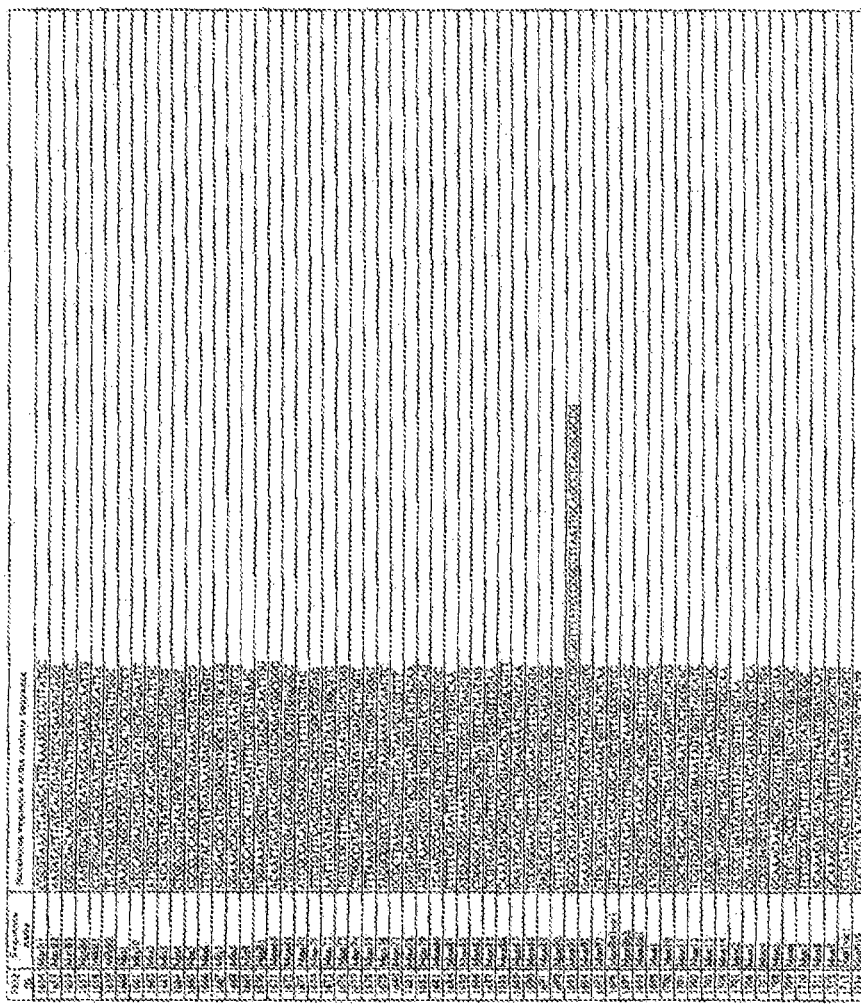
Figure 9:
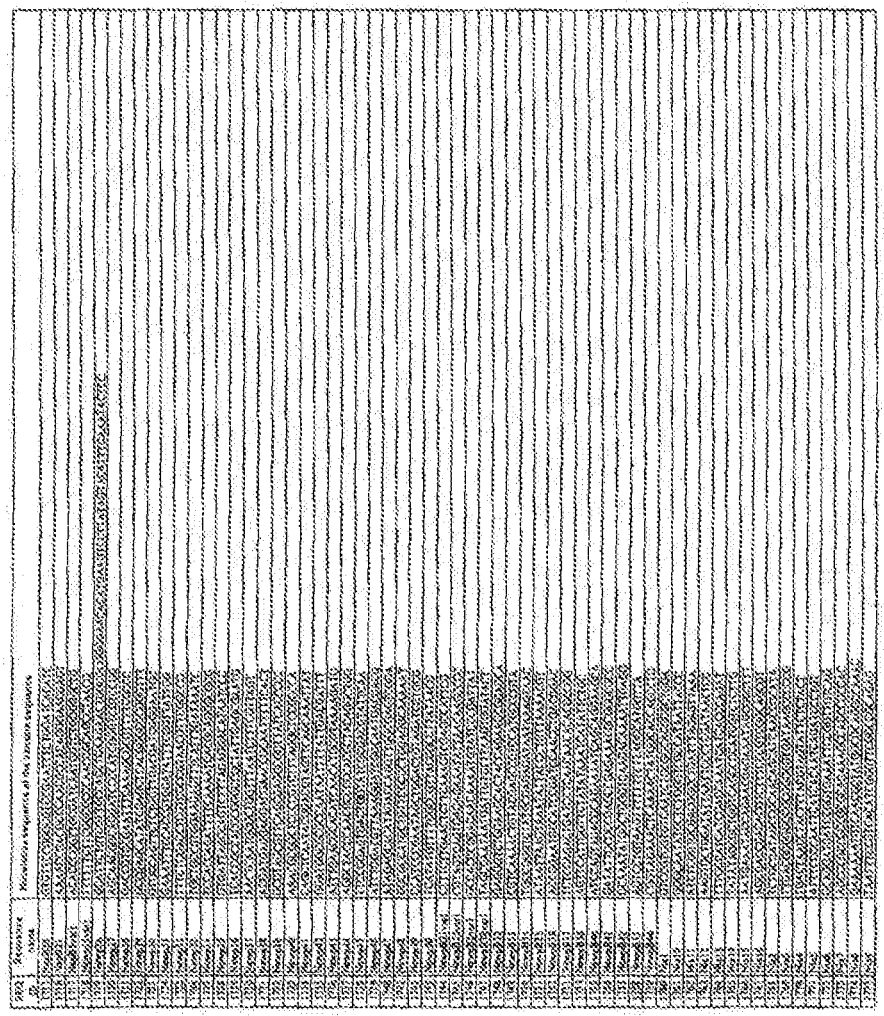
Figure 9:
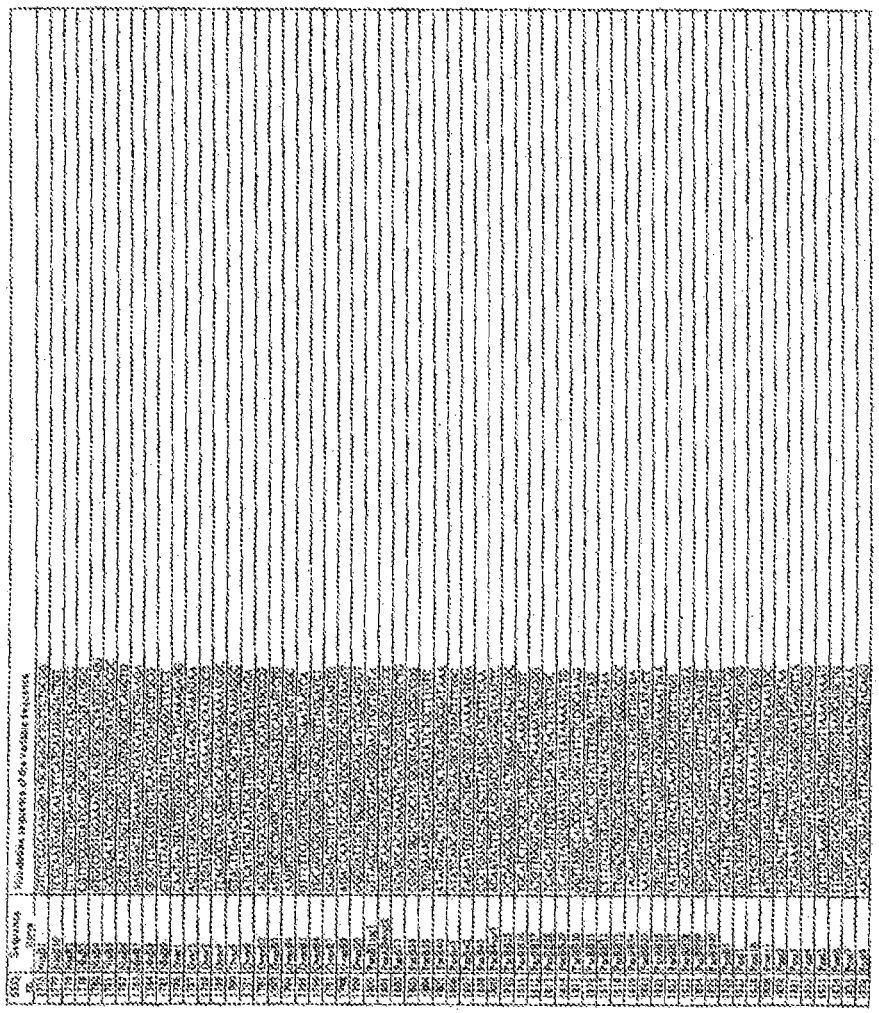

The sequence of the CRISPR1 locus (5' to 3') is represented in FIG. 6A.

The variable-sequence (spacer) composition of this sequence was determined as being the following: Ent1-Ent2-Ent3-Ent4-Ent5-Ent6-Ent7-Ent8, in which:

```
Ent1 (SEQ ID No.: 379):
ACTATTTATAAGCGTGTCATCTATGCAACCCAAC

Ent2 (SEQ ID No.: 380):
ACACCTGCCCGACCCAATAAGGGGGCCCTCGTGA

Ent3 (SEQ ID No.: 383):
ACGGCCGCTGGTCAAATTCCCAATCTGAGCAATC

Ent4 (SEQ ID No.: 384):
ACATAGCCCCGGCAGCGATAGCTAAACCAGTTCC

Ent5 (SEQ ID No.: 385):
ACGCCTCAAAATCTCTCGGTGAGATGTAAGCGTC

Ent6 (SEQ ID No.: 387):
ACACCAGTGGTCAGCGGCGGATGAATTTGCCCTG
```

Ent8 (SEQ ID No.: 389):
ACGAGAATGCTCATGCGCGTGAGCGCCATATATT

Ent8 (SEQ ID No.: 390):
ACAGGCGGACCGAAAAACCGTTTTCAGCCAACGT.

The sequence of the CRISPR2 locus (5' to 3') is represented in FIG. 6B.

The variable-sequence (spacer) composition of this sequence was determined as being the following: EntB0-EntB1-EntB2-EntB3-EntB4-EntB5-EntB6-EntB7-EntB8-EntB9,
in which:

```
EntB0 (SEQ ID No.: 392):
ACGGCTACACGCAAAAATTCCAGTCGTTGGCGCA

EntB1 (SEQ ID No.: 393):
ACCCGATTAAGATCCGCAGTCTGCATCAGTAACT

EntB2 (SEQ ID No.: 404):
ACCGATTCTACGGCAACAGGCCAGGCTGCGACCG

EntB3 (SEQ ID No.: 407):
ACATCAAACATGGAAACCCCTTTAATGAGAGCAA

EntB4 (SEQ ID No.: 408):
ACTCAGGAACGCGCGGCGGAAGAGCTTGGTGTTTG

EntB5 (SEQ ID No.: 409):
ACGCTGCCTTTCCCGGAGTTCCGGCCCCTAAATT

EntB6 (SEQ ID No.: 410):
ACTCATGCGCTATAAAAATCAGACTGTCACATGC

EntB7 (SEQ ID No.: 411):
ACTGATTATTGACGACAACAGCACAGACCGGCAG

EntB8 (SEQ ID No.: 412):
ACAATAATCGGCAATTTGTCCTGGACAGGCACGG

EntB9 (SEQ ID No.: 413):
ACGAATCTGGAGGCCAACAGCGCGGCGAAATCCT
```

After comparison, with the reference base (FIGS. 3 and 9), of the composition of the two CRISPR loci of the isolated bacterium, it was determined that the strain 02-1142 had the same spacer composition as the strains of *Salmonella* enterica serotype Enteritidis. This result was confirmed by serotyping.

2) Analysis of the Second Strain 02-4232

The sequence of the CRISPR1 locus (5' to 3') is represented in FIG. 7A.

The variable-sequence (spacer) composition of this sequence was determined as being the following: Ent1-Ent2var1-Ent3-Ent4-Ent5-Ent6-Ent7-Ent9-Ent8,
in which:

```
Ent1 (SEQ ID No.: 379):
ACTATTTATAAGCGTGTCATCTATGCAACCCAAC

Ent2var1 (SEQ ID No.: 381):
ACACCTGCCCGACCCAATAAGGAGGCCCTCGTGA

Ent3 (SEQ ID No.: 383):
ACGGCCGCTGGTCAAATTCCCAATCTGAGCAATC

Ent4 (SEQ ID No.: 384):
ACATAGCCCCGGCAGCGATAGCTAAACCAGTTCC

Ent5 (SEQ ID No.: 385):
ACGCCTCAAAATCTCTCGGTGAGATGTAAGCGTC

Ent6 (SEQ ID No.: 387):
ACACCAGTGGTCAGCGGCGGATGAATTTGCCCTG

Ent7 (SEQ ID No.: 389):
ACGAGAATGCTCATGCGCGTGAGCGCCATATATT

Ent9 (SEQ ID No.: 391):
ACCATGGCAATTTTACGGCGGACGTGCTCGCTCT

Ent8 (SEQ ID No.: 390):
ACAGGCGGACCGAAAAACCGTTTTCAGCCAACGT.
```

The sequence of the CRISPR2 locus (5' to 3') is represented in FIG. 7B.

The variable-sequence (spacer) composition of this sequence was determined as being the following: EntB0-EntB1-EntB2-EntB3-EntB4-EntB5-EntB6-EntB7-EntB8-EntB8-EntB9,
in which:

```
EntB0 (SEQ ID No.: 392):
ACGGCTACACGCAAAAATTCCAGTCGTTGGCGCA

EntB1 (SEQ ID No.: 393):
ACCCGATTAAGATCCGCAGTCTGCATCAGTAACT

EntB2 (SEQ ID No.: 404):
ACCGATTCTACGGCAACAGGCCAGGCTGCGACCG

EntB3 (SEQ ID No.: 407):
ACATCAAACATGGAAACCCCTTTAATGAGAGCAA

EntB4 (SEQ ID No.: 408):
ACTCAGGAACGCGCGGCGGAAGAGCTTGGTGTTTG

EntB5 (SEQ ID No.: 409):
ACGCTGCCTTTCCCGGAGTTCCGGCCCCTAAATT

EntB6 (SEQ ID No.: 410):
ACTCATGCGCTATAAAAATCAGACTGTCACATGC

EntB7 (SEQ ID No.: 411):
ACTGATTATTGACGACAACAGCACAGACCGGCAG

EntB8 (SEQ ID No.: 412):
ACAATAATCGGCAATTTGTCCTGGACAGGCACGG

EntB9 (SEQ ID No.: 413):
ACGAATCTGGAGGCCAACAGCGCGGCGAAATCCT.
```

After comparison, with the reference base (FIGS. 3 and 9), of the composition of the two CRISPR loci of the isolated bacterium, it was determined that the strain 02-4232 had the same spacer composition as the strains of *Salmonella enterica* serotype Enteritidis. This result was confirmed by serotyping. The spacer composition was different than the previous strain 02-1142, which was in agreement with the subtyping result obtained by phage typing (the strain 02-4232 being of lysotype PT4 and the strain 02-4232 of lysotype PT8).

3) Analysis of the Third Strain 02-1941

Figure 8:
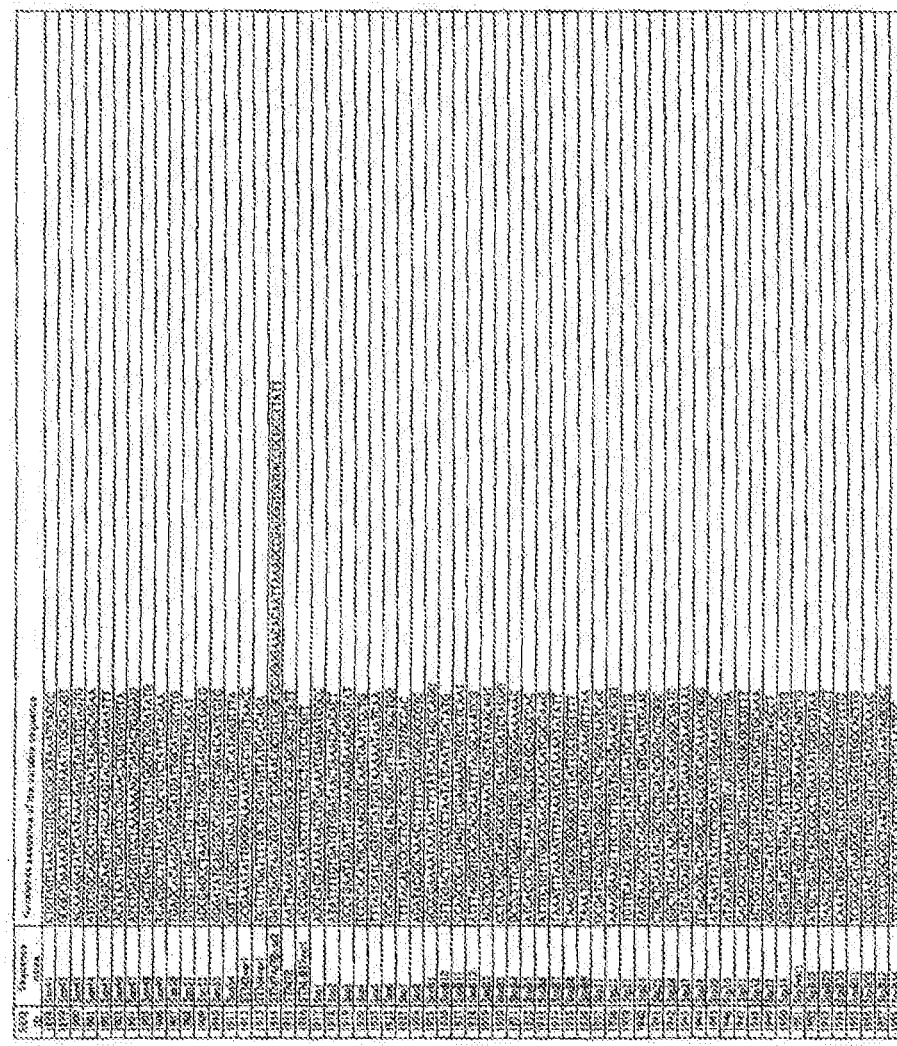
FIG. 8 represents the result of the sequencing (5'-3') of the CRISPR1 (SEQ ID NO: 2157) locus of a Salmonella strain to be identified (legend identical to that of FIG. 6).
Figure 9:
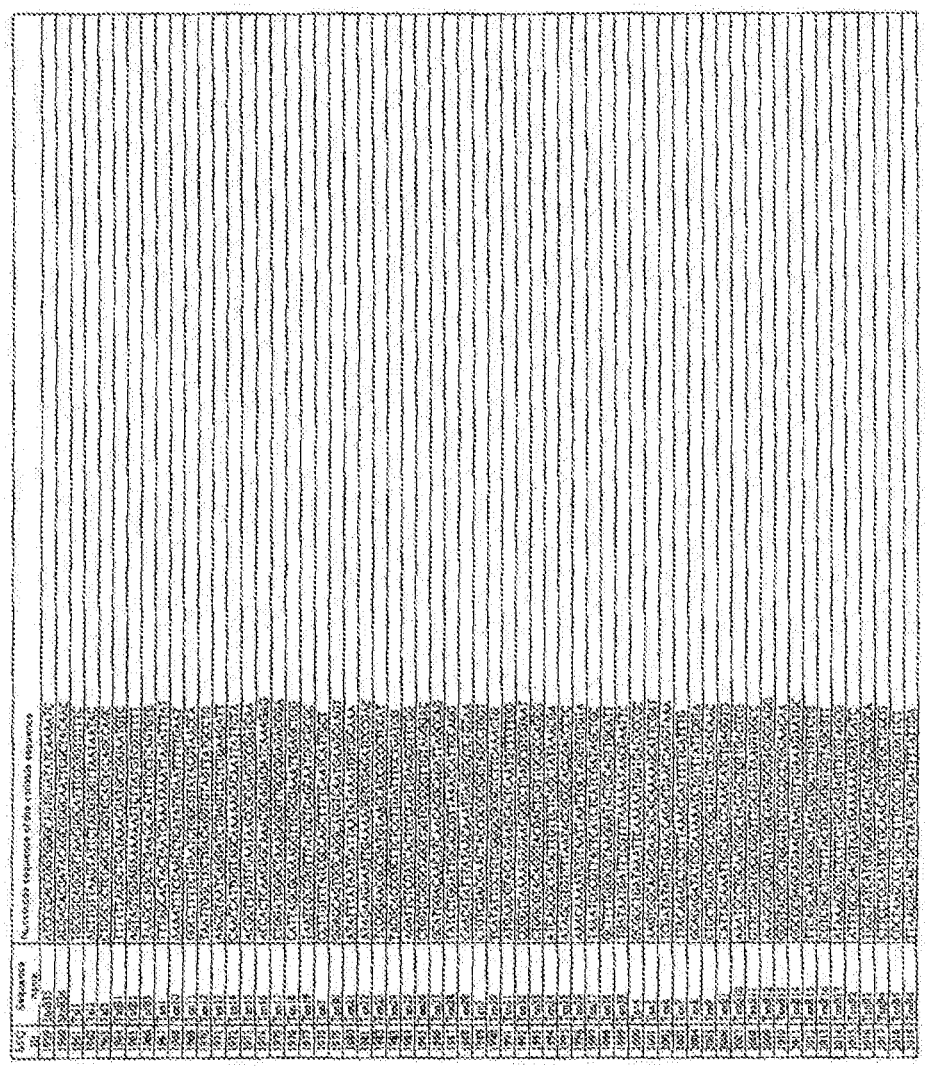
Figure 8:
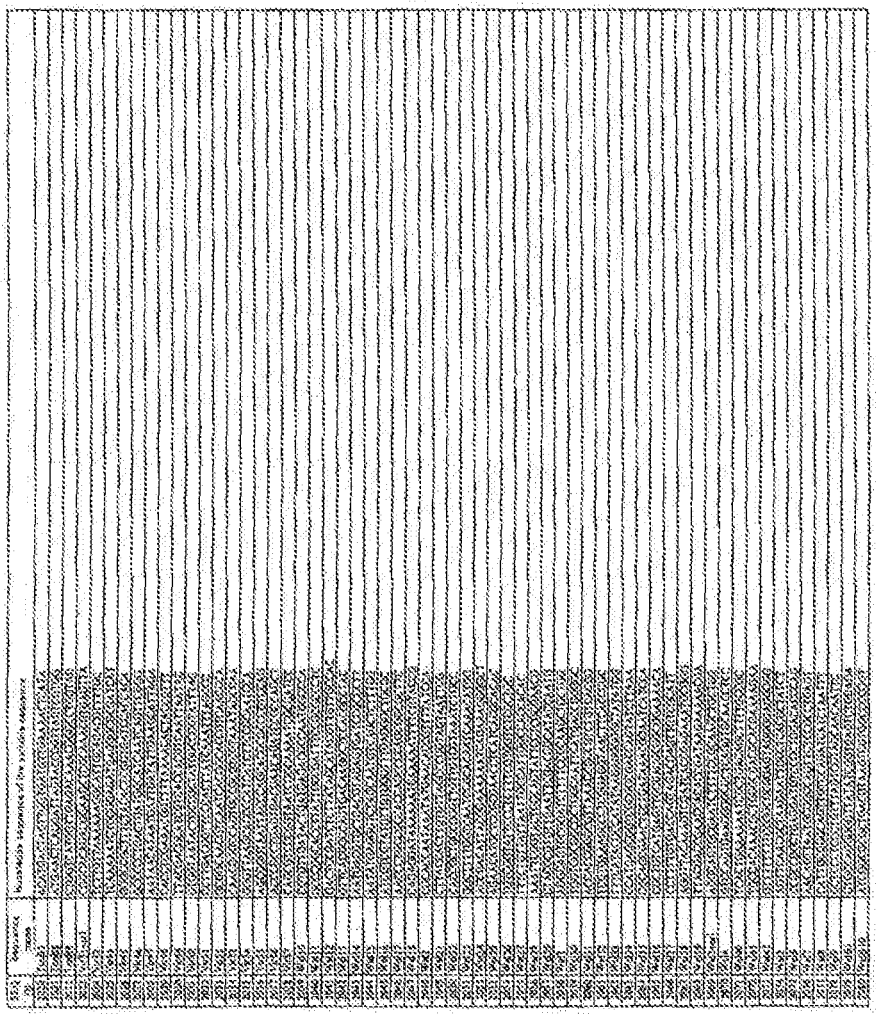
Figure 9:
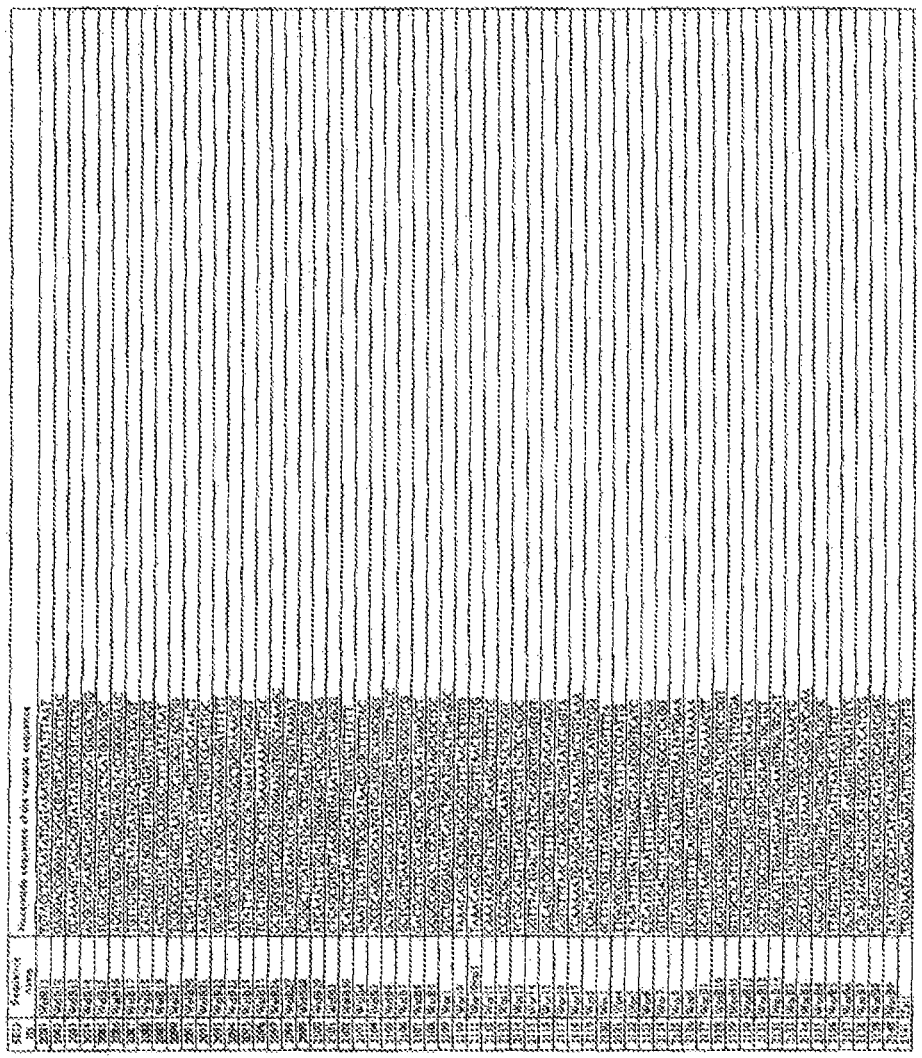
Figure 9:
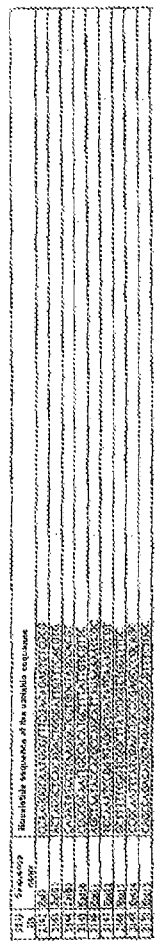
Figure 8E:
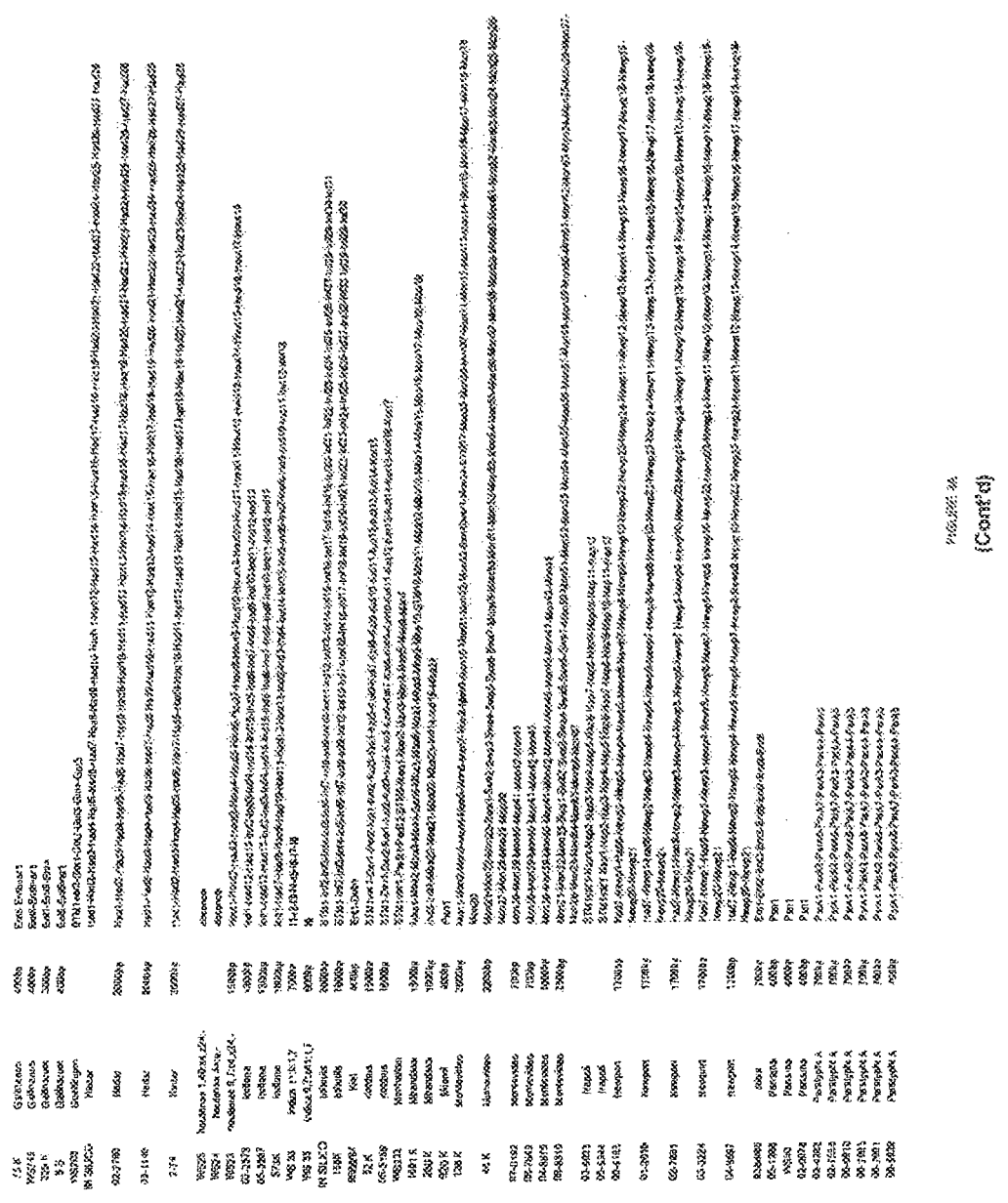
Figure 8A:
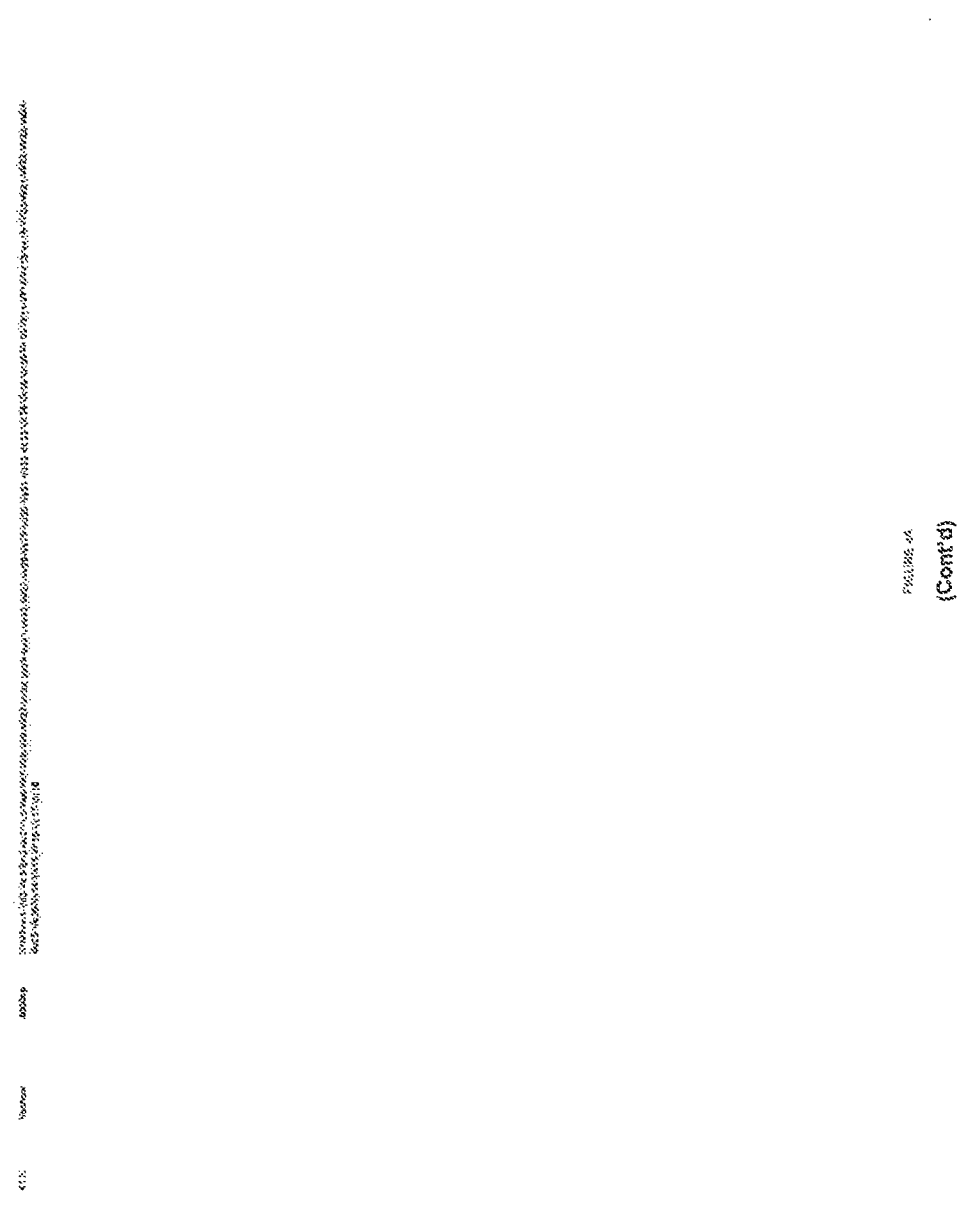

The sequence of the CRISPR1 locus (5' to 3') is represented in FIG. 8A.

The variable-sequence (spacer) composition of this sequence was determined as being the following: STM1-STM2-STM3-STM25-STM26-STM27-STM4-STM5-STM6-STM24,
in which:

```
STM1 (SEQ ID No.: 1106):
ATTTTTCAGCCCTTGTCGACTGCGGAACGCCCCT

STM2 (SEQ ID No.: 1123):
ACGCGAAATAGTGGGGAAAAACCCCTGGTTAACC
```

```
STM3 (SEQ ID No.: 1133):
ACTAGGCCTTGATACCATCGCTCGCACCTCGTCA

STM25 (SEQ ID No.: 1128):
ACGTTTATTACTGCTTAGTTAATTAATGGGTTGC

STM26 (SEQ ID No.: 1129):
ACAGGCGAATAATCTCTAATAGTCTCAATTCGTT

STM27 (SEQ ID No.: 1130):
ACTAAATCTGGCGTCGAGACATTCGAAATAGTGC

STM4 (SEQ ID No.: 1137):
ACTCTTTTGATTTTGCTGCGATGTTATAACCAGA

STM5 (SEQ ID No.: 1138):
ACTATCCACATATACCCGCAATCATATTCAAGAA

STM6 (SEQ ID No.: 1139):
ACAATCACTGCGGGGGTATTTAGCGGAAACGGCT

STM24 (SEQ ID No.: 1127):
ACCAGCACGAAAAATTATTTACTGTCGTTGCTCA.
```

After comparison, with the reference base (FIGS. 2 and 9), of the composition of the CRISPR1 locus of the isolated bacterium, it was determined that the strain 02-1941 had the same spacer composition as the strains of *Salmonella enterica* serotype Typhimurium. This result was confirmed by serotyping. In addition, its spacer composition was found in the database virtually exclusively in the strains of *S. enterica*, serotype Typhimurium.

The analysis of a single CRISPR locus (in this case, the CRISPR1 locus) made it possible to identify the bacterial strain isolated.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08673568B2). An electronic copy of the "Sequence Listing" will also be available from the USPTO upon request and payment of the fee set forth in 37 CFR 1.19(b)(3).

The invention claimed is:

1. An in vitro method for molecular typing and/or subtyping of a bacterium of the *Salmonella* genus, using a sample, said method being characterized in that it comprises at least the following steps:
   (a) amplifying a nucleic acid fragment from a bacterium of the *Salmonella* genus, said fragment comprising the CRISPR1 locus and/or the CRISPR2 locus, using at least one set of primers, which primers have a size of less than or equal to 50 nucleotides, said sets of primers being chosen from the group consisting of:
   a set of primers "A", capable of amplifying a nucleic acid fragment comprising the CRISPR1 locus, comprising at least one forward primer A 1 constituted of an oligonucleotide sequence which exhibits at least 70% identity with, or which is identical to, a fragment of the genomic sequence of a bacterium of the *Salmonella* genus located in a region of 1000 by in a position 5' of the CRISPR1 locus, said fragment of the genomic sequence located in a position 5' of the CRISPR1 locus being of the same size as said primer A1, and at least one reverse primer A2 constituted of an oligonucleotide sequence which exhibits at least 70% identity with, or which is identical to a fragment of the genomic sequence complementary to the genomic sequence of a bacterium of the *Salmonella* genus located in a position 3' of the CRISPR1 locus and in a position 5' of the CRISPR2 locus, said complementary genomic sequence fragment being of the same size as said primer A2;
   a set of primers "B", capable of amplifying a nucleic acid fragment comprising the CRISPR2 locus, comprising at least one forward primer B1 constituted of an oligonucleotide sequence which exhibits at least 70% identity with, or which is identical to, a fragment of the genomic sequence of a bacterium of the *Salmonella* genus located in a position 3' of the CRISPR1 locus and in a position 5' of the CRISPR2 locus, said fragment of the genomic sequence located in a position 3' of the CRISPR1 locus and in a position 5' of the CRISPR2 locus being of the same size as said primer B1, and at least one reverse primer B2 constituted of an oligonucleotide sequence which exhibits at least 70% identity with, or which is identical to, a fragment of the genomic sequence complementary to the genomic sequence of a bacterium of the *Salmonella* genus located in the region of 1000 by in a position 3' of the CRISPR2 locus, said complementary genomic sequence fragment being of the same size as said primer B2;
   a set of primers "C", capable of amplifying a nucleic acid fragment comprising the CRISPR1 locus and the CRISPR2 locus, comprising at least one forward primer A1 as defined above and at least one reverse primer B2 as defined above;
   (b) determining the number and the nucleotide sequence of the variable sequences of the CRISPR1 locus and/or of the CRISPR2 locus which is (are) amplified in step (a); and
   (c) comparing said variable-sequence composition of the CRISPR1 and/or CRISPR2 loci with a reference base which provides the variable-sequence composition of the CRISPR1 and CRISPR2 loci of types and subtypes of bacteria of the *Salmonella* genus, listed in FIGS. 10 and 9, or a part of this base, 2. The method as claimed in claim 1, characterized in that the identity of the variable-sequence composition determined in step (b) with respect to a composition appearing in the reference base defined in claim 1, or a part of this base, is indicative of the type and/or of the subtype of the bacterium of the *Salmonella* genus present in the sample.

3. The method as claimed in claim 1 or claim 2, characterized in that said primers have a size of between 15 and 30 nucleotides.

4. The method as claimed in any one of claim 1, characterized in that said nucleic acid fragment comprising the CRISPR1 locus and/or the CRISPR2 locus has a size of between 400 and 20 000 bp.

5. The method as claimed in claim 1, characterized in that said fragment of the genomic sequence of a bacterium of the *Salmonella* genus located in a position 5' of the CRISPR1 locus, and/or said fragment of the genomic sequence complementary to the genomic sequence of a bacterium of the *Salmonella* genus located in a position 3' of the CRISPR2 locus, is (are) at a distance from the CRISPR1 or CRISPR2 locus of less than 500 bp, preferably less than 100 bp.

6. The method as claimed in claim 1, characterized in that said genomic sequence of a bacterium of the *Salmonella* genus is chosen from the genomic sequence of *S. enterica* serotype Typhimurium LT2 (genomic sequence available under numbers GI: 16421485 and GI: 16421501 in the GenBank database) or of *S. enterica* serotype Typhi CT18 (genomic sequence available under number GI 16503 805 in the GenBank database).

7. The method as claimed in claim 5, characterized in that the set of primers is selected from the group constituted of:
the set of primers, capable of amplifying the CRISPR1 locus, constituted of the primer of sequence SEQ ID No.: 1326, combined with at least one of the primers of sequence SEQ ID Nos: 1327, 1328, 1329, 2151 and 2152,
the set of primers, capable of amplifying the CRISPR2 locus, constituted of the primer of sequence SEQ ID No.: 1330, combined with at least one of the primers of sequence SEQ ID Nos: 1331 and 1332, and
the set of primers, capable of simultaneously amplifying the two loci CRISPR1 and CRISPR2, constituted of the primer of sequence SEQ ID No.: 1326, combined with at least one of the two primers of sequence 1331 and 1332.

8. The method as claimed in claim 1, characterized in that amplification step (a) is carried out by a method selected from the group constituted of: polymerase chain reaction (PCR), ligase chain reaction (LCR), nucleic acid sequence-based amplification (NASBA), cycling probe technology (CPT), nested PCR and multiplex PCR.

9. The method as claimed in claim 1, characterized in that step (b) is carried out using a DNA sequencing method.

10. The method as claimed in claim 1, characterized in that step (b) is carried out by:
(i) hybridization with one, several or all the set(s) of probes chosen from:
set S1-1, comprising or constituted of at least one probe comprising at least or constituted of at least 8 consecutive nucleotides of any one of the nucleic acid sequences SEQ ID Nos.: 1106 to 1119, 1123 to 1140, 1142, 1143, 1914 and/or the nucleic acid sequences complementary thereto (nucleotide sequences corresponding to the various variable sequences of the CRISPR1 locus of the serotype Typhimurium);
set S1-2, comprising or constituted of at least one probe comprising at least or constituted of at least 8 consecutive nucleotides of any one of the nucleic acid sequences SEQ ID Nos.: 455, 1144 to 1153, 1155 to 1181 and/or the nucleic acid sequences complementary thereto (nucleotide sequences corresponding to the various variable sequences of the CRISPR2 locus of the serotype Typhimurium);
set S2-1, comprising or constituted of at least one probe comprising at least one probe comprising at least 8 consecutive nucleotides of any one of the nucleic acid sequences SEQ ID Nos.: 256, 378 to 381, 383 to 387, 389 to 391, 1106, 1514, 1528, 2148 to 2153 and/or the nucleic acid sequences complementary thereto (nucleotide sequences corresponding to the various variable sequences of the CRISPR1 locus of the serotype Enteritidis);
set S2-2, comprising or constituted of at least one probe comprising at least or constituted of at least 8 consecutive nucleotides of any one of the nucleic acid sequences SEQ ID Nos.: 392 to 413, 519, 815, 972, 983, 989, 1529 to 1546, 1952 and/or the nucleic acid sequences complementary thereto (nucleotide sequences corresponding to the various variable sequences of the CRISPR2 locus of the serotype Enteritidis);
set S3-1, comprising or constituted of at least one probe comprising at least or constituted of at least 8 consecutive nucleotides of any one of the nucleic acid sequences SEQ ID Nos.: 421 to 442, 444, 445, 447 to 450 and/or the nucleic acid sequences complementary thereto (nucleotide sequences corresponding to the various variable sequences of the CRISPR1 locus of the serotype Hadar);
set S3-2, comprising or constituted of at least one probe comprising at least or constituted of at least 8 consecutive nucleotides of any one of the nucleic acid sequences SEQ ID Nos.: 451 to 465, 1144 to 1147, 1150 to 1152, 1154, 1155, 1158, 1169, 1172, 1175 to 1177, 1179, 1181 and/or the nucleic acid sequences complementary thereto (nucleotide sequences corresponding to the various variable sequences of the CRISPR2 locus of the serotype Hadar);
set S4-1, comprising or constituted of at least one probe comprising at least or constituted of at least 8 consecutive nucleotides of any one of the nucleic acid sequences SEQ ID Nos.: 65, 382, 1120, 1263 to 1302, 2024 to 2038 and/or the nucleic acid sequences complementary thereto (nucleotide sequences corresponding to the various variable sequences of the CRISPR1 locus of the serotype Virchow);
set S4-2, comprising or constituted of at least one probe comprising at least or constituted of at least 8 consecutive nucleotides of any one of 5 the nucleic acid sequences SEQ ID Nos.: 83, 93, 94, 1304 to 1324 and/or the nucleic acid sequences complementary thereto (nucleotide sequences corresponding to the various variable sequences of the CRISPR2 locus of the serotype Virchow);
set S5-1, comprising or constituted of at least one probe comprising at least or constituted of at least 8 consecutive nucleotides of any one of the nucleic acid sequences SEQ ID Nos.: 531 to 562, 1106 and/or the nucleic acid sequences complementary thereto (nucleotide sequences corresponding to the various variable sequences of the CRISPR1 locus of the serotype Infantis);
set S5-2, comprising or constituted of at least one probe comprising at least or constituted of at least 8 consecutive nucleotides of any one of the nucleic acid sequences SEQ ID Nos.: 563 to 588 and/or the nucleic acid sequences complementary thereto (nucleotide sequences corresponding to the various variable sequences of the CRISPR2 locus of the serotype Infantis);
set S6-1, comprising or constituted of at least one probe comprising at least or constituted of at least 8 consecutive nucleotides of any one of the nucleic acid sequences SEQ ID Nos.: 1254 to 1259 and/or the nucleic acid sequences complementary thereto (nucleotide sequences corresponding to the various variable sequences of the CRISPR1 locus of the serotype Typhi);

set S6-2, comprising or constituted of at least one probe comprising at least or constituted of at least 8 consecutive nucleotides of the nucleic acid sequence SEQ ID No.: 1260 and/or the nucleic acid sequence complementary thereto (nucleotide sequences corresponding to the variable sequence of the CRISPR2 locus of the serotype Typhi);

set S7-1, comprising or constituted of at least one probe comprising at least or constituted of at least 8 consecutive nucleotides of any one of the nucleic acid sequences SEQ ID Nos: 448, 449, 860 to 884, 1719 to 1724, 1727 to 1743, 1745 and/or the nucleic acid sequences complementary thereto (nucleotide sequences corresponding to the various variable sequences of the CRISPR1 locus of the serotype Newport);

set S7-2, comprising or constituted of at least one probe comprising at least or constituted of at least 8 consecutive nucleotides of any one of the nucleic acid sequences SEQ ID Nos: 453 to 456, 563, 621 622, 625, 626, 657, 885 to 896, 906 to 915, 933, 1144, 1145, 1155, 1156, 1172, 1174, 1748 to 1756, 1758, 1759, 1916 and/or the nucleic acid sequences complementary thereto (nucleotide sequences corresponding to the various variable sequences of the CRISPR2 locus of the serotype Newport);

set S8-1, comprising or constituted of at least one probe comprising at least or constituted of at least 8 consecutive nucleotides of any one of the nucleic acid sequences SEQ ID Nos: 295 to 299, 301 to 323, 738, 1106 to 1109, 1120, 1123, 1128 to 1131, 1133, 1137 to 1140, 1550, 1159 to 1561 and/or the nucleic acid sequences complementary thereto (nucleotide sequences corresponding to the various variable sequences of the CRISPR 1 locus of the serotype Derby);

set S8-2, comprising or constituted of at least one probe comprising at least or constituted of at least 8 consecutive nucleotides of any one of the nucleic acid sequences SEQ ID Nos: 324 to 337, 455, 1144, 1145, 1149 to 1153, 1155 to 1160, 1163, 1172 to 1174 and/or the nucleic acid sequences complementary thereto (nucleotide sequences corresponding to the various variable sequences of the CRISPR2 locus of the serotype Derby);

set S9-1, comprising or constituted of at least one probe comprising at least or constituted of at least 8 consecutive nucleotides of any one of the nucleic acid sequences SEQ ID Nos: 295, 307, 602 to 614, 616 to 619, 1106 1120 and/or the nucleic acid sequences complementary thereto (nucleotide sequences corresponding to the various variable sequences of the CRISPR1 locus of the serotype Kottbus);

set S9-2, comprising or constituted of at least one probe comprising at least or constituted of at least 8 consecutive nucleotides of any one of the nucleic acid sequences SEQ ID Nos: 563, 620 to 629, 885, 896, 907, 913, 914, 933 and/or the nucleic acid sequences complementary thereto (nucleotide sequences corresponding to the various variable sequences of the CRISPR2 locus of the serotype Kottbus);

set S10-1, comprising or constituted of at least one probe comprising at least or constituted of at least 8 consecutive nucleotides of any one of the nucleic acid sequences SEQ ID Nos: 422 to 425, 448 to 450, 504 to 518 and/or the nucleic acid sequences complementary thereto (nucleotide sequences corresponding to the various variable sequences of the CRISPR1 locus of the serotype Indiana);

set S10-2, comprising or constituted of at least one probe comprising at least or constituted of at least 8 consecutive nucleotides of any one of the nucleic acid sequences SEQ ID Nos: 246, 258, 269, 392, 415, 519 to 530 and/or the nucleic acid sequences complementary thereto (nucleotide sequences corresponding to the various variable sequences of the CRISPR2 locus of the serotype Indiana);

set S11-1, comprising or constituted of at least one probe comprising at least or constituted of at least 8 consecutive nucleotides of any one of the nucleic acid sequences SEQ ID Nos: 11 to 23, 238, 948, 1120, 1123, 1133 and/or the nucleic acid sequences complementary thereto (nucleotide sequences corresponding to the various variable sequences of the CRISPR1 locus of the serotype Agana);

set S11-2, comprising or constituted of at least one probe comprising at least or constituted of at least 8 consecutive nucleotides of any one of the nucleic acid sequences SEQ ID Nos: 24 to 31 and/or the nucleic acid sequences complementary thereto (nucleotide sequences corresponding to the various variable sequences of the CRISPR2 locus of the serotype Agana);

set S12-1, comprising or constituted of at least one probe comprising at least or constituted of at least 8 consecutive nucleotides of any one of the nucleic acid sequences SEQ ID Nos: 830 to 841, 1120 and/or the nucleic acid sequences complementary thereto (nucleotide sequences corresponding to the various variable sequences of the CRISPR1 locus of the serotype Napoli);

set S12-2, comprising or constituted of at least one probe comprising at least or constituted of at least 8 consecutive nucleotides of any one of the nucleic acid sequences SEQ ID Nos: 842 to 859 and/or the nucleic acid sequences complementary thereto (nucleotide sequences corresponding to the various variable sequences of the CRISPR2 locus of the serotype Napoli);

set S13-1, comprising or constituted of at least one probe comprising at least or constituted of at least 8 consecutive nucleotides of any one of the nucleic acid sequences SEQ ID Nos: 926 to 932 and/or the nucleic acid sequences complementary thereto (nucleotide sequences corresponding to the various variable sequences of the CRISPR1 locus of the serotype Paratyphi A);

set S13-2, comprising or constituted of at least one probe comprising at least or constituted of at least 8 consecutive nucleotides of any one of the nucleic acid sequences SEQ ID Nos: 933, 935, 936 and/or the nucleic acid sequences complementary thereto (nucleotide sequences corresponding to the various variable sequences of the CRISPR2 locus of the serotype Paratyphi A);

set S14-1, comprising or constituted of at least one probe comprising at least or constituted of at least 8 consecutive nucleotides of any one of the nucleic acid sequences SEQ ID Nos: 707, 937 to 971, 1106, 1128 to 1130, 1133, 1138, 1140, 1802 to 1808, 1915 and/or the nucleic acid sequences complementary thereto (nucleotide sequences corresponding to the various variable sequences of the CRISPR1 locus of the serotypes Paratyphi B and Paratyphi B Java);

set S 14-2, comprising or constituted of at least one probe comprising at least or constituted of at least 8 consecutive nucleotides of any one of the nucleic acid sequences SEQ ID Nos: 861, 972 to 987, 989 to 992 to 996, 1172, 1262, 1462, 1497, 1810 to 1825 and/or the nucleic acid sequences complementary thereto (nucleotide sequences corresponding to the various variable sequences of the CRISPR2 locus of the serotypes Paratyphi B and Paratyphi B Java);

set S15-1, comprising or constituted of at least one probe comprising at least or constituted of at least 8 consecutive nucleotides of any one of the nucleic acid sequences SEQ ID Nos: 232, 238, 239, 997 to 1002, 1106 and/or the nucleic acid sequences complementary thereto (nucleotide sequences corresponding to the various variable sequences of the CRISPR1 locus of the serotype Paratyphi C);

set S15-2, comprising or constituted of at least one probe comprising at least or constituted of at least 8 consecutive nucleotides of any one of the nucleic acid sequences SEQ ID Nos: 280, 290, 291, 392, 393, 415, 1003 to 1006, 1262 and/or the nucleic acid sequences complementary thereto (nucleotide sequences corresponding to the various variable sequences of the CRISPR2 locus of the serotype Paratyphi C);

set S16-1, comprising or constituted of at least one probe comprising at least or constituted of at least 8 consecutive nucleotides of any one of the nucleic acid sequences SEQ ID Nos: 211 to 224, 421, 427, 428, 432, 443 to 445, 447 to 449, 504 and/or the nucleic acid sequences complementary thereto (nucleotide sequences corresponding to the various variable sequences of the CRISPR1 locus of the serotype Bovismorbificans);

set S16-2, comprising or constituted of at least one probe comprising at least or constituted of at least 8 consecutive nucleotides of any one of the nucleic acid sequences SEQ ID Nos: 196 to 209, 994, 1144, 1145, 1172 and/or the nucleic acid sequences complementary thereto (nucleotide sequences corresponding to the various variable sequences of the CRISPR2 locus of the serotype Bovismorbificans);

set S17-1, comprising or constituted of at least one probe comprising at least or constituted of at least 8 consecutive nucleotides of the nucleic acid sequence SEQ ID No.: 916 and/or the nucleic acid sequence complementary thereto (nucleotide sequences corresponding to the variable sequence of the CRISPR1 locus of the serotype Panama);

set S17-2, comprising or constituted of at least one probe comprising at least or constituted of at least 8 consecutive nucleotides of any one of the nucleic acid sequences SEQ ID Nos: 918 to 925, 934 and/or the nucleic acid sequences complementary thereto (nucleotide sequences corresponding to the various variable sequences of the CRISPR2 locus of the serotype Panama);

set S18-1, comprising or constituted of at least one probe comprising at least or constituted of at least 8 consecutive nucleotides of any one of the nucleic acid sequences SEQ ID Nos: 11, 16, 67, 74, 442, 444, 446 to 448, 602, 937, 948, 1120, 1128 to 1130, 1182 to 1200, 1937 to 1950 and/or the nucleic acid sequences complementary thereto (nucleotide sequences corresponding to the various variable sequences of the CRISPR1 locus of the serotype Saintpaul);

set S18-2, comprising or constituted of at least one probe comprising at least or constituted of at least 8 consecutive nucleotides of any one of the nucleic acid sequences SEQ ID Nos: 972, 983, 989, 1201 to 1214, 1216 to 1227, 1952 to 1960 and/or the nucleic acid sequences complementary thereto (nucleotide sequences corresponding to the various variable sequences of the CRISPR2 locus of the serotype Saintpaul);

set S19-1, comprising or constituted of at least one probe comprising at least or constituted of at least 8 consecutive nucleotides of any one of the nucleic acid sequences SEQ ID Nos: 514, 1062 to 1089, 1100, 1284, 1886 to 1911 and/or the nucleic acid sequences complementary thereto (nucleotide sequences corresponding to the various variable sequences of the CRISPR1 locus of the serotype Senftenberg);

set S19-2, comprising or constituted of at least one probe comprising at least or constituted of at least 8 consecutive nucleotides of any one of the nucleic acid sequences SEQ ID Nos: 300, 1090 to 1097, 1101 to 1103, 1304, 1315, 1318 to 1320 and/or the nucleic acid sequences complementary thereto (nucleotide sequences corresponding to the various variable sequences of the CRISPR2 locus of the serotype Senftenberg);

set S20-1, comprising or constituted of at least one probe comprising at least or constituted of at least 8 consecutive nucleotides of any one of the nucleic acid sequences SEQ ID Nos: 67, 74 to 80 and/or the nucleic acid sequences complementary thereto (nucleotide sequences corresponding to the various variable sequences of the CRISPR1 locus of the serotype Anatum);

set S20-2, comprising or constituted of at least one probe comprising at least or constituted of at least 8 consecutive nucleotides of any one of the nucleic acid sequences SEQ ID Nos: 83 to 94, 1304, 1315, 1318 to 1322, 1324, 1390 to 1397 and/or the nucleic acid sequences complementary thereto (nucleotide sequences corresponding to the various variable sequences of the CRISPR2 locus of the serotype Anatum);

set S21-1, comprising or constituted of at least one probe comprising at least or constituted of at least 8 consecutive nucleotides of any one of the nucleic acid sequences SEQ ID Nos: 379, 383 to 385, 388 and/or the nucleic acid sequences complementary thereto (nucleotide sequences corresponding to the various variable sequences of the CRISPR1 locus of the serotypes Gallinarum);

set S21-2, comprising or constituted of at least one probe comprising at least or constituted of at least 8 consecutive nucleotides of any one of the nucleic acid sequences SEQ ID Nos: 392, 393, 404, 407 to 415 and/or the nucleic acid sequences complementary thereto (nucleotide sequences corresponding to the various variable sequences of the CRISPR2 locus of the serotypes Gallinarum);

set S22-1, comprising or constituted of at least one probe comprising at least or constituted of at least 8 consecutive nucleotides of the nucleic acid sequence SEQ ID No.: 917 and/or the nucleic acid sequence complementary thereto (nucleotide sequences corresponding to the variable sequence of the CRISPR1 locus of the serotype Brandenburg);

set S22-2, comprising or constituted of at least one probe comprising at least or constituted of at least 8 consecutive nucleotides of any one of the nucleic acid sequences SEQ ID Nos: 225 to 231 and/or the nucleic acid sequences complementary thereto (nucleotide sequences corresponding to the various variable sequences of the CRISPR2 locus of the serotype Brandenburg);

set S23-1, comprising or constituted of at least one probe comprising at least or constituted of at least 8 consecutive nucleotides of any one of the nucleic acid sequences SEQ ID Nos: 378, 379 and/or the nucleic acid sequences complementary thereto (nucleotide sequences corresponding to the various variable sequences of the CRISPR1 locus of the serotype Dublin);

set S23-2, comprising or constituted of at least one probe comprising at least or constituted of at least 8 consecutive nucleotides of any one of the nucleic acid sequences SEQ ID Nos: 392, 393, 411 412 and/or the nucleic acid sequences complementary thereto (nucleotide sequences corresponding to the various variable sequences of the CRISPR2 locus of the serotype Dublin);

set S24-1, comprising or constituted of at least one probe comprising at least or constituted of at least 8 consecutive nucleotides of any one of the nucleic acid sequences SEQ ID Nos: 1, 1106 and/or the nucleic acid sequences complementary thereto (nucleotide sequences corresponding to the various variable sequences of the CRISPR1 locus of the serotype Abortusequi);

set S24-2, comprising or constituted of at least one probe comprising at least or constituted of at least 8 consecutive nucleotides of any one of the nucleic acid sequences SEQ ID Nos: 2 to 10, 130 and/or the nucleic acid sequences complementary thereto (nucleotide sequences corresponding to the various variable sequences of the CRISPR2 locus of the serotype Abortusequi);

set S25-1, comprising or constituted of at least one probe comprising at least or constituted of at least 8 consecutive nucleotides of any one of the nucleic acid sequences SEQ ID Nos: 378, 379 and/or the nucleic acid sequences complementary thereto (nucleotide sequences corresponding to the various variable sequences of the CRISPR1 locus of the serotype Kiel);

set S25-2, comprising or constituted of at least one probe comprising at least or constituted of at least 8 consecutive nucleotides of any one of the nucleic acid sequences SEQ ID Nos: 392, 393, 411, 412 and/or the nucleic acid sequences complementary thereto (nucleotide sequences corresponding to the various variable sequences of the CRISPR2 locus of the serotype Kiel);

set S26-1, comprising or constituted of at least one probe comprising at least or constituted of at least 8 consecutive nucleotides of any one of the nucleic acid sequences SEQ ID Nos: 509, 510, 512 513, 637 to 660, 1086, 1107 and/or the nucleic acid sequences complementary thereto (nucleotide sequences corresponding to the various variable sequences of the CRISPR1 locus of the serotype Mbandaka);

set S26-2, comprising or constituted of at least one probe comprising at least or constituted of at least 8 consecutive nucleotides of any one of the nucleic acid sequences SEQ ID Nos: 661 to 666, 668, 669, 672, 683, 690 to 695, 25 731, 918 and/or the nucleic acid sequences complementary thereto (nucleotide sequences corresponding to the various variable sequences of the CRISPR2 locus of the serotype Mbandaka);

set S27-1, comprising or constituted of at least one probe comprising at least or constituted of at least 8 consecutive nucleotides of any one of the nucleic acid sequences SEQ ID No.: 916 and/or the nucleic acid sequence complementary thereto (nucleotide sequences corresponding to the variable sequence of the CRISPRI locus of the serotype lvliami);

set S27-2, comprising or constituted of at least one probe comprising at least or constituted of at least 8 consecutive nucleotides of any one of the nucleic acid sequences SEQ ID Nos: 25, 696 to 700 and/or the nucleic acid sequences complementary thereto (nucleotide sequences corresponding to the various variable sequences of the CRISPR2 locus of the serotype Miami);

set S28-1, comprising or constituted of at least one probe comprising at Least or constituted of at least 8 consecutive nucleotides of any one of the nucleic acid sequences SEQ ID Nos: 55, 701 to 730, 732 to 768, 1115, 1228, 1232 to 1237, 1601, 1671 to 1680, 1682 to 1694, 1747 and/or the nucleic acid sequences complementary thereto (nucleotide sequences corresponding to the various variable sequences of the CRISPR1 locus of the serotype Montevideo);

set S28-2, comprising or constituted of at least one probe comprising at least or constituted of at least 8 consecutive nucleotides of any one of the nucleic acid sequences SEQ ID Nos: 589, 769 to 829, 933, 1245, 1697, 1698 and/or the nucleic acid sequences complementary thereto (nucleotide sequences corresponding to the various variable sequences of the CRISPR2 locus of the serotype Montevideo);

set S29-1, comprising or constituted of at least one probe comprising at least or constituted of at least 8 consecutive nucleotides of any one of the nucleic acid sequences SEQ ID Nos: 379, 380, 383 to 385, 387, 389 to 391 and/or the nucleic acid sequences complementary thereto (nucleotide sequences corresponding to the various variable sequences of the CRISPR1 locus of the serotype Nitra);

set S29-2, comprising or constituted of at least one probe comprising at least or constituted of at least 8 consecutive nucleotides of any one of the nucleic acid sequences SEQ ID Nos: 392 to 394, 404, 407 to 413, 519 and/or the nucleic acid sequences complementary thereto (nucleotide sequences corresponding to the various variable sequences of the CRISPR2 locus of the serotype Nitra);

set S30-1, comprising or constituted of at least one probe comprising at least or constituted of at least 8 consecutive nucleotides of any one of the nucleic acid sequences SEQ ID Nos: 931, 932, 1104, 1105 and/or the nucleic acid sequences complementary thereto (nucleotide sequences corresponding to the various variable sequences of the CRISPR1 locus of the serotype Sendai);

set S30-2, comprising or constituted of at least one probe comprising at least or constituted of at least 8 consecutive nucleotides of the nucleic acid sequence SEQ ID No.: 936 and/or the nucleic acid sequence complementary thereto (nucleotide sequences corresponding to the variable sequence of the CRISPR2 locus of the serotype Sendai);

set S31-1, comprising or constituted of at least one probe comprising at least or constituted of at least 8 consecutive nucleotides of any one of the nucleic acid sequences SEQ ID Nos: 714 to 716, 1228 to 1239 and/or the nucleic acid sequences complementary thereto (nucleotide sequences corresponding to the various variable sequences of the CRISPR1 locus of the serotype Schwarzengnmd);

set S31-2, comprising or constituted of at least one probe comprising at least or constituted of at least 8 consecutive nucleotides of any one of the nucleic acid sequences SEQ ID Nos: 196, 992, 995, 1172, 1240 to 1244, 1246 to 1253 and/or the nucleic acid sequences complementary thereto (nucleotide sequences corresponding to the various variable sequences of the CRISPR2 locus of the serotype Schwarzengrund);

set S32-1, comprising or constituted of at least one probe comprising at least or constituted of at least 8 consecutive nucleotides of any one of the nucleic acid sequences SEQ ID Nos: 232, 238, 239, 998, 999, 1002, 1106, 1261 and/or the nucleic acid sequences complementary thereto (nucleotide sequences corresponding to the various variable sequences of the CRISPR1 locus of the serotype Typhisuis);

set S32-2, comprising or constituted of at least one probe comprising at least or constituted of at least 8 consecutive nucleotides of the nucleic acid sequence SEQ ID No.: 1262 and/or the nucleic acid sequence complementary thereto (nucleotide sequences corresponding to the variable sequence of the CRISPR2 locus of the serotype Typhisuis);

set S33-1, comprising or constituted of at least one probe comprising at least or constituted of at least 8 consecutive nucleotides of any one of the nucleic acid sequences SEQ ID Nos: 466 to 486 and/or the nucleic acid sequences complementary thereto (nucleotide sequences corresponding to the various variable sequences of the CRISPR1 locus of the various serotypes of the *houtenae* subspecies);

set S33-2, comprising or constituted of at least one probe comprising at least or constituted of at least 8 consecutive nucleotides of any one of the nucleic acid sequences SEQ ID Nos: 487 to 490 and/or the nucleic acid sequences complementary thereto (nucleotide sequences corresponding to the various variable sequences of the CRISPR2 locus of the various serotypes of the *houtenae* subspecies);

set S34-1, comprising or constituted of at least one probe comprising at least or constituted of at least 8 consecutive nucleotides of any one of the nucleic acid sequences SEQ ID Nos: 338 to 376 and/or the nucleic acid sequences complementary thereto (nucleotide sequences corresponding to the various variable sequences of the CRISPR1 locus of the various serotypes of the *diarizonae* subspecies);

set S34-2, comprising or constituted of at least one probe comprising at least or constituted of at least 8 consecutive nucleotides of the nucleic acid sequence SEQ ID No.: 377 and/or the nucleic acid sequence complementary thereto (nucleotide sequences corresponding to the variable sequence of the CRISPR2 locus of the various serotypes of the *diarizonae* subspecies);

set S35-1, comprising or constituted of at least one probe comprising at least or constituted of at least 8 consecutive nucleotides of any one of the nucleic acid sequences SEQ ID Nos: 1007 to 1037, 1848 to 1884 and/or the nucleic acid sequences complementary thereto (nucleotide sequences corresponding to the various variable sequences of the CRISPR1 locus of the *salamae* subspecies);

set S35-2, comprising or constituted of at least one probe comprising at least or constituted of at least 8 consecutive nucleotides of any one of the nucleic acid sequences SEQ ID Nos: 1038 to 1061, 1885 and/or the nucleic acid sequences complementary thereto (nucleotide sequences corresponding to the various variable sequences of the CRISPR2 locus of the *salamae* subspecies);

set S36, comprising or constituted of at least one probe comprising at least or constituted of at least 8 consecutive nucleotides of the nucleic acid sequence SEQ ID No: 95 and/or the nucleic acid sequence complementary thereto (nucleotide sequences corresponding to the variable sequence of the CRISPR1 locus of the various serotypes of the *arizonae* subspecies);

set S37-1, comprising or constituted of at least one probe comprising at least or constituted of at least 8 consecutive nucleotides of any one of the nucleic acid sequences SEQ ID Nos: 491 to 499 and/or the nucleic acid sequences complementary thereto (nucleotide sequences corresponding to the various variable sequences of the CRISPR1 locus of the various serotypes of the *indica* subspecies);

set S37-2, comprising or constituted of at least one probe comprising at least or constituted of at least 8 consecutive nucleotides of any one of the nucleic acid sequences SEQ ID Nos: 500 to 503, 1574 to 1589 and/or the nucleic acid sequences complementary thereto (nucleotide sequences corresponding to the various variable sequences of the CRISPR2 locus of the various serotypes of the *indica* subspecies);

set S38-1, comprising or constituted of at least one probe comprising at least or constituted of at least 8 consecutive nucleotides of any one of the nucleic acid sequences SEQ ID Nos: 32 to 66, 382, 416, 667, 2036 and/or the nucleic acid sequences complementary thereto (nucleotide sequences corresponding to the various variable sequences of the CRISPR1 locus of the serotype Altona);

set S38-2, comprising or constituted of at least one probe comprising at least or constituted of at least 8 consecutive nucleotides of any one of the nucleic acid sequences SEQ ID Nos: 854, 933, 1095, 1306, 1354 to 1389, 1696 and/or the nucleic acid sequences complementary thereto (nucleotide sequences corresponding to the various variable sequences of the CRISPR2 locus of the serotype Altona);

set S39-1, comprising or constituted of at least one probe comprising at least or constituted of at least 8 consecutive nucleotides of any one of the nucleic acid sequences SEQ 10 Nos: 240, 241, 1120, 1121 and/or the nucleic acid sequences complementary thereto (nucleotide sequences corresponding to the various variable sequences of the CRISPR1 locus of the serotype Choleraesuis variety Decatur);

set S39-2, comprising or constituted of at least one probe comprising at least or constituted of at least 8 consecutive nucleotides of any one of the nucleic acid sequences SEQ ID Nos: 225, 247 to 251, 253 to 256, 259 to 268, 270 to 279, 281 to 289, 292 to 294 and/or the nucleic acid sequences complementary thereto (nucleotide sequences corresponding to the various variable sequences of the CRISPR2 locus of the serotype Choleraesuis variety Decatur);

set S40-1, comprising or constituted of at least one probe comprising at least or constituted of at least 8 consecutive nucleotides of any one of the nucleic acid sequences SEQ ID Nos: 11, 232, 238, 239, 240, 242 to 245, 233 to 237, 959, 1106, 1120 and/or the nucleic acid sequences complementary thereto (nucleotide sequences corresponding to the various variable sequences of the CRISPRI locus of the serotype Choleraesuis variety Kunzendorf);

set S40-2, comprising or constituted of at least one probe comprising at least or constituted of at least 8 consecutive nucleotides of any one of the nucleic acid sequences SEQ ID Nos: 246, 252, 258, 269, 280, 290, 291, 392, 563, 933 and/or the nucleic acid sequences complementary thereto (nucleotide sequences corresponding to the various variable sequences of the CRISPR2 locus of the serotype Choleraesuis variety Kunzendorf);

set S41-1, comprising or constituted of at least one probe comprising at least or constituted of at least 8 consecutive nucleotides of any one of the nucleic acid sequences SEQ ID Nos: 11, 242 to 245, 232 to 239, 959, 1000, 1106, 1139, 1120 and/or the nucleic acid sequences complementary thereto (nucleotide sequences corresponding to the various variable sequences of the CRISPR1 locus of the serotypes Choleraesuis and Choleraesuis sensu stricto);

set S41-2, comprising or constituted of at least one probe comprising at least or constituted of at least 8 consecutive nucleotides of any one of the nucleic acid sequences SEQ ID Nos: 246, 252, 258, 269, 280, 290, 291, 392, 563, 574, 933, 1003, 1004 and/or the nucleic acid sequences complementary thereto (nucleotide sequences corresponding to the various variable sequences of the CRISPR2 locus of the serotypes Choleraesuis and Choleraesuis sensu stricto);

set S42-1, comprising or constituted of at least one probe comprising at least or constituted of at least 8 consecutive nucleotides of any one of the nucleic acid sequences SEQ ID Nos: 416 to 420, 1122 and/or the nucleic acid sequences complementary thereto (nucleotide sequences corresponding to the various variable sequences of the CRISPR1 locus of the serotype Goettingen);

set S42-2, comprising or constituted of at least one probe comprising at least or constituted of at least 8 consecutive nucleotides of the nucleic acid sequence SEQ ID No.: 1548 and/or the nucleic acid sequence complementary thereto (nucleotide sequences corresponding to the variable sequence of the CRISPR2 locus of the serotype Goettingen);

set S43-1, comprising or constituted of at least one probe comprising at least or constituted of at least 8 consecutive nucleotides of any one of the nucleic acid sequences SEQ ID Nos: 630 to 636, 937, 948, 1120, 1143 and/or the nucleic acid sequences complementary thereto (nucleotide sequences corresponding to the various variable sequences of the CRISPR1 locus of the serotype Manhattan);

set S43-2, comprising or constituted of at least one probe comprising at least or constituted of at least 8 consecutive nucleotides of any one of the nucleic acid sequences SEQ ID Nos: 392, 1653 and/or the nucleic acid sequences complementary thereto (nucleotide sequences corresponding to the various variable sequences of the CRISPR2 locus of the serotype Manhattan);

set S44-1, comprising or constituted of at least one probe comprising at least or constituted of at least 8 consecutive nucleotides of any one of the nucleic acid sequences SEQ ID Nos: 96 to 155 and/or the nucleic acid sequences complementary thereto (nucleotide sequences corresponding to the various variable sequences of the CRISPR1 locus of certain serotypes of the species *S. bongori*);

set S44-2, comprising or constituted of at least one probe comprising at least or constituted of at least 8 consecutive nucleotides of any one of the nucleic acid sequences SEQ ID Nos: 156 to 195, 1421 to 1430 and/or the nucleic acid sequences complementary thereto (nucleotide sequences corresponding to the various variable sequences of the CRISPR2 locus of certain serotypes of the species *S. bongori*);

set S45-1, comprising or constituted of at least one probe comprising at least or constituted of at least 8 consecutive nucleotides of any one of the nucleic acid sequences SEQ ID Nos: 962, 1106, 1133, 1804, 1808 and/or the nucleic acid sequences complementary thereto (nucleotide sequences corresponding to the various variable sequences of the CRISPR1 locus of the serotype Abony);

set S45-2, comprising or constituted of at least one probe comprising at least or constituted of at least 8 consecutive nucleotides of any one of the nucleic acid sequences SEQ ID Nos: 972, 989, 1334 to 1339, 1474, 1499 and/or the nucleic acid sequences complementary thereto (nucleotide sequences corresponding to the various variable sequences of the CRISPR2 locus of the serotype Abony);

set S46-1, comprising or constituted of at least one probe comprising at least or constituted of at least 8 consecutive nucleotides of any one of the nucleic acid sequences SEQ ID Nos: 448, 860 to 875, 882, 883, 1340 to 1345, 1721 to 1723 and/or the nucleic acid sequences complementary thereto (nucleotide sequences corresponding to the various variable sequences of the CRISPR1 locus of the serotype Aesch);

set S46-2, comprising or constituted of at least one probe comprising at least or constituted of at least 8 consecutive nucleotides of any one of the nucleic acid sequences SEQ ID Nos: 563, 625, 626, 885, 887 to 893, 896, 933, 1346 to 1348, 1749, 1759 and/or the nucleic acid sequences complementary thereto (nucleotide sequences corresponding to the various variable sequences of the CRISPR2 locus of the serotype Aesch);

set S47-1, comprising or constituted of at least one probe comprising at least or constituted of at least 8 consecutive nucleotides of any one of the nucleic acid sequences SEQ ID Nos: 834, 1120, 1349, 1350, 1351, 1713, 1718 and/or the nucleic acid sequences complementary thereto (nucleotide sequences corresponding to the various variable sequences of the CRISPR1 locus of the serotype Albany);

set S47-2, comprising or constituted of at least one probe comprising at least or constituted of at least 8 consecutive nucleotides of any one of the nucleic acid sequences SEQ ID Nos: 842, 852, 1352, 1353 and/or the nucleic acid sequences complementary thereto (nucleotide sequences corresponding to the various variable sequences of the CRISPR2 locus of the serotype Albany);

set S48-1, comprising or constituted of at least one probe comprising at least or constituted of at least 8 consecutive nucleotides of the nucleic acid sequence SEQ ID No.: 917 and/or the nucleic acid sequence complementary thereto (nucleotide sequences corresponding to the variable sequence of the CRISPR1 locus of the serotype Arechavalata);

set S48-2, comprising or constituted of at least one probe comprising at least or constituted of at least 8 consecutive nucleotides of any one of the nucleic acid sequences SEQ ID Nos: 225, 227 to 231, 1398 and/or the nucleic acid sequences complementary thereto (nucleotide sequences corresponding to the various variable sequences of the CRISPR2 locus of the serotype Arechavalata);

set S49-1, comprising or constituted of at least one probe comprising at least or constituted of at least 8 consecutive nucleotides of any one of the nucleic acid sequences SEQ ID Nos: 448, 449, 860, 871 to 873, 878, 895, 903 to 905, 907, 1719 to 1721, 1745 and/or the nucleic acid sequences complementary thereto (nucleotide sequences corresponding to the various variable sequences of the CRISPR1 locus of the serotype Bardo);

set S49-2, comprising or constituted of at least one probe comprising at least or constituted of at least 8 consecutive nucleotides of any one of the nucleic acid sequences SEQ ID Nos: 563, 622, 626, 885, 886 to 890, 893, 896, 907, 910 to 915, 933, 1756 to 1758 and/or the nucleic acid sequences complementary thereto (nucleotide sequences corresponding to the various variable sequences of the CRISPR2 locus of the serotype Bardo);

set S50-1, comprising or constituted of at least one probe comprising at least or constituted of at least 8 consecutive nucleotides of any one of the nucleic acid sequences SEQ ID Nos: 82, 1401 and/or the nucleic acid sequences complementary thereto (nucleotide sequences corresponding to the various variable sequences of the CRISPR1 locus of the serotype Berta);

set S50-2, comprising or constituted of at least one probe comprising at least or constituted of at least 8 consecutive nucleotides of any one of the nucleic acid sequences SEQ ID Nos: 246, 918, 933, 1401, 1448 and/or the nucleic acid sequences complementary thereto (nucleotide sequences corresponding to the various variable sequences of the CRISPR2 locus of the serotype Berta);

set S51-1, comprising or constituted of at least one probe comprising at least or constituted of at least 8 consecutive nucleotides of any one of the nucleic acid sequences SEQ ID Nos: 1, 37, 1106, 1402 to 1416, 2055 and/or the nucleic acid sequences complementary thereto (nucleotide sequences corresponding to the various variable sequences of the CRISPR1 locus of the serotype Bispebjerg);

set S51-2, comprising or constituted of at least one probe comprising at least or constituted of at least 8 consecutive nucleotides of any one of the nucleic acid sequences SEQ ID Nos: 2 to 4, 9, 1417 to 1420, 1547, 1572 and/or the nucleic acid sequences complementary thereto (nucleotide sequences corresponding to the various variable sequences of the CRISPR2 locus of the serotype Bispebjerg);

set S52-1, comprising or constituted of at least one probe comprising at least or constituted of at least 8 consecutive nucleotides of any one of the nucleic acid sequences SEQ ID Nos: 379, 380, 383, 385, 387, 389 to 391 and/or the nucleic acid sequences complementary thereto (nucleotide sequences corresponding to the various variable sequences of the CRISPR1 locus of the serotype Blegdam);

set S52-2, comprising or constituted of at least one probe comprising at least or constituted of at least 8 consecutive nucleotides of any one of the nucleic acid sequences SEQ ID Nos: 392 to 394, 404, 407, 412, 413, 519 and/or the nucleic acid sequences complementary thereto (nucleotide sequences corresponding to the various variable sequences of the CRISPR2 locus of the serotype Blegdam);

set S53-1, comprising or constituted of at least one probe comprising at least or constituted of at least 8 consecutive nucleotides of the nucleic acid sequence SEQ ID No.: 917 and/or the nucleic acid sequence complementary thereto (nucleotide sequences corresponding to the variable sequence of the CRISPR1 locus of the serotype Chester);

set S53-2, comprising or constituted of at least one probe comprising at least or constituted of at least 8 consecutive nucleotides of any one of the nucleic acid sequences SEQ ID Nos: 933, 1445 to 1447 and/or the nucleic acid sequences complementary thereto (nucleotide sequences corresponding to the various variable sequences of the CRISPR2 locus of the serotype Chester);

set S54-1, comprising or constituted of at least one probe comprising at least or constituted of at least 8 consecutive nucleotides of any one of the nucleic acid sequences SEQ ID Nos: 1449 to 1454, 1460, 1467 to 1473 and/or the nucleic acid sequences complementary thereto (nucleotide sequences corresponding to the various variable sequences of the CRISPR1 locus of the serotype Concord);

set S54-2, comprising or constituted of at least one probe comprising at least or constituted of at least 8 consecutive nucleotides of any one of the nucleic acid sequences SEQ ID Nos: 972, 1474 to 1493, 1495 to 1499 and/or the nucleic acid sequences complementary thereto (nucleotide sequences corresponding to the various variable sequences of the CRISPR2 locus of the serotype Concord);

set S55-1, comprising or constituted of at least one probe comprising at least or constituted of at least 8 consecutive nucleotides of any one of the nucleic acid sequences SEQ ID Nos: 1106, 1107 to 1109, 1123, 1128 to 1131, 1133, 1137 to 1140, 1550, 1559 to 1561 and/or the nucleic acid sequences complementary thereto (nucleotide sequences corresponding to the various variable sequences of the CRISPR1 locus of the serotype Crossness);

set S55-2, comprising or constituted of at least one probe comprising at least or constituted of at least 8 consecutive nucleotides of any one of the nucleic acid sequences SEQ ID Nos: 455, 1144, 1145, 1149 to 1153, 1155 to 1160, 1163, 1172 to 1174 and/or the nucleic acid sequences complementary thereto (nucleotide sequences corresponding to the various variable sequences of the CRISPR2 locus of the serotype Crossness);

set S56-1, comprising or constituted of at least one probe comprising at least or constituted of at least 8 consecutive nucleotides of any one of the nucleic acid sequences SEQ ID Nos: 834, 1120, 1349 to 1351 1713, 1718 and/or the nucleic acid sequences complementary thereto (nucleotide sequences corresponding to the various variable sequences of the CRISPR1 locus of the serotype Duesseldorf);

set S56-2, comprising or constituted of at least one probe comprising at least or constituted of at least 8 consecutive nucleotides of any one of the nucleic acid sequences SEQ ID Nos: 842, 852, 1352, 1353, 1501 to 1503 and/or the nucleic acid sequences complementary thereto (nucleotide sequences corresponding to the various variable sequences of the CRISPR2 locus of the serotype Duesseldorf);

set S57-1, comprising or constituted of at least one probe comprising at least or constituted of at least 8 consecutive nucleotides of any one of the nucleic acid sequences SEQ ID Nos: 941, 1504 to 1508 and/or the nucleic acid sequences complementary thereto (nucleotide sequences corresponding to the various variable sequences of the CRISPR1 locus of the serotype Emek);

set S57-2, comprising or constituted of at least one probe comprising at least or constituted of at least 8 consecutive nucleotides of any one of the nucleic acid sequences SEQ ID Nos: 1260, 1509 to 1524, 1526, 1527 and/or the nucleic acid sequences complementary thereto (nucleotide sequences corresponding to the various variable sequences of the CRISPR2 locus of the serotype Emek);

set S58-1, comprising or constituted of at least one probe comprising at least or constituted of at least 8 consecutive nucleotides of the nucleic acid sequence SEQ ID No.: 558 and/or the nucleic acid sequence complementary thereto (nucleotide sequences corresponding to the variable sequence of the CRISPR1 locus of the serotype Fulica);

set S58-2, comprising or constituted of at least one probe comprising at least or constituted of at least 8 consecutive nucleotides of any one of the nucleic acid sequences SEQ ID Nos: 2, 4, 5, 1333, 1547 and/or the nucleic acid sequences complementary thereto (nucleotide sequences corresponding to the various variable sequences of the CRISPR2 locus of the serotype Fulica);

set S59-1, comprising or constituted of at least one probe comprising at least or constituted of at least 8 consecutive nucleotides of the nucleic acid sequence SEQ ID No.: 917 and/or the nucleic acid sequence complementary thereto (nucleotide sequences corresponding to the variable sequence of the CRISPR1 locus of the serotype Gueuletapee);

set S59-2, comprising or constituted of at least one probe comprising at least or constituted of at least 8 consecutive nucleotides of any one of the nucleic acid sequences SEQ ID Nos: 597, 918 to 925, 933, 1549 and/or the nucleic acid sequences complementary thereto (nucleotide sequences corresponding to the various variable sequences of the CRISPR2 locus of the serotype Gueuletapee);

set S60-1, comprising or constituted of at least one probe comprising at least or constituted of at least 8 consecutive nucleotides of any one of the nucleic acid sequences SEQ ID Nos: 1106 to 1109, 1111 to 1116, 1118, 1123, 1128 to 1131, 1133, 1137 to 1140, 1150, 1151, 1555 to 1562 and/or the nucleic acid sequences complementary thereto (nucleotide sequences corresponding to the various variable sequences of the CRISPR1 locus of the serotype Heidelberg);

set S60-2, comprising or constituted of at least one probe comprising at least or constituted of at least 8 consecutive nucleotides of any one of the nucleic acid sequences SEQ ID Nos: 455, 1144, 1145, 1149 to 1153, 1155 to 1163, 1172 to 1174, 1563 and/or the nucleic acid sequences complementary thereto (nucleotide sequences corresponding to the various variable sequences of the CRISPR2 locus of the serotype Heidelberg);

set S61-1, comprising or constituted of at least one probe comprising at least or constituted of at least 8 consecutive nucleotides of any one of the nucleic acid sequences SEQ ID Nos: 558, 1565 to 1571 and/or the nucleic acid sequences complementary thereto (nucleotide sequences corresponding to the various variable sequences of the CRISPR1 locus of the serotype Hessarek);

set S61-2, comprising or constituted of at least one probe comprising at least or constituted of at least 8 consecutive nucleotides of any one of the nucleic acid sequences SEQ ID Nos: 2 to 4, 1547, 1572, 1573 and/or the nucleic acid sequences complementary thereto (nucleotide sequences corresponding to the various variable sequences of the CRISPR2 locus of the serotype Hessarek);

set S62-1, comprising or constituted of at least one probe comprising at least or constituted of at least 8 consecutive nucleotides of any one of the nucleic acid sequences SEQ ID Nos: 1591, 1592, 1667 and/or the nucleic acid sequences complementary thereto (nucleotide sequences corresponding to the various variable sequences of the CRISPR1 locus of the serotype Itami);

set S62-2, comprising or constituted of at least one probe comprising at least or constituted of at least 8 consecutive nucleotides of any one of the nucleic acid sequences SEQ ID Nos: 918, 1593 to 1600, 1744 and/or the nucleic acid sequences complementary thereto (nucleotide sequences corresponding to the various variable sequences of the CRISPR2 locus of the serotype Ramp;

set S63-1, comprising or constituted of at least one probe comprising at least or constituted of at least 8 consecutive nucleotides of any one of the nucleic acid sequences SEQ ID Nos: 1601 to 1606, 1687 and/or the nucleic acid sequences complementary thereto (nucleotide sequences corresponding to the various variable sequences of the CRISPR1 locus of the serotype Javiana);

set S63-2, comprising or constituted of at least one probe comprising at least or constituted of at least 8 consecutive nucleotides of any one of the nucleic acid sequences SEQ ID Nos: 589 to 601, 973, 1607, 1608 and/or the nucleic acid sequences complementary thereto (nucleotide sequences corresponding to the various variable sequences of the CRISPR2 locus of the serotype Javiana);

set S64-1, comprising or constituted of at least one probe comprising at least or constituted of at least 8 consecutive nucleotides of any one of the nucleic acid sequences SEQ ID Nos: 1609 to 1621, 1494, 1525 and/or the nucleic acid sequences complementary thereto (nucleotide sequences corresponding to the various variable sequences of the CRISPR1 locus of the serotype Johannesburg);

set S64-2, comprising or constituted of at least one probe comprising at least or constituted of at least 8 consecutive nucleotides of any one of the nucleic acid sequences SEQ ID Nos: 918, 1697, 1698 and/or the nucleic acid sequences complementary thereto (nucleotide sequences corresponding to the various variable sequences of the CRISPR2 locus of the serotype Johannesburg);

set S65-1, comprising or constituted of at least one probe comprising at least or constituted of at least 8 consecutive nucleotides of any one of the nucleic acid sequences SEQ ID Nos: 444, 448, 1184, 1622 to 1637 and/or the nucleic acid sequences complementary thereto (nucleotide sequences corresponding to the various variable sequences of the CRISPR1 locus of the serotype Kentucky);

set S65-2, comprising or constituted of at least one probe comprising at least or constituted of at least 8 consecutive nucleotides of any one of the nucleic acid sequences SEQ ID Nos: 385, 519, 1638 to 1652, 1746 and/or the nucleic acid sequences complementary thereto (nucleotide sequences corresponding to the various variable sequences of the CRISPR2 locus of the serotype Kentucky);

set S66-1, comprising or constituted of at Least one probe comprising at least or constituted of at least 8 consecutive nucleotides of the nucleic acid sequence SEQ ID No.: 67 and/or the nucleic acid sequence complementary thereto (nucleotide sequences corresponding to the variable sequence of the CRISPR1 locus of the serotype Kundunchi);

set S66-2, comprising or constituted of at least one probe comprising at least or constituted of at least 8 consecutive nucleotides of any one of the nucleic acid sequences SEQ ID Nos: 972, 983, 989, 1201, 1204, 1205, 1210 to 1212 and/or the nucleic acid sequences complementary thereto (nucleotide sequences corresponding to the various variable sequences of the CRISPR2 locus of the serotype Kundunchi);

set S67-1, comprising or constituted of at least one probe comprising at least or constituted of at least 8 consecutive nucleotides of any one of the nucleic acid sequences SEQ ID Nos: 448, 449, 860, 871, 878 to 881, 1721, 1724 and/or the nucleic acid sequences complementary thereto (nucleotide sequences corresponding to the various variable sequences of the CRISPR1 locus of the serotype Lindenburg);

set S67-2, comprising or constituted of at least one probe comprising at least or constituted of at least 8 consecutive nucleotides of any one of the nucleic acid sequences SEQ ID Nos: 563, 622, 885, 886, 896, 907, 910 to 915, 933, 1748, 1757 and/or the nucleic acid sequences complementary thereto (nucleotide sequences corresponding to the various variable sequences of the CRISPR2 locus of the serotype Lindenburg);

set S68-1, comprising or constituted of at least one probe comprising at least or constituted of at least 8 consecutive nucleotides of the nucleic acid sequence SEQ ID No.: 917 and/or the nucleic acid sequence complementary thereto (nucleotide sequences corresponding to the variable sequence of the CRISPR1 locus of the serotype Maracaibo);

set S68-2, comprising or constituted of at least one probe comprising at least or constituted of at least 8 consecutive nucleotides of any one of the nucleic acid sequences SEQ ID Nos: 1240, 1247, 1248, 1654 to 1656 and/or the nucleic acid sequences complementary thereto (nucleotide sequences corresponding to the various variable sequences of the CRISPR2 locus of the serotype Maracaibo);

set S69-1, comprising or constituted of at least one probe comprising at least or constituted of at least 8 consecutive nucleotides of any one of the nucleic acid sequences SEQ ID Nos: 627, 834, 1120, 1660 to 1669 and/or the nucleic acid sequences complementary thereto (nucleotide sequences corresponding to the various variable sequences of the CRISPR1 locus of the serotype Mississippi);

set S69-2, comprising or constituted of at least one probe comprising at least or constituted of at least 8 consecutive nucleotides of any one of the nucleic acid sequences SEQ ID Nos: 842, 1670 and/or the nucleic acid sequences complementary thereto (nucleotide sequences corresponding to the various variable sequences of the CRISPR2 locus of the serotype Mississippi);

set S70-1, comprising or constituted of at least one probe comprising at least or constituted of at least 8 consecutive nucleotides of any one of the nucleic acid sequences SEQ ID Nos: 941, 942, 949, 1699 to 1712, 2109 and/or the nucleic acid sequences complementary thereto (nucleotide sequences corresponding to the various variable sequences of the CRISPR1 locus of the serotype Muenchen);

set S70-2, comprising or constituted of at least one probe comprising at least or constituted of at least 8 consecutive nucleotides of any one of the nucleic acid sequences SEQ ID Nos: 392, 1653 and/or the nucleic acid sequences complementary thereto (nucleotide sequences corresponding to the various variable sequences of the CRISPR2 locus of the serotype Muenchen);

set S71-1, comprising or constituted of at least one probe comprising at least or constituted of at least 8 consecutive nucleotides of any one of the nucleic acid sequences SEQ ID Nos: 11, 1120, 1497, 1760 to 1775, 1809 and/or the nucleic acid sequences complementary thereto (nucleotide sequences corresponding to the various variable sequences of the CRISPR1 locus of the serotype Niarembe);

set S71-2, comprising or constituted of at least one probe comprising at least or constituted of at least 8 consecutive nucleotides of any one of the nucleic acid sequences SEQ ID Nos: 90, 1776 to 1785 and/or the nucleic acid sequences complementary thereto (nucleotide sequences corresponding to the various variable sequences of the CRISPR2 locus of the serotype Niarembe);

set S72-1, comprising or constituted of at least one probe comprising at least or constituted of at least 8 consecutive nucleotides of any one of the nucleic acid sequences SEQ ID Nos: 666, 1786 to 1791 and/or the nucleic acid sequences complementary thereto (nucleotide sequences corresponding to the various variable sequences of the CRISPR1 locus of the serotype Overvecht);

set S72-2, comprising or constituted of at least one probe comprising at least or constituted of at least 8 consecutive nucleotides of any one of the nucleic acid sequences SEQ ID Nos: 783, 1146, 1178, 1179, 1181, 1792 to 1799, 1801 and/or the nucleic acid sequences complementary thereto (nucleotide sequences corresponding to the various variable sequences of the CRISPR2 locus of the serotype Overvecht);

set S73-1, comprising or constituted of at least one probe comprising at least or constituted of at least 8 consecutive nucleotides of the nucleic acid sequence SEQ ID No.: 917 and/or the nucleic acid sequence complementary thereto (nucleotide sequences corresponding to the variable sequence of the CRISPR1 locus of the serotype Poona);

set S73-2, comprising or constituted of at least one probe comprising at least or constituted of at least 8 consecutive nucleotides of any one of the nucleic acid sequences SEQ ID Nos: 82, 87, 918, 933, 1826 and/or the nucleic acid sequences complementary thereto (nucleotide sequences corresponding to the various variable sequences of the CRISPR2 locus of the serotype Poona);

set S74-1, comprising or constituted of at least one probe comprising at least or constituted of at least 8 consecutive nucleotides of any one of the nucleic acid sequences SEQ ID Nos: 295 to 297, 307, 313, 317, 323, 1120, 1825, 1827 to 1837, 2023 and/or the nucleic acid sequences complementary thereto (nucleotide sequences corresponding to the various variable sequences of the CRISPR1 locus of the serotype Potsdam);

set S74-2, comprising or constituted of at least one probe comprising at least or constituted of at least 8 consecutive nucleotides of any one of the nucleic acid sequences SEQ ID Nos: 663, 1304, 1838 to 1847 and/or the nucleic acid sequences complementary thereto (nucleotide sequences corresponding to the various variable sequences of the CRISPR2 locus of the serotype Potsdam);

set S75-1, comprising or constituted of at least one probe comprising at least or constituted of at least 8 consecutive nucleotides of the nucleic acid sequence SEQ ID No.: 917 and/or the nucleic acid sequence complementary thereto (nucleotide sequences corresponding to the variable sequence of the CRISPR1 locus of the serotype Reading);

set S75-2, comprising or constituted of at least one probe comprising at least or constituted of at least 8 consecutive nucleotides of the nucleic acid sequence SEQ ID No.: 225 and/or the nucleic acid sequence complementary thereto (nucleotide sequences corresponding to the variable sequence of the CRISPR2 locus of the serotype Reading);

set S76-1, comprising or constituted of at least one probe comprising at least or constituted of at least 8 consecutive nucleotides of any one of the nucleic acid sequences SEQ ID Nos: 379, 380, 383 to 385, 387, 389, 390 and/or the nucleic acid sequences complementary thereto (nucleotide sequences corresponding to the various variable sequences of the CRISPR1 locus of the serotype Rosenberg);

set S76-2, comprising or constituted of at least one probe comprising at least or constituted of at least 8 consecutive nucleotides of any one of the nucleic acid sequences SEQ ID Nos: 392, 393, 404, 407 to 413 and/or the nucleic acid sequences complementary thereto (nucleotide sequences corresponding to the various variable sequences of the CRISPR2 locus of the serotype Rosenberg);

set S77-1, comprising or constituted of at least one probe comprising at least or constituted of at least 8 consecutive nucleotides of the nucleic acid sequence SEQ ID No.: 917 and/or the nucleic acid sequence complementary thereto (nucleotide sequences corresponding to the variable sequence of the CRISPR1 locus of the serotype Rubislaw);

set S77-2, comprising or constituted of at least one probe comprising at least or constituted of at least 8 consecutive nucleotides of the nucleic acid sequence SEQ ID No.: 225 and/or the nucleic acid sequence complementary thereto (nucleotide sequences corresponding to the variable sequence of the CRISPR1 locus of the serotype Rubislaw);

set S78-1, comprising or constituted of at least one probe comprising at least or constituted of at least 8 consecutive nucleotides of any one of the nucleic acid sequences SEQ ID Nos: 1525, 1609 to 1621 and/or the nucleic acid sequences complementary thereto (nucleotide sequences corresponding to the various variable sequences of the CRISPR2 locus of the serotype Sandiego);

set S78-2, comprising or constituted of at least one probe comprising at least or constituted of at least 8 consecutive nucleotides of any one of the nucleic acid sequences SEQ ID Nos: 225 to 227, 229 to 231 and/or the nucleic acid sequences complementary thereto (nucleotide sequences corresponding to the various variable sequences of the CRISPR2 locus of the serotype Sandiego);

set S79-1, comprising or constituted of at least one probe comprising at least or constituted of at least 8 consecutive nucleotides of any one of the nucleic acid sequences SEQ ID Nos: 1106, 1456, 1917 to 1924 and/or the nucleic acid sequences complementary thereto (nucleotide sequences corresponding to the various variable sequences of the CRISPR1 locus of the serotype Stourbridge);

set S79-2, comprising or constituted of at least one probe comprising at least or constituted of at least 8 consecutive nucleotides of any one of the nucleic acid sequences SEQ ID Nos: 918, 1093, 1925 to 1936 and/or the nucleic acid sequences complementary thereto (nucleotide sequences corresponding to the various variable sequences of the CRISPR2 locus of the serotype Stourbridge);

set S80-1, comprising or constituted of at least one probe comprising at least or constituted of at least 8 consecutive nucleotides of any one of the nucleic acid sequences SEQ ID Nos: 1961 to 1963 and/or the nucleic acid sequences complementary thereto (nucleotide sequences corresponding to the various variable sequences of the CRISPR1 locus of the serotype Tallahassee);

set S80-2, comprising or constituted of at least one probe comprising at least or constituted of at least 8 consecutive nucleotides of any one of the nucleic acid sequences SEQ ID Nos: 25, 603, 2127, 2133, 1964 to 1966 and/or the nucleic acid sequences complementary thereto (nucleotide sequences corresponding to the various variable sequences of the CRISPR2 locus of the serotype Tallahassee);

set S81-1, comprising or constituted of at least one probe comprising at least or constituted of at least 8 consecutive nucleotides of any one of the nucleic acid sequences SEQ ID Nos: 67, 929, 1967 to 2005 and/or the nucleic acid sequences complementary thereto (nucleotide sequences corresponding to the various variable sequences of the CRISPR1 locus of the serotype Tennessee);

set S81-2, comprising or constituted of at least one probe comprising at least or constituted of at least 8 consecutive nucleotides of any one of the nucleic acid sequences SEQ ID Nos: 24, 769, 1550, 1659, 2006 to 2022 and/or the nucleic acid sequences complementary thereto (nucleotide sequences corresponding to the various variable sequences of the CRISPR2 locus of the serotype Tennessee);

set S82-1, comprising or constituted of at least one probe comprising at least or constituted of at least 8 consecutive nucleotides of the nucleic acid sequence SEQ ID No.: 916 and/or the nucleic acid sequence complementary thereto (nucleotide sequences corresponding to the variable sequence of the CRISPR1 locus of the serotype Urbana);

set S82-2, comprising or constituted of at least one probe comprising at least or constituted of at least 8 consecutive nucleotides of any one of the nucleic acid sequences SEQ ID Nos: 1697, 1698, 1800 and/or the nucleic acid sequences complementary thereto (nucleotide sequences corresponding to the various variable sequences of the CRISPR2 locus of the serotype Urbana);

set S83-1, comprising or constituted of at least one probe comprising at least or constituted of at least 8 consecutive nucleotides of any one of the nucleic acid sequences SEQ ID Nos; 948, 1120, 1123, 1325, 2039 to 2078 and/or the nucleic acid sequences complementary thereto (nucleotide sequences corresponding to the various variable sequences of the CRISPR1 locus of the serotype Weltevreden);

set S83-2, comprising or constituted of at least one probe comprising at least or constituted of at least 8 consecutive nucleotides of any one of the nucleic acid sequences SEQ ID Nos: 254 to 256, 2079 to 2108 and/or the nucleic acid sequences complementary thereto (nucleotide sequences corresponding to the various variable sequences of the CRISPR2 locus of the serotype Weltevreden);

set S84-1, comprising or constituted of at least one probe comprising at least or constituted of at least 8 consecutive nucleotides of any one of the nucleic acid sequences SEQ ID Nos: 1312, 1690, 2141, 2142 and/or the nucleic acid sequences complementary thereto (nucleotide sequences corresponding to the various variable sequences of the CRISPR1 locus of the serotype Zaiman);

set S84-2, comprising or constituted of at least one probe comprising at least or constituted of at least 8 consecutive nucleotides of any one of the nucleic acid sequences SEQ ID Nos: 1697, 1698, 1800, 1924, 2143, 2144 and/or the nucleic acid sequences complementary thereto (nucleotide sequences corresponding to the various variable sequences of the CRISPR2 locus of the serotype Zaiman); and (ii) detection of the hybridized probes.

11. The method as claimed in claim 10, characterized in that the probes have a length of between 8 and 76 nucleotides, preferably between 8 and 34 nucleotides.

12. The method as claimed in claim 10 or claim 11, characterized in that said step (b) is carried out by hybridization of at least one probe of each of sets S1-1 to S6-2.

13. The method as claimed in claim 12, characterized in that said step (b) is carried out by hybridization, in addition, of at least one probe of each of sets S7-1 to S10-2.

14. The method as claimed in claim 13, characterized in that said step (b) is carried out by hybridization of at least one probe of each of sets S1-1 to S44-2.

15. The method as claimed in claim 1, characterized in that the amplified nucleic acid fragments are labeled.

16. The method as claimed in claim 1, characterized in that the sample is an isolated bacterial strain of the *Salmonella* genus.

17. The method as claimed in claim 1, characterized in that step (a) is preceded by a step of extraction of nucleic acids present in said sample.

* * * * *

UNITED STATES PATENT AND TRADEMARK OFFICE
CERTIFICATE OF CORRECTION

PATENT NO. : 8,673,568 B2
APPLICATION NO. : 12/811055
DATED : March 18, 2014
INVENTOR(S) : François-Xavier Weill et al.

It is certified that error appears in the above-identified patent and that said Letters Patent is hereby corrected as shown below:

IN THE CLAIMS:

Claim 1, col. 41, line 49, "1000 by" should read --1000 bp--.

Claim 1, col. 42, line 40, "1000 by" should read --1000 bp--.

Claim 1, col. 42, line 47, "A1as" should read --A1 as--.

Claim 4, col. 43, line 1, "as claimed in any one of claim 1" should read --as claimed in claim 1--.

Claim 10, col. 46, line 19, "serotype Agana" should read --serotype Agona--.

Claim 10, col. 50, line 2, "CRISPRI" should read --CRISPR1--.

Claim 10, col. 50, line 3, "serotype lvliami" should read --serotype Miami--.

Claim 10, col. 50, line 14, "at Least" should read --at least--.

Claim 10, col. 50, line 67, "serotype Schwarzengnmd" should read --serotype Schwarzengrund--.

Claim 10, col. 53, line 2, "CRISPRI" should read --CRISPR1--.

Claim 10, col. 58, line 27, "serotype Ramp" should read --serotype Itami--.

Claim 10, col. 59, line 9, "at Least" should read --at least--.

Claim 10, col. 60, line 10, "CRISPRI" should read --CRISPR1--.

Signed and Sealed this
Twenty-fourth Day of June, 2014

Michelle K. Lee
*Deputy Director of the United States Patent and Trademark Office*